United States Patent
Casolari et al.

(10) Patent No.: US 10,125,382 B2
(45) Date of Patent: Nov. 13, 2018

(54) ACYL-ACP THIOESTERASES AND MUTANTS THEREOF

(71) Applicant: Corbion Biotech, Inc., South San Francisco, CA (US)

(72) Inventors: Jason Casolari, South San Francisco, CA (US); George N. Rudenko, South San Francisco, CA (US); Scott Franklin, South San Francisco, CA (US); Xinhua Zhao, South San Francisco, CA (US)

(73) Assignee: CORBION BIOTECH, INC., South San Francisco, CA (US)

( * ) Notice: Subject to any disclaimer, the term of this patent is extended or adjusted under 35 U.S.C. 154(b) by 94 days.

(21) Appl. No.: 14/858,527

(22) Filed: Sep. 18, 2015

(65) Prior Publication Data

US 2016/0083758 A1  Mar. 24, 2016

Related U.S. Application Data

(60) Provisional application No. 62/075,168, filed on Nov. 4, 2014, provisional application No. 62/052,440, filed on Sep. 18, 2014.

(51) Int. Cl.

| | |
|---|---|
| *C12N 9/16* | (2006.01) |
| *C12N 15/52* | (2006.01) |
| *C12N 15/00* | (2006.01) |
| *C12N 1/12* | (2006.01) |
| *C12P 7/64* | (2006.01) |
| *C12N 9/24* | (2006.01) |
| *C12N 15/82* | (2006.01) |
| *C12N 9/04* | (2006.01) |
| *C12P 7/44* | (2006.01) |

(52) U.S. Cl.
CPC .......... *C12P 7/6463* (2013.01); *C12N 9/0006* (2013.01); *C12N 9/16* (2013.01); *C12N 9/2402* (2013.01); *C12N 15/52* (2013.01); *C12N 15/8247* (2013.01); *C12P 7/44* (2013.01); *C12Y 301/02014* (2013.01)

(58) Field of Classification Search
None
See application file for complete search history.

(56) References Cited

U.S. PATENT DOCUMENTS

| | | |
|---|---|---|
| 4,049,724 A | 9/1977 | Sheng et al. |
| 4,288,378 A | 9/1981 | Japikse et al. |
| 4,335,156 A | 6/1982 | Kogan et al. |
| 4,584,139 A | 4/1986 | Gray et al. |
| 4,603,188 A | 7/1986 | Kusakawa et al. |
| 4,683,202 A | 7/1987 | Mullis |
| 4,798,793 A | 1/1989 | Eigtved |
| 4,940,835 A | 7/1990 | Shah et al. |
| 4,940,845 A | 7/1990 | Hirota et al. |
| 4,945,050 A | 7/1990 | Sanford et al. |
| 4,992,189 A | 2/1991 | Chen et al. |
| 5,080,848 A | 1/1992 | Strauss et al. |
| 5,091,116 A | 2/1992 | Krishnamurthy et al. |
| 5,156,963 A | 10/1992 | Eigtved |
| 5,233,099 A | 8/1993 | Tabata |
| 5,233,100 A | 8/1993 | Tabata et al. |
| 5,258,197 A | 11/1993 | Wheeler et al. |
| 5,268,192 A | 12/1993 | Zook et al. |
| 5,298,421 A | 3/1994 | Davies et al. |
| 5,298,637 A | 3/1994 | Cooper |
| 5,304,481 A | 4/1994 | Davies et al. |
| 5,304,664 A | 4/1994 | Peppmoller et al. |
| 5,342,768 A | 8/1994 | Pedersen et al. |
| 5,344,771 A | 9/1994 | Davies et al. |
| 5,346,724 A | 9/1994 | Ohgake et al. |
| 5,380,894 A | 1/1995 | Burg et al. |
| 5,391,383 A | 2/1995 | Sullivan et al. |
| 5,427,704 A | 6/1995 | Lawate |
| 5,434,278 A | 7/1995 | Pelloso et al. |
| 5,451,332 A | 9/1995 | Lawate |
| 5,455,167 A | 10/1995 | Voelker et al. |
| 5,458,795 A | 10/1995 | Lawate |
| 5,475,160 A | 12/1995 | Singleton et al. |
| 5,506,201 A | 4/1996 | McDermott et al. |
| 5,512,482 A | 4/1996 | Voelker et al. |
| 5,567,359 A | 10/1996 | Cassidy et al. |

(Continued)

FOREIGN PATENT DOCUMENTS

| | | |
|---|---|---|
| CN | 102066569 A | 5/2011 |
| CN | 102 300 996 A | 12/2011 |

(Continued)

OTHER PUBLICATIONS

U.S. Appl. No. 15/062,045, filed Mar. 5, 2016, Rudenko et al.
U.S. Office Action, dated Jul. 16, 2015, issued in U.S. Appl. No. 13/797,733.
U.S. Final Office Action, dated Dec. 14, 2015, issued in U.S. Appl. No. 13/797,733.
U.S. Office Action, dated Jul. 22, 2015, issued in U.S. Appl. No. 13/837,996.
U.S. Notice of Allowance, dated Nov. 17, 2015, issued in U.S. Appl. No. 13/837,996.
PCT International Search Report and Written Opinion dated Jun. 24, 2014 issued in PCT/US2014/013676.

(Continued)

*Primary Examiner* — Kagnew H Gebreyesus
(74) *Attorney, Agent, or Firm* — Emily M. Haliday; Weaver Austin Villeneuve & Sampson LLP

(57) ABSTRACT

Novel plant acyl-ACP thioesterase genes of the FatB and FatA classes and proteins encoded by these genes are disclosed. The genes are useful for constructing recombinant host cells having altered fatty acid profiles. Expression of the novel and/or mutated FATB and FATA genes is demonstrated in oleaginous microalga host cells. Furthermore, a method for producing an oil elevated in one or more of C12:0, C14:0, C16:0, C18:0 and/or C18:1 fatty acids includes transforming a cell with novel and/or mutated FATB and/or FATA genes, e.g., having an N-terminal deletion. The cells produce triglycerides with altered and useful fatty acid profiles.

21 Claims, No Drawings

Specification includes a Sequence Listing.

(56) References Cited

U.S. PATENT DOCUMENTS

| | | |
|---|---|---|
| 5,576,027 A | 11/1996 | Friedman et al. |
| 5,639,790 A | 6/1997 | Voelker et al. |
| 5,654,495 A | 8/1997 | Voelker et al. |
| 5,667,997 A | 9/1997 | Voelker et al. |
| 5,674,385 A | 10/1997 | Ivaschenko et al. |
| 5,686,131 A | 11/1997 | Sato et al. |
| 5,693,507 A | 12/1997 | Daniell et al. |
| 5,723,761 A | 3/1998 | Voelker et al. |
| 5,776,741 A | 7/1998 | Pedersen et al. |
| 5,807,893 A | 9/1998 | Voelker et al. |
| 5,833,999 A | 11/1998 | Trinh et al. |
| 5,850,022 A | 12/1998 | Dehesh et al. |
| 5,885,440 A | 3/1999 | Hoehn et al. |
| 5,888,947 A | 3/1999 | Lambert et al. |
| 5,910,631 A | 6/1999 | Topfer et al. |
| 5,928,696 A | 7/1999 | Best et al. |
| 5,942,479 A | 8/1999 | Frankenbach et al. |
| 5,945,585 A | 8/1999 | Hitz et al. |
| 6,020,509 A | 2/2000 | Weerasooriya et al. |
| 6,022,577 A | 2/2000 | Chrysam et al. |
| 6,027,900 A | 2/2000 | Allnutt et al. |
| 6,051,539 A | 4/2000 | Kodali et al. |
| 6,057,375 A | 5/2000 | Wollenweber et al. |
| 6,080,853 A | 6/2000 | Corrigan et al. |
| 6,086,903 A | 7/2000 | Trinh et al. |
| 6,113,971 A | 9/2000 | Elmaleh |
| 6,140,302 A | 10/2000 | Lueder et al. |
| 6,150,512 A | 11/2000 | Yuan |
| 6,217,746 B1 | 4/2001 | Thakkar et al. |
| 6,268,517 B1 | 7/2001 | Filler et al. |
| 6,278,006 B1 | 8/2001 | Kodali et al. |
| 6,320,101 B1 | 11/2001 | Kaplan et al. |
| 6,331,664 B1 | 12/2001 | Rubin-Wilson et al. |
| 6,342,208 B1 | 1/2002 | Hyldgaard et al. |
| 6,380,410 B1 | 4/2002 | Oftring et al. |
| 6,391,815 B1 | 5/2002 | Weston et al. |
| 6,395,965 B1 | 5/2002 | Xia |
| 6,398,707 B1 | 6/2002 | Wu et al. |
| 6,407,044 B2 | 6/2002 | Dixon |
| 6,465,642 B1 | 10/2002 | Kenneally et al. |
| 6,468,955 B1 | 10/2002 | Smets et al. |
| 6,538,169 B1 | 3/2003 | Pittman et al. |
| 6,590,113 B1 | 7/2003 | Sleeter |
| 6,596,155 B1 | 7/2003 | Gates et al. |
| 6,596,768 B2 | 7/2003 | Block et al. |
| 6,630,066 B2 | 10/2003 | Cash et al. |
| 6,680,426 B2 | 1/2004 | Daniell et al. |
| 6,692,730 B2 | 2/2004 | Perron et al. |
| 6,750,048 B2 | 6/2004 | Ruecker et al. |
| 6,770,104 B2 | 8/2004 | Murphy |
| 6,808,737 B2 | 10/2004 | Ullanoormadam |
| 6,869,597 B2 | 3/2005 | Arnaud |
| 6,881,873 B2 | 4/2005 | Gillespie et al. |
| 6,924,333 B2 | 8/2005 | Bloom et al. |
| 6,946,430 B2 | 9/2005 | Sakai et al. |
| 6,977,322 B2 | 12/2005 | Gillespie |
| 7,041,866 B1 | 5/2006 | Gillespie |
| 7,053,267 B2 | 5/2006 | Knauf et al. |
| 7,081,567 B2 | 7/2006 | Xue et al. |
| 7,115,173 B2 | 10/2006 | Caswell et al. |
| 7,115,760 B2 | 10/2006 | Sparso et al. |
| 7,118,773 B2 | 10/2006 | Floeter et al. |
| 7,135,290 B2 | 11/2006 | Dillon |
| 7,135,620 B2 | 11/2006 | Daniell et al. |
| 7,196,124 B2 | 3/2007 | Parker et al. |
| 7,232,935 B2 | 6/2007 | Jakkula et al. |
| 7,238,277 B2 | 7/2007 | Dahlberg et al. |
| 7,262,158 B1 | 8/2007 | Lukenbach et al. |
| 7,264,886 B2 | 9/2007 | Cui et al. |
| 7,268,276 B2 | 9/2007 | Ruezinksy et al. |
| 7,288,278 B2 | 10/2007 | Mellerup et al. |
| 7,288,685 B2 | 10/2007 | Marker |
| 7,588,931 B2 | 9/2009 | Damude et al. |
| 7,622,570 B2 | 11/2009 | Oswald et al. |
| 8,029,579 B2 | 10/2011 | Knuth et al. |
| 8,530,207 B2 | 9/2013 | Watts et al. |
| 9,290,749 B2 | 3/2016 | Rudenko et al. |
| 9,567,615 B2 | 2/2017 | Davis |
| 9,765,368 B2 | 9/2017 | Davis et al. |
| 9,783,836 B2 | 10/2017 | Rudenko et al. |
| 9,816,079 B2 | 11/2017 | Davis |
| 2002/0178467 A1 | 11/2002 | Dehesh |
| 2003/0097686 A1 | 5/2003 | Knauf et al. |
| 2003/0145350 A1 | 7/2003 | Spener et al. |
| 2005/0005333 A1 | 1/2005 | Ruezinsky et al. |
| 2005/0102716 A1 | 5/2005 | Venkatramesh et al. |
| 2005/0262588 A1 | 11/2005 | Dehesh et al. |
| 2007/0175091 A1 | 8/2007 | Danzer et al. |
| 2007/0261138 A1 | 11/2007 | Graham et al. |
| 2009/0176272 A1 | 7/2009 | Champagne et al. |
| 2009/0317878 A1 | 12/2009 | Champagne et al. |
| 2010/0058651 A1 | 3/2010 | Knuth et al. |
| 2010/0105955 A1 | 4/2010 | Alibhai et al. |
| 2010/0154293 A1 | 6/2010 | Hom et al. |
| 2011/0072714 A1 | 3/2011 | Gaertner et al. |
| 2011/0145944 A1 | 6/2011 | Laga et al. |
| 2011/0250659 A1 | 10/2011 | Roberts et al. |
| 2011/0293785 A1 | 12/2011 | Franklin et al. |
| 2012/0009636 A1 | 1/2012 | Berry et al. |
| 2012/0283460 A1 | 11/2012 | Franklin et al. |
| 2012/0288930 A1 | 11/2012 | Trimbur et al. |
| 2013/0029387 A1 | 1/2013 | Nikolau et al. |
| 2013/0031678 A1 | 1/2013 | Zheng et al. |
| 2013/0034887 A1 | 2/2013 | Franklin et al. |
| 2014/0215654 A1 | 7/2014 | Davis |
| 2014/0234920 A1 | 8/2014 | Davis |
| 2014/0275586 A1 | 9/2014 | Rudenko et al. |
| 2014/0288320 A1 | 9/2014 | Rudenko et al. |
| 2016/0032332 A1 | 2/2016 | Davis et al. |
| 2016/0251685 A1 | 9/2016 | Rudenko et al. |
| 2018/0148747 A1 | 5/2018 | Davis et al. |
| 2018/0171312 A1 | 6/2018 | Davis |

FOREIGN PATENT DOCUMENTS

| | | |
|---|---|---|
| CN | 102459569 A | 5/2012 |
| CN | 102 559 727 A | 7/2012 |
| CN | 102 586 350 A | 7/2012 |
| EP | 1 605 048 A1 | 12/2005 |
| EP | 1 640 437 A1 | 3/2006 |
| EP | 1 681 337 A1 | 7/2006 |
| EP | 1 741 767 A1 | 1/2007 |
| EP | 1 741 768 A1 | 1/2007 |
| EP | 1 795 576 A1 | 6/2007 |
| EP | 1 682 466 A1 | 11/2008 |
| JP | 11-505115 A | 5/1999 |
| JP | 2012-510275 A | 5/2012 |
| WO | WO 89/01032 A1 | 2/1989 |
| WO | WO 92/11373 A1 | 7/1992 |
| WO | WO 92/020236 | 11/1992 |
| WO | WO 92/20636 A1 | 11/1992 |
| WO | WO 94/10288 A2 | 5/1994 |
| WO | WO 95/13390 A2 | 5/1995 |
| WO | WO 96/23892 A2 | 8/1996 |
| WO | WO 96/36719 A1 | 11/1996 |
| WO | WO 98/55633 A1 | 12/1998 |
| WO | WO 00/61740 A1 | 10/2000 |
| WO | WO 00/66750 A2 | 11/2000 |
| WO | WO 02/08403 A2 | 1/2002 |
| WO | WO 2005/047216 A1 | 5/2005 |
| WO | WO 2006/055322 A2 | 5/2006 |
| WO | WO 2007/106903 A2 | 9/2007 |
| WO | WO 2008/002643 A2 | 1/2008 |
| WO | WO 2008/151149 A2 | 12/2008 |
| WO | WO 2010/019813 A2 | 2/2010 |
| WO | WO 2010/063031 A2 | 6/2010 |
| WO | WO 2010/063032 A2 | 6/2010 |
| WO | WO 2010/120939 A2 | 10/2010 |
| WO | WO 2011/003034 A2 | 1/2011 |
| WO | WO 2011/008565 A1 | 1/2011 |
| WO | WO 2011/127069 A1 | 10/2011 |
| WO | WO 2011/150410 A2 | 12/2011 |
| WO | WO 2011/150411 A1 | 12/2011 |
| WO | WO 2012/061647 A2 | 5/2012 |

(56) References Cited

FOREIGN PATENT DOCUMENTS

| WO | WO 2012/106560 A1 | 8/2012 |
|---|---|---|
| WO | WO 2012/154626 A1 | 11/2012 |
| WO | WO 2013/158938 A1 | 10/2013 |
| WO | WO 2014/120829 A1 | 8/2014 |
| WO | WO 2014/151904 A1 | 9/2014 |
| WO | WO 2015/051319 A2 | 4/2015 |
| WO | WO 2016/014968 A1 | 1/2016 |
| WO | WO 2016/044779 A2 | 3/2016 |

OTHER PUBLICATIONS

PCT International Preliminary Report on Patentability and Written Opinion dated Aug. 13, 2015 issued in PCT/US2014/013676.
Database Geneseq [Online] (Jun. 6, 2000) "Bay C18:1 preferring acyl-ACP thioesterase protein from clone 3A-17.", retrieved from EBI accession No. GSP:AAY80558 Database accession No. AAY80558; and Database Geneseq [Online] (Jun. 6, 2000) "Bay C18:1 preferring acyl-ACP thioesterase protein.", retrieved from EBI accession No. GSP:AAY80559 Database accession No. AAY80559.
Database Geneseq [Online] (Nov. 2, 1995) "Camphor thioesterase.", retrieved from EBI accession No. GSP:AAR74148 Database accession No. AAR74148.
Database Geneseq [Online] (Oct. 26, 1996) "Cuphea C14:0-ACP thioesterase.", retrieved from EBI accession No. GSP:AAW02081 Database accession No. AAW02081.
Database Geneseq [Online] (Aug. 5, 2010) "U. californica fatty acyl-ACP thioesterase protein (without PTS), SEQ:139.", retrieved from EBI accession No. GSP:AYC84249 Database accession No. AYC84249.
Mexican Office Action [no tranlsation] dated Sep. 21, 2015 issued in MX/a/2015/009730.
PCT Invitation to Pay Additional Fees and, Where Applicable, Protest Fee dated Jun. 18, 2014 issued in PCT/US2014/026644.
PCT International Search Report and Written Opinion dated Aug. 29, 2014 issued in PCT/US2014/026644.
PCT International Preliminary Report on Patentability dated Sep. 24, 2015 issued in PCT/US2014/026644.
Genbank Accession No. U17097, Umbellularia californica UC FatB2 (FatB) mRNA, complete cds., Jun. 1, 1995, 2pp.
Genbank: Accession No. U39834.1, Cuphea hookeriana 8:0- and 10:0-ACP specific thioesterase (FatB2) mRNA, complete cds, May 21, 2014, 2pp.
Genbank Accession No. AAC49001, UC FatB2 (FatB) Umbellularica californica, May 30, 1995, 2pp.
PCT International Search Report and Written Opinion dated Dec. 22, 2015 issued in PCT/US2015/042044.
Database UniProt [Online] (Jul. 24, 2013) "SubName: Full =FatB type acyl-ACP thioesterase-3 {EC0;0000313;EMBL:AGG79285.1}," retrieved on Nov. 10, 2015 from EBI accession No. UNIPROT:R4J2L6, Database accession No. R4J2L6 sequence, 1 page.
Database UniProt [Online] (Jul. 9, 2014) "SubName: Full= Uncharacterized protein {EC0:0000313:EMBL:KCW58039.1}," retrieved on Nov. 16, 2015 from EBI accession No. UNIPROT:A0A059AWB4, Database accession No. A0A059AWB4 sequence, 1 page.
PCT Invitation to Pay Additional Fees and, Where Applicable, Protest Fee dated Jan. 13, 2016 issued in PCT/US2015/051042.
PCT International Search Report and Written Opinion dated Mar. 31, 2016 issued in PCT/US2015/051042.
Apt et al., (1996) "Stable nuclear transformation of the diatom *Phaeodactylum tricornutum*," *Molecular and General Genetics*, 252:572-579.
Barnes et al., (2005) "Contribution of 5'- and 3'-untranslated regions of plastid mRNAs to the expression of *Chlamydomonas reinhardtii* chloroplast genes," *Mol Gen Genomics* 274:625-636.
Blatti et al., (Sep. 2012) "Manipulating Fatty Acid Biosynthesis in Microalgae for Biofuel through Protein-Protein Interactions," *PLoS ONE* 7(9):e42949, 12pp.
Blowers et al., (Jan. 1989) "Studies on *Chlamydomonas* Chloroplast Transformation: Foreign DNA Can Be Stably Maintained in the Chromosome," *The Plant Cell*, 1:123-132.
Bonaventure et al., (Apr. 2003) "Disruption of the FATB Gene in Arabidopsis Dethonstrates an Essential Role of Saturated Fatty Acids in Plant Growth," *The Plant Cell* 15:1020-1033.
Boynton et al., (1988) "Chloroplast Transformation in *Chlamydomonas* with High Velocity Microprojectiles," *Science*, 240(4858):1534-1538.
Chasan, (Mar. 1995) "Engineering Fatty Acids—The Long and Short of It," *Plant Cell*, 7:235-237.
Chen et al., (1988) "Recognition of prokaryotic transcription terminators by spinach chloroplast RNA polymerase," *Nucleic Acids Research*, 16(17): 8411-8431.
Chen et al., (2001) "Highly efficient expression of rabbit neutrophil peptide-1 gene in *Chlorella ellipsoidea* cells," *Current Genetics*, 39(5):365-370.
Chow et al.,(1999) "Electrotransformation of *Chlorella vulgaris*," *Plant Cell Reports*, 18:778-780.
Cobley et al., (Sep. 1993) "Construction of Shuttle Plasmids Which Can Be Efficiently Mobilzed from *Escherichia coli* into the Chromatically Adapting Cyanobacterium, *Fremyella diplosiphon*," *Plasmid*, 30(2):90-105.
Cobley et al., (2002) "CpeR is an activator required for expression of the phycoerythrin operon (cpeBA) in the cyanobacterium Fremyella diplosiphon and is encoded in the phycoerythrin linker-polypeptide operon (cpeCDESTR)," *Molecular Microbiololgy*, 44(6): 1517-1531.
Comai et al.,(Oct. 15, 1988) "Chloroplast Transport of a Ribulose Bisphosphate Carboxylase Small Subunit-5-Enolpyruvyl 3-Phosphoshikimate Synthase Chimeric Protein Requires Part of the Mature Small Subunit in Addition to the Transit Peptide," *The Journal of Biological Chemistry*, 263 (29):15104-15109.
Courchesne, Noémie Manuelle Dorval el al., (2009) "Enhancement of lipid production using biochemical, genetic and transcription factor engineering approaches," *Journal of Biotechnology*, 141(1):31-41.
Davies et al., (1992) "Expression of the arylsulfatase gene from the $\beta_2$-tubulin promoter in *Chlamydomonas reinhardtii*," *Nucleic Acids Res.*, 20(12):2959-2965.
Dawson et al.,(1997) "Stable Transformation of *Chlorella*: Rescue of Nitrate Reductase-Deficient Mutants with the Nitrate Reductase Gene," *Current Microbiol.*, 35(6):356-362.
Debuchy et al.,(1989) "The argininosuccinate lyase gene of *Chlamydomonas reinhardtii*: an important tool for nuclear transformation and for correlating the genetic and molecular maps of the ARG7 locus," *EMBO Journal*, 8(10):2803-2809.
Dehesh et al. (1996) "Production of high levels of 8:0 and 10:0 fatty acids in transgenic canola by overexpression of Ch FatB2, a thioesterase cDNA from *Cuphea hookeriana*," *The Plant Journal*, 9(2):167-172.
Dehesh et al., (1998) "KAS IV: a 3-ketoacyl-ACP synthase from *Cuphea* sp. is a medium chain specific condensing enzyme," *The Plant Journal*, 15:383-390.
Deshnium et al.,(1995) "Transformation of *Synechococcus* with a gene for choline oxidase enhances tolerance to salt stress," *Plant Mol. Biol.*, 29(5):897-907.
Dörmann et al., (Jan. 1995) "Cloning and Expression in *Escherichia coli* of a Novel Thioesterase from *Arabidopsis thaliana* Specific for Long-Chain Acyl-Acyl Carrier Proteins," *Archives of Biochemistry and Biophysics*, 316(1):612-618.
Eccleston et al., (1996) "Medium-chain fatty Acid biosynthesis and utilization in *Brassica napus* plants expressing lauroyl-acyl carrier protein thioesterase," *Planta*, 198:46-53.
El-Sheekh et al., (1999) "Stable transformation of the intact cells of *Chlorella kessleri* with high velocity microprojectiles," *Biologia Plantarium*, 42:(2):209-216.
Facciotti et al., (1998) "Molecular dissection of the plant acyl-acyl carrier protein thioesterases," *Fett/Lipid*, 100(4-5, S.):167-172.
Facciotti et al.,(Jun. 1, 1999) "Improved stearate phenotype in transgenic canola expressing a modified acyl-acyl carrier protein thioesterase," *Nat Biotechnol.*, 17(6):593-597.

(56) References Cited

OTHER PUBLICATIONS

Falciatore et al.,(May 1999) "Transformation of Nonselectable Reporter Genes in Marine Diatoms," *Mar. Biotechnol.,* 1(3):239-251.
Frenz et al., (1989) "Hydrocarbon recovery by extraction with a biocompatible solvent from free and immobilized cultures of *Botryococcus braunii,*" *Enzyme Microb. Technol.,* 11:717-724.
Fromm et al., (Sep. 1985) "Expression of genes transferred into monocot and dicot plant cells by electroporation," *Proc. Natl. Acad. Sci. USA,* 82:5824 5828.
Ginalski et al.,(2003) "Detection of reliable and unexpected protein fold predictions using 3D-Jury," *Nucleic Acids Research,* 31(13): 3291-3292.
Giuffrida et al., (2004) "Formation and Hydrolysis of Triacylglycerol and Sterol Epoxides: Role of Unsaturated Triacylglycerol Peroxyl Radicals," *Free Radical Biology and & Medicine,* 37(1):104-114.
Gruber et al., (1991) "*Escherichia coli—Anacystis nidulans* Plasmid Shuttle Vectors Containing the $P_L$ Promoter from Bacteriophage Lambda," *Current Micro.* 22:15-19.
Gruber et al., (1996) "Expression of the *Volvox* gene encoding nitrate reductase: Mutation-dependent activation of cryptic splice sites and intron-enhanced gene expression from a cDNA," *Plant Molecular Biology,* 31(1):1-12.
Guo et al. (Jun. 22, 2004) "Protein tolerance to random amino acid change," *Proc. Natl. Acad. Sci. USA,* 101(25):9205-9210.
Hall et al., (1993) "Expression of a foreign gene in *Chlamydomonas reinhardtii,*" *Gene,* 124:75-81.
Hallmann et al., (Nov. 1994) "Reporter genes and highly regulated promoters as tools for transformation experiments in *Volvox carteri,*" *Proc. Natl. Acad. Sci. USA,* 91:11562-11566.
Hanley-Bowdoin et al., (Feb. 1987) "Chloroplast promoters," *TIBS,* 12:67-70.
Hawkins et al., (1999) "Expression of Human Growth Hormone by the Eukaryotic Alga, *Chlorella,*" *Current Microbiology,* 38:335-341.
Heise et al., (1994) "Factors Controlling Medium-Chain Fatty Acid Synthesis in Plastids From *Cuphea* Embryos," *Prog. Lipid Res.,* 33(1/2):87-95.
Hejazi et al., (Apr. 2004) "Milking of microalgae," *TRENDS in Biotechnology,* 22(4):189-194.
Hill et al.,(1998) "Functional Analysis of Conserved Histidines in ADP-Glucose Pyrophosphorylase from *Escherichia coli,*" *Biochem. Biophys. Res. Comm.,* 244(2):573-577.
Hillen et al., (1982) "Hydrocracking of the Oils of *Botryococcus braunii* to Transport Fuels," *Biotechnology and Bioengineering,* XXIV:193-205.
Hitz et al., (1994) "Cloning of a Higher-Plant Plastid ω-6 Fatty Acid Desaturase cDNA and Its Expression in a Cyanobacterium," *Plant Physiol.,*105(2):635-641.
Huang et al. (2006) "Expression of mercuric reductase from *Bacillus megaterium* MB1 in eukaryotic microalga *Chlorella* sp. DT: an approach for mercury phytoremediation," *Appl. Microbial. Biotechnol.* 72:197-205.
Inoue et al., (1994) "Analysis of Oil Derived From Liquefaction of *Botryococcus braunii,*" *Biomass Bioenergy,* 6(4):269-274).
Isbell et al., (Feb. 1994) "Acid-Catalyzed Condensation of Oleic Acid into Estolides and Polyestolides," *JAOCS,* 71(2):169-174.
Jakobiak et al. (Dec. 2004) "The Bacterial Paromomycin Resistance Gene, aphH, as a Dominant Selectable Marker in *Volvox carteri,*" *Protist,* 155(4):381-393.
Jarvis et al.(1991) "Transient expression of firefly luciferase in protoplasts of the green alga *Chlorella ellipsoidea,*" *Current Genetics,* 19:317-321.
Jha et al., (2006) "Cloning and functional expression of an acyl-ACP thioesterase FatB type from *Diploknema (Madhuca) butyracea* seeds in *Escherichia coli,*" *Plant Physiology and Biochemistry,* 44:645-655.
Jiang et al., (Apr. 2005) "The Actin Gene Promoter-driven bar as a Dominant Selectable Marker for Nuclear Transformation of *Dunaliella salina,*" *Acta Genetica Sinica,* 32(4):424-433.

Jones et al., (Mar. 1995) "Palmitoyl-Acyl Carrier Protein (ACP) Thioesterase and the Evolutionary Origin of Plant Acyl-ACP Thioesterases," *The Plant Cell,* 7:359-371.
Kalscheuer et al., (1999) "Establishment of a gene transfer system for *Rhodococcus opacus* PD630 based on electroporation and its application for recombinant biosynthesis of poly(3-hydroxyalkanoic acids)," *Applied and Environmental Microbiology,* 52:508-515.
Kang et al., (Jul. 2000) "The Regulation Activity of Chlorella Virus Gene 5' Upstream Sequence in *Escherichia coli* and Eucaryotic Algae," [English Abstract] *Chinese Journal of Biotechnology,* 16(4):6 pages.
Kang et al., (2004) "Genetic diversity in chlorella viruses flanking kcv, a gene that encodes a potassium ion channel protein," *Virology,* 326(1):150-159.
Kawasaki et al., (2004) "Immediate early genes expressed in chlorovirus infections," *Virology,*318(1):214-223.
Kim et al., (2002) Stable Integration and Functional Expression of Flounder Growth Hormone Gene in Transformed Microalga, *Chlorella ellipsoidea, Mar. Biotechnol.,* 4(1):63-73.
Kindle, (Feb. 1990) "High-frequency nuclear transformation of *Chlamydomonas reinhardtii,*" *Proc. Natl. Acad. Sci. USA,* 87(3): 1228-1232.
Klein et al., (1987) "High-velocity microprojectiles for delivering nucleic acids into living cells," *Nature* London 327(7):70-73.
Knauf, (Feb. 1987) "The application of genetic engineering to oilseed crops," *TIBTECH,* 5:40-47.
Knutzon et al., (Jul. 1999) "Lysophosphatidic Acid Acyltransferase from Coconut Endosperm Mediates the Insertion of Laurate at the sn-2 Position of Triacylglycerols in Laurie Rapeseed Oil and Can Increase Total Laurate Levels," *Plant Physiology,* 120:739-746.
Kojima et al., (1999) "Growth and Hydrocarbon Production of Microalga *Botryococcus braunii* in Bubble Column Photobioreactors," *Journal of Bioscience and Bioengineering,* 87(6):811-815.
Koksharova et al., (Feb. 2002) "Genetic tools for cyanobacteria," *Appl Microbiol Biotechnol* 58(2):123-137.
Krebbers et al., (1982) "The maize chloroplast genes for the β and ε subunits of the photosynthetic coupling factor $CF^1$ are fused," *Nucleic Acids Research,* 10(16):4985-5002.
La Scala et al., (Jan. 2002) "The Effect of Fatty Acid Composition on the Acrylation Kinetics of Epoxidized Triacylglycerols", *Journal of the American Oil Chemists' Society,* 79(1):59-63.
Lapidot et al., (May 2002) "Stable Chloroplast Transformation of the Unicellular Red Alga *Porphyridium* Species," *Plant Physiol.,* 129(1): 7-12.
Larson et al., (2002) "Acyl CoA profilesof transgenic plants that accumulate medium-chain fatty acids indicate inefficient storage lipid synthesis in developing oilseeds," *The Plant Journal,* 32(4):519-527.
Lumbreras et al., (1998) "Efficient foreign gene expression in *Chlamydomonas reinhardtii* mediated by an endogenous intron," *Plant Journal,* 14(4):441-447.
Manuell et al., (2007) "Robust expression of a bioactive mammalian protein in *Chlamydomonas* chloroplast," *Plant Biotechnol Journal,* 5:402-412.
Mayer et al., (Feb. 4, 2005) "A Structural Model of the Plant Acyl-Acyl Carrier Protein Thioesterase FatB Comprises Two Helix/ 4-Stranded Sheet Domains, the N-terminal Domain Containing Residues That Affect Specificity and the C-terminal Domain Containing Catalytic Residues," *The Journal of Biological Chemistry,* 280(5):3621-3627.
Mayer et al., (Jan. 3, 2007) "Identification of amino acid residues involved in substrate specificity of plant acyl-ACP thioesterases using a bioinformatics-guided approach," *BMC Plant Biology,* 7(1):1-11 pages.
Mayfield et al., (Jan. 21, 2003) "Expression and assembly of a fully active antibody in algae," *Proc. Natl. Acad. Sci. USA,* 100(2):438-442.
Mekhedov et al., (Feb. 2000) "Toward a Functional Catalog of the Plant Genome. A Survey of Genes for Lipid Biosynthesis," *Plant Physiology,* 122:389-401.
Mendes et al. (2003) "Supercritical carbon dioxide extraction of compounds with pharmaceutical importance from microalgae," *Inorganica Chimica Acta,* 356:328-334.

(56) References Cited

OTHER PUBLICATIONS

Metzger et al., (Jun. 2003) "Lycopanerols I-L, Four New Tetraterpenoid Ethers from *Botryococcus braunii*," *J Nat. Prod.*66(6):772-778.
Metzger et al., (2005) "*Botryococcus braunii*: a rich source for hydrocarbons and related ether lipids," *Appl Microbiol Biotechnol* 66:486-496.
Miao et al., (2004) "High yield bio-oil production from fast pyrolysis by metabolic controlling of *Chlorella protothecoides*," *Journal of Biotechnology*, 110:85-93.
Miao et al., (2006) "Biodiesel production from heterotrophic microalgal oil," *Biosource Technology*, 97:841-846.
Minowa et al., (1995) "Oil production from algal cells of *Dunaliella tertiolecta* by direct thermochemical liquefaction," *Fuel*, 74(12):1735-1738.
Mitra et al., (Oct. 14, 1994) "A Chlorella Virus Gene Promoter Functions as a Strong Promoter Both in Plants and Bacteria," *Biochemical Biophysical Research Communication*, 204(1): 187-194.
Mitra et al., (Oct. 1994) "The *Chlorella* virus adenine methyltransferase gene promoter is a strong promoter in plants," *Plant Mol. Biol.*, 26(1):85-93.
Moreno-Pérez et al., (2012) "Reduced expression of FatA thioesterases in Arabidopsis affects the oil content and fatty acid composition of the seeds," *Planta*, 235:629-639.
Mullet et al., (1985) "Multiple transcripts for higher plant rbcL and atpB genes and localization of the transcription initiation site of the rbcL gene," *Plant Molecular Biology*, 4:39-54.
Oda et al., (2000) "Degradation of Polylactide by Commercial Proteases," *Journal of Polymers and the Environment*, 8(1):29-32.
Onai et al., (2004) "Natural transformation of the thermophilic cyanobacterium *Thermosynechococcus elongatus* BP-1: a simple and efficient method for gene transfer," *Mol Genet Genomics*, 271(1):50-59.
Park et al., (2005) "Isolation and Characterization of Chlorella Virus from Fresh Water in Korea and Application in Chlorella Transformation System," *The Plant Pathololology Journal*, 21(1): 13-20.
Pröschold et al., (Aug. 2005) "Portrait of a species: *Chlamydomonas reinhardtii*," *Genetics*, 170:1601-1610.
Radakovits et al., (Apr. 2010) "Genetic Engineering of Algae for Enhanced Biofuel Production," *Eukaryotic Cell*, 9(4):486-501.
Rao et al., (2006) "Antioxidant Activity of *Botryococcus braunii* Extract Elucidated in Vitro Models," *J. Agric. Food Chem.*, 54(13):4593-4599.
Rehm et al., (2001)"Heterologous expression of the acyl-acyl carrier protein thioesterase gene from the plant *Umbellularia californica* mediates polyhydroxyalkanoate biosynthesis in recombinant *Escherichia coli*," *Appl Microbiol Biotechnol*, 55:205-209.
Rismani-Yazdi et al., (2011) "Transcriptome sequencing and annotation of the microalgae *Dunaliella tertiolecta*: Pathway description and gene discovery for production of next-generation biofuels," *BMC Genomics*, 12:148, 17 pages; doi:10.1186/1471-2164-12-148.
Rosenberg, Julian N. et al., (2008) "A green light for engineered algae: redirecting metabolism to fuel a biotechnology revolution," *Current Opinion in Biotechnology*, 19(5):430-436.
Salas et al., (Jul. 1, 2002) "Characterization of substrate specificity of plant FatA and FatB acyl-ACP thioesterases," *Archives of Biochemistry and Biophysics*, 403(1):25-34.
Sanford, (Dec. 1988) "The biolistic process," *Trends In Biotech.* 6:299-302.
Sawayama et al. (1999) Possibility of renewable energy production and $CO_2$ mitigation by thermochemical liquefaction of microalgae *Biomass and Bioenergy*, 17:33-39.
Schreier et al., (1985) "The use of nuclear-encoded sequences to direct the light-regulated synthesis and transport of a foreign protein into plant chloroplasts," *EMBO J.* 4(1):25-32.
Schultz et al., (Apr. 2005) "A common core of secondary structure of the internal transcribed spacer 2 (ITS2) throughout the Eukaryota," *RNA*, 11(4):361-364.

Schütt et al., (1998) "The role of acyl carrier protein isoforms from *Cuphea lanceolata* seeds in the de-novo biosynthesis of medium-chain fatty acids," *Publication, Planta*, 205:263-268.
Shao et al., (2002) "Cloning and expression of metallothionein mutant α-KKS-α in *Anabaena* sp. PCC 7120," *Marine Pollution Bulletin*,45(1-12):163-167.
Sheehan, John; Dunahay, Terri; Benemann, John; Roessler, Paul; (Jul. 1998) "A Look Back at the U.S. Department of Energy's Aquatic Species Program: Biodiesel from Algae," Prepared for U.S. Department of Energy's Office of Fuels Development, Prepared by *National Renewable Energy Laboratory*, NREL/TP-580-24190, 328 pages.
Stemmer et al., (1995) "Single-step assembly of a gene and entire plasmid from large numbers of oligodeoxyribonucleotides," *Gene*, 164(1):49-53.
Tan et al., (Aug. 2005) "Establishment of a Micro-Particle Bombardment Transformation System for *Dunaliella salina*," *The Journal of Microbiology*, 43(4):361-365.
Tang et al., (Aug. 1995) "Insertion Mutagenesis of *Chlamydomonas reinhardtii* by Electroporation and Heterologous DNA," *Biochemistry and Molecular Biology International*, 36(5): 1025-1035.
Tjellström et al. (Feb. 20, 2013) "Disruption of plastid acyl:acyl carrier protein synthetases increases medium chain fatty acid accumulation in seeds of transgenic Arabidopsis," *FEBS Letters*, 587(7):936-942.
Tyystjärvi et al., (2005) "Mathematical modelling of the light response curve of photoinhibition of Photosystem II," *Photosynthesis Research*, 84(1-3):21-27.
Vázquez-Bermúdez et al., (Jan. 2000) "Uptake of 2-Oxoglutarate in *Synechococcus* Strains Transformed with the *Escherichia coli* kgtP Gene," *Journal of Bacteriology*, 182(1):211-215.
Vázquez-Bermúdez et al., (2003) "Carbon supply and 2-oxoglutarate ejects on expression of nitrate reductase and nitrogen-regulated genes in *Synechococcus* sp. strain PCC 7942," *FEMS Microbiology Letters*, 221(2):155-159.
Voelker, (1996) "Plant Acyl-ACP Thioesterases: Chain-Length Determining Enzymes in Plant Fatty Acid Biosynthesis," *Genetic Engineering*, Edited by: Setlow JK. Plenum Pres, New York, 18:111-133.
Voelker et al., (Dec. 1994) "Alteration of the Specificity and Regulation of Fatty Acid Synthesis of *Escherichia coli* by Expression of a Plant Medium Chain Acyl-Acyl Carrier Protein Thioesterase," *Journal of Bacteriology*, 176(23):7320-7327.
Voelker et al., (1997) "Broad-Range and Binary-Range Acyl-Acyl-Carrier-Protein Thioesterases Suggest an Alternative Mechanism for Medium-Chain Production in Seeds,"*Plant Physiol.*, 114:669-677.
Voetz et al., (1994) "Three Different cDNAs Encoding Acyl Carrier Proteins from *Cuphea lanceolata*," *Plant Physiol.*, 106:785-786.
Walker et al., (2005) "Characterisation of the *Dunaliella tertiolecta* RbcS genes and their promoter activity in *Chlamydomonas reinhardtii*," *Plant Cell Rep.* 23(10-11):727-735.
Westphal et al., (Mar. 27, 2001) "Vipp1 deletion mutant of *Synechocystis*: A connection between bacterial phage shock and thylakoid biogenesis?" *Proc. Natl. Acad. Sci. USA*, 98(7):4243-4248.
Wiberg et al., (2000) "The distribution of caprylate, caprate and laurate in lipids from developing and mature seeds of transgenic *Brassica napus* L.," *Planta*, 212:33-40.
Wirth et al., (1989) "Transformation of various species of gram-negative bacteria belonging to 11 different genera by electroporation," *Mol Gen Genet.* 216(1):175-177.
Wolk et al., (Mar. 1984) "Construction of shuttle vectors capable of conjugative transfer from *Escherichia coli* to nitrogen-fixing filamentous cyanobacteria," *Proc. Natl. Acad. Sci. USA*, 81(5):1561-1565.
Wong et al., (1992) "*Arabidopsis thaliana* small subunit leader and transit peptide enhance the expression of *Bacillus thuringiensis* proteins in transgenic plants," *Plant Molecular Biology*, 20:81-93.
Wu et al., (2001) "Identification of *Chlorella* spp. isolates using ribosomal DNA sequences," *Bot. Bull. Acad. Sin.*42:115-121.
Yu et al., (2011) "Modifications of the metabolic pathways of lipid and triacylglycerol production in microalgae," *Microbial Cell Factories*, 10:91 [Retrieved from the Internet Jul. 24, 2012: <URL:http://www.microbialcellfactories.com/content/10/1/91>], 11 pages.

(56) References Cited

OTHER PUBLICATIONS

Yuan et al., (Nov. 1995) "Modification of the substrate specificity of an acyl-acyl carrier protein thioesterase by protein engineering," *Proc. Natl. Acad. Sci. USA*, 92:10639-10643.

Yuan et al., (Feb. 16, 1996) "The Catalytic Cysteine and Histidine in the Plant Acyl-Acyl Carrier Protein Thioesterases," *The Journal of Biological Chemistry*, 271(7):3417-3419.

Zurawski et al., (1981) "The structure of the gene for the large subunit of ribulose 1,5-bisphosphate carboxylase from spinach chloroplast DNA," *Nucleic Acids Res.* 9(14):3251-3270.

Zurawski et al., (Dec. 1982) "Nucleotide sequence of the gene for the $M_r$ 32,000 thylakoid membrane protein from *Spinacia oleracea* and *Nicotiana debneyi* predicts a totally conserved primary translation product of $M_r$ 38,950," *Proc. Natl. Acad. Sci. USA*, 79:7699-7703.

U.S. Office Action, dated Jul. 26, 2016, issued in U.S. Appl. No. 13/797,733.

U.S. Notice of Allowance, dated Sep. 21, 2016, issued in U.S. Appl. No. 13/797,733.

U.S. Office Action (Requirement for Restriction/Election), dated Jul. 12, 2016, issued in U.S. Appl. No. 14/167,908.

U.S. Office Action, dated Apr. 3, 2017, issued in U.S. Appl. No. 14/167,908.

U.S. Notice of Allowance, dated Jul. 10, 2017, issued in U.S. Appl. No. 14/167,908.

U.S. Notice of Allowance, dated Aug. 4, 2017, issued in U.S. Appl. No. 14/167,908.

U.S. Office Action (Requirement for Restriction/Election), dated Jul. 12, 2016, issued in U.S. Appl. No. 14/209,931.

U.S. Office Action, dated Jan. 26, 2017, issued in U.S. Appl. No. 14/209,931.

U.S. Notice of Allowance, dated May 15, 2017, issued in U.S. Appl. No. 14/209,931.

U.S. Notice of Allowance, dated Jun. 14, 2017, issued in U.S. Appl. No. 14/209,931.

U.S. Office Action, dated Jan. 19, 2017, issued in U.S. Appl. No. 14/808,361.

U.S. Notice of Allowance, dated Apr. 28, 2017, issued in U.S. Appl. No. 14/808,361.

Database Geneseq [Online] Jun. 15, 2007 (Jun. 15, 2007), "Medium chain-specific acyl-(ACP)-thioesterase CITEG1.", retrieved from EBI accession No. GSP:AAW06703 Database accession No. AAW06703.

Chinese First Office Action dated Jun. 13, 2017 issued in CN 201480018889.4.

European Examination Report dated Oct. 25, 2016 issued in EP 14 706 996.7.

European Second Office Action dated Jan. 4, 2018 issued in EP 14 706 996.7.

Australian First Office Action dated Aug. 14, 2017 issued in AU 2014236763.

European Partial Supplementary Search Report (Communication pursuant to Rule 164(1)EPC) dated Jul. 6, 2016 issued in EP 14 76 9502.7.

European Extended Search Report dated Oct. 13, 2016 issued in EP 14 76 9502.7.

European First Office Action dated Jul. 11, 2017 issued in EP 14769502.7.

European First Office Action dated Jan. 4, 2018 issued in EP 15747911.4.

Mexican First Office Action dated Jan. 26, 2018 issued in MX MX/A/2015/011507.

PCT International Preliminary Report on Patentability dated Feb. 2, 2017 issued in PCT/US2015/042044.

Dubois et al., (2007) "Fatty acid profiles of 80 vegetable oils with regard to their nutritional potential," *Eur. J. Lipid Sci. Technol.*, 109:710-732.

Mittendorf et al., (1999) "Polyhydroxyalkanoate synthesis in transgenic plants as a new tool to study carbon flow through β-oxidation," *The Plant Journal*, 20(1):45-55.

U.S. Appl. No. 15/809,973, filed Nov. 10, 2017, Davis.

U.S. Appl. No. 15/727,624, filed Oct. 8, 2017, Rudenko et al.

U.S. Appl. No. 15/684,941, filed Aug. 24, 2017, Davis et al.

Chinese Second Office Action dated Mar. 22, 2016 issued in CN 201280068060.6.

Brazilian First Office Action dated Mar. 7, 2018 issued in Application No. BR 1120150179207.

Chinese Second Office Action dated Mar. 5, 2018 issued in CN 201480018889.4.

Japanese First Office Action dated Mar. 29, 2018 issued in JP 2015-555436.

European Second Office Action [Examiner's Report] dated Mar. 5, 2018 issued in EP 14769502.7.

PCT International Preliminary Report on Patentability dated Mar. 30, 2017, issued in PCT/US2015/051042.

Chinese First Office Action dated Apr. 23, 2018 issued in CN 201480020002.5.

Australian Office Action dated Jun. 12, 2018, issued in AU 2014236763.

Jing F. et al., "Phylogenetic and experimental characterization of an acyl-ACP thioesterase family reveals significant diversity in enzymatic specificity and activity," BMC Biochemistry, 2011, 12:44.

U.S. Office Action, dated May 25, 2018, issued in U.S. Appl. No. 15/062,045.

U.S. Office Action, dated May 31, 2018, issued in U.S. Appl. No. 15/684,941.

Mexican Second Office Action dated Jun. 15, 2018 issued in MX MX/a/2015/011507.

European First Office Action dated Jun. 8, 2018 issued in EP 15775855.8.

ACYL-ACP THIOESTERASES AND MUTANTS THEREOF

CROSS-REFERENCE TO RELATED APPLICATIONS

This application claims the benefit under 35 U.S.C. § 119(e) of U.S. Provisional Application No. 62/052,440, filed on Sep. 18, 2014, and U.S. Provisional Application No. 62/075,168, filed on Nov. 4, 2014, both of which are hereby incorporated herein in their entireties.

SEQUENCE LISTING

The instant application contains a Sequence Listing which has been submitted electronically in ASCII format and is hereby incorporated by reference in its entirety. Said ASCII copy, created on Nov. 20, 2015, is named SOLAP0281412A01US_SL.txt and is 163,325 bytes in size.

BACKGROUND

Certain organisms including plants and some microalgae use a type II fatty acid biosynthetic pathway, characterized by the use of discrete, monofunctional enzymes for fatty acid synthesis. In contrast, mammals and fungi use a single, large, multifunctional protein.

Type II fatty acid biosynthesis typically involves extension of a growing acyl-ACP (acyl-carrier protein) chain by two carbon units followed by cleavage by an acyl-ACP thioesterase. In plants, two main classes of acyl-ACP thioesterases have been identified: (i) those encoded by genes of the FatA class, which tend to hydrolyze oleoyl-ACP into oleate (an 18:1 fatty acid) and ACP, and (ii) those encoded by genes of the FatB class, which liberate C8-C16 fatty acids from corresponding acyl-ACP molecules.

Different FatB genes from various plants have specificities for different acyl chain lengths. As a result, different gene products will produce different fatty acid profiles in plant seeds. See, U.S. Pat. Nos. 5,850,022; 5,723,761; 5,639,790; 5,807,893; 5,455,167; 5,654,495; 5,512,482; 5,298,421; 5,667,997; and 5,344,771; 5,304,481. Recently, FatB genes have been cloned into oleaginous microalgae to produce triglycerides with altered fatty acid profiles. See, WO2010/063032, WO2011/150411, WO2012/106560, and WO2013/158938.

SUMMARY

According to an embodiment, there is a nucleic acid construct comprising a polynucleotide sequence encoding a heterologous regulatory element and a FatB acyl-ACP thioesterase gene operable to produce an altered fatty acid profile in an oil produced by a cell expressing the nucleic acid construct. The FatB gene expresses a protein having an amino acid sequence having at least 65, 70, 80, 85, 86, 87, 88, 89, 90, 91, 92, 93, 94, 95, 96, 97, 98, or 99% identity to any of SEQ ID NOS: 1-18 or an amino acid sequence encoding a plastid targeting peptide fused upstream of any of SEQ ID NOS: 10-18.

Optionally, the acyl-ACP thioesterase coding sequence of the nucleic acid construct comprises at least 65, 70, 80, 85, 86, 87, 88, 89, 90, 91, 92, 93, 94, 95, 96, 97, 98, or 99% identity to any of SEQ ID NOS: 19-36 or any equivalent sequences by virtue of the degeneracy of the genetic code. In varying embodiments, the protein further comprises an alanine (A) at one or both positions corresponding to position 126 of SEQ ID NO: 61 (D124A) and 211 of SEQ ID NO: 61 (D209A).

In varying embodiments, the construct can have a plastid targeting peptide with at least 65, 70, 80, 85, 86, 87, 88, 89, 90, 91, 92, 93, 94, 95, 96, 97, 98, or 99% identity to SEQ ID NO: 37. In varying embodiments, the construct can have a plastid targeting peptide with at least 65, 70, 80, 85, 86, 87, 88, 89, 90, 91, 92, 93, 94, 95, 96, 97, 98, or 99% identity to SEQ ID NO: 40.

The FatB gene can express an active acyl-ACP-thioesterase protein having an amino acid sequence having:

(a) greater than 94.5, 94.6, 94.7, 94.8, 94.9, 95, or 95.1% identity to SEQ ID NO: 5;

(b) greater than 95.7, 95.8, 95.9, 96, 96.1 or 96.2% identity to SEQ ID NO: 14;

(c) greater than 95.4, 95.5, 95.6, 95.7, 95.8, 95.9, or 96% identity to SEQ ID NO: 3;

(d) greater than 94.5, 94.6, 94.7, 94.8, 94.9, 95, or 95.1% identity to SEQ ID NO: 12;

(e) greater than 94.8, 94.9, 95, 95.1, 95.2, 95.3, or 95.4% identity to SEQ ID NO: 1;

(f) greater than 95.9, 96.0, 96.1, 96.2, 96.3 or 96.4% identity to SEQ ID NO: 10;

(g) greater than 94.5, 94.6, 94.7, 94.8, 94.9, 95, or 95.1% identity to SEQ ID NO: 6;

(h) greater than 95.7, 95.8, 95.9, 96, 96.1 or 96.2% identity to SEQ ID NO: 15;

(i) greater than 94.5, 94.6, 94.7, 94.8, 94.9, 95, or 95.1% identity to SEQ ID NO: 4;

(j) greater than 95.7, 95.8, 95.9, 96, 96.1 or 96.2% identity to SEQ ID NO: 13;

(k) greater than 94.3, 94.4, 94.5, 94.6, 94.7, 94.8, or 94.9% identity to SEQ ID NO: 2;

(l) greater than 94.9, 95, 95.1, 95.2, 95.3, 95.4, or 95.5% identity to SEQ ID NO: 11;

(m) greater than 93.5, 93.6, 93.7, 93.8, 93.9, 94.0, or 94.1% identity to SEQ ID NO: 7;

(n) greater than 92.8, 92.9, 93.0, 93.1, 93.2, 93.3, or 93.4% identity to SEQ ID NO: 16;

(o) greater than 86.5, 86.6, 86.7, 86.8, 86.9, 87, or 87.1% identity to SEQ ID NO: 8;

(p) greater than 85.1, 85.2, 85.3, 85.4, 85.5, 85.6 or 85.7% identity to SEQ ID NO: 17;

(q) greater than 88, 88.1, 88.2, 88.3, 88.4, 88.5, or 88.6% identity to SEQ ID NO: 9; or (r) greater than 87.6, 87.7, 87.8, 87.9, 88, 88.1, or 88.2% identity to SEQ ID NO: 18.

In another embodiment, a host cell is capable of expressing the nucleic acid construct so as to produce a triglyceride oil having an altered composition relative to a control cell without the construct. Optionally the oil has an increase in C8-C12 fatty acids.

The host cell can be selected, without limitation, from a plant cell, a microbial cell, and a microalgal cell.

In a third embodiment, a recombinant host cell produces an altered fatty acid profile, using a method comprising transforming the host cell with the nucleic acid construct. The host cell can, without limitation, be a microbial cell, a plant cell, or a microalgal cell. In varying embodiments, the host cell expresses a nucleic acid encoding a protein having an alanine (A) at one or both positions corresponding to position 126 of SEQ ID NO: 61 (D124A) and 211 of SEQ ID NO: 61 (D209A), and produces at least 2-fold the amount of C18:0 and/or C18:1 fatty acids compared to a host cell that expresses the wild-type protein.

In a fourth embodiment, a method produces an oil or oil-derived product, by cultivating a host cell as mentioned above and extracting the oil produced. Optionally, the cultivation is by heterotrophic growth on sugar. Optionally, the method also includes producing a fatty acid, fuel, chemical, food, or other oil-derived product from the oil. Optionally, an oil is produced having a fatty acid profile comprising at least 20% C8, C10, C12, C14, C16 or C18 (e.g., C18:0 and/or C18:1) fatty acids. Where the oil is produced by a microalgae, the oil can have a microalgal sterol profile and optionally lack C24-alpha sterols. The oil can be used to produce an oil-derived product, optionally a fatty acid, fuel, chemical, food, or other oil-derived product from the oil produced by the above method.

In a fifth embodiment, there is a method for producing an oil. The method includes providing a plastidic, oleaginous cell, optionally a microbial cell expressing a functional, acyl-ACP thioesterase gene encoded by a FATB gene having a deletion mutation in a region corresponding to the region coding for amino acids 66-98 of SEQ ID NO: 8. cultivating the cell to produce a cell-oil, and isolating the cell-oil from the cell. The cell-oil can be enriched in C12 due to the deletion. The FATB gene can encode a protein with at least 65, 70, 80, 85, 86, 87, 88, 89, 90, 91, 92, 93, 94, 95, 96, 97, 98, or 99% sequence identity to SEQ ID NOS: 40 to 43. The FATB gene can have least 65, 70, 80, 85, 86, 87, 88, 89, 90, 91, 92, 93, 94, 95, 96, 97, 98, or 99% sequence identity to SEQ ID NOS: 44 or 45 or equivalent sequence by virtue of the degeneracy of the genetic code.

In a sixth embodiment, a cDNA, gene, expression cassette or host cell comprising a polynucleotide encoding a FATB protein having at least 65, 70, 80, 85, 86, 87, 88, 89, 90, 91, 92, 93, 94, 95, 96, 97, 98, or 99% sequence identity to any of SEQ ID NOS: 40 to 43.

In a seventh embodiment, a cDNA, gene, expression cassette or host cell comprises a polynucleotide having at least 65, 70, 80, 85, 86, 87, 88, 89, 90, 91, 92, 93, 94, 95, 96, 97, 98, or 99% sequence identity to SEQ ID NOS 44 or 45, or equivalent sequence by virtue of the degeneracy of the genetic code.

In an eight embodiment, a method of genetically engineering a cell includes expressing in the cell, a polynucleotide that encodes a protein having at least 65, 70, 80, 85, 86, 87, 88, 89, 90, 91, 92, 93, 94, 95, 96, 97, 98, or 99% sequence identity to any of SEQ ID NOS: 40 to 43; or has at least 65, 70, 80, 85, 86, 87, 88, 89, 90, 91, 92, 93, 94, 95, 96, 97, 98, or 99% sequence identity to SEQ ID NOS: 47 or 48, or equivalent sequence by virtue of the degeneracy of the genetic code.

In a further aspect, provided is a cDNA, gene, expression cassette or host cell comprising a polynucleotide encoding a FATA protein having at least 65, 70, 80, 85, 86, 87, 88, 89, 90, 91, 92, 93, 94, 95, 96, 97, 98, or 99% sequence identity to SEQ ID NO:61 and wherein the protein has an alanine (A) at one or both positions corresponding to position 126 of SEQ ID NO: 61 (D124A) and 211 of SEQ ID NO: 61 (D209A). In a further aspect, provided is a cDNA, gene, expression cassette or host cell comprising a polynucleotide encoding a FATA protein having at least 65, 70, 80, 85, 86, 87, 88, 89, 90, 91, 92, 93, 94, 95, 96, 97, 98, or 99% sequence identity to SEQ ID NO:61, or equivalent sequence by virtue of the degeneracy of the genetic code and wherein the protein has an alanine (A) at one or both positions corresponding to position 126 of SEQ ID NO: 61 (D124A) and 211 of SEQ ID NO: 61 (D209A). In a further aspect, provided is a method of genetically engineering a cell comprising expressing in the cell, a polynucleotide that (a) encodes a protein having at least 65, 70, 80, 85, 86, 87, 88, 89, 90, 91, 92, 93, 94, 95, 96, 97, 98, or 99% sequence identity to SEQ ID NO:61, wherein the protein has an alanine (A) at one or both positions corresponding to position 126 of SEQ ID NO: 61 (D124A) and 211 of SEQ ID NO: 61 (D209A).

In a further aspect, provided is a host cell capable of expressing the nucleic acid construct encoding a FATA protein having at least 65, 70, 80, 85, 86, 87, 88, 89, 90, 91, 92, 93, 94, 95, 96, 97, 98, or 99% sequence identity to SEQ ID NO:61 and wherein the protein has an alanine (A) at one or both positions corresponding to position 126 of SEQ ID NO: 61 (D124A) and 211 of SEQ ID NO: 61 (D209A) so as to produce a triglyceride oil having an altered composition relative to a control cell without the construct, the oil optionally having an increase in C18 fatty acids, including C18:0 and C18:1 fatty acids. In varying embodiments, the host cell is selected from a plant cell, a microbial cell, and a microalgal cell. In a further aspect, provided is a method of producing a recombinant cell that produces an altered fatty acid profile, the method comprising transforming the cell with a nucleic acid encoding a FATA protein having at least 65, 70, 80, 85, 86, 87, 88, 89, 90, 91, 92, 93, 94, 95, 96, 97, 98, or 99% sequence identity to SEQ ID NO:61 and wherein the protein has an alanine (A) at one or both positions corresponding to position 126 of SEQ ID NO: 61 (D124A) and 211 of SEQ ID NO: 61 (D209A). In a further aspect, provided is a host cell produced according to such a method. In some embodiments, the host cell is selected from a plant cell, a microbial cell, and a microalgal cell. In a further aspect, provided is a method for producing an oil or oil-derived product, the method comprising cultivating a host cell encoding a FATA protein having at least 65, 70, 80, 85, 86, 87, 88, 89, 90, 91, 92, 93, 94, 95, 96, 97, 98, or 99% sequence identity to SEQ ID NO:61 and wherein the protein has an alanine (A) at one or both positions corresponding to position 126 of SEQ ID NO: 61 (D124A) and 211 of SEQ ID NO: 61 (D209A) and extracting oil produced thereby, optionally wherein the cultivation is by heterotrophic growth on sugar. In varying embodiments, the methods further comprise producing a fatty acid, fuel, chemical, food, or other oil-derived product from the oil. In varying embodiments, the host cell produces at least 2-fold the amount of C18:0 and/or C18:1 fatty acids compared to a host cell that expresses the wild-type protein. In a further aspect, further provided is an oil produced by the method of expressing in a host cell a polynucleotide encoding a FATA protein having at least 65, 70, 80, 85, 86, 87, 88, 89, 90, 91, 92, 93, 94, 95, 96, 97, 98, or 99% sequence identity to SEQ ID NO:61 and wherein the protein has an alanine (A) at one or both positions corresponding to position 126 of SEQ ID NO: 61 (D124A) and 211 of SEQ ID NO: 61 (D209A), optionally having a fatty acid profile comprising at least 20% C8, C10, C12, C14, C16 or C18 (e.g., C18:0 and/or C18:1) fatty acids. In varying embodiments, the oil is produced by a microalgae, has a microalgal sterol profile, and/or optionally, lacks C24-alpha sterols. Further provided is an oil-derived product, optionally a fatty acid, fuel, chemical, food, or other oil-derived product from the oil produced by the method of expressing in a host cell a polynucleotide encoding a FATA protein having at least 65, 70, 80, 85, 86, 87, 88, 89, 90, 91, 92, 93, 94, 95, 96, 97, 98, or 99% sequence identity to SEQ ID NO:61 and wherein the protein has an alanine (A) at one or both positions corresponding to position 126 of SEQ ID NO: 61 (D124A) and 211 of SEQ ID NO: 61 (D209A).

DESCRIPTION OF ILLUSTRATIVE EMBODIMENTS

Definitions

As used with respect to nucleic acids, the term "isolated" refers to a nucleic acid that is free of at least one other component that is typically present with the naturally occurring nucleic acid. Thus, a naturally occurring nucleic acid is isolated if it has been purified away from at least one other component that occurs naturally with the nucleic acid.

A "cell oil" or "natural fat" shall mean a predominantly triglyceride oil obtained from an organism, where the oil has not undergone blending with another natural or synthetic oil, or fractionation so as to substantially alter the fatty acid profile of the triglyceride. In connection with an oil comprising triglycerides of a particular regiospecificity, the cell oil or natural fat has not been subjected to interesterification or other synthetic process to obtain that regiospecific triglyceride profile, rather the regiospecificity is produced naturally, by a cell or population of cells. In connection with a cell oil or natural fat, and as used generally throughout the present disclosure, the terms oil and fat are used interchangeably, except where otherwise noted. Thus, an "oil" or a "fat" can be liquid, solid, or partially solid at room temperature, depending on the makeup of the substance and other conditions. Here, the term "fractionation" means removing material from the oil in a way that changes its fatty acid profile relative to the profile produced by the organism, however accomplished. The terms "cell oil" and "natural fat" encompass such oils obtained from an organism, where the oil has undergone minimal processing, including refining, bleaching and/or degumming, which does not substantially change its triglyceride profile. A cell oil can also be a "noninteresterified cell oil", which means that the cell oil has not undergone a process in which fatty acids have been redistributed in their acyl linkages to glycerol and remain essentially in the same configuration as when recovered from the organism.

"Exogenous gene" shall mean a nucleic acid that codes for the expression of an RNA and/or protein that has been introduced into a cell (e.g. by transformation/transfection), and is also referred to as a "transgene". A cell comprising an exogenous gene may be referred to as a recombinant cell, into which additional exogenous gene(s) may be introduced. The exogenous gene may be from a different species (and so heterologous), or from the same species (and so homologous), relative to the cell being transformed. Thus, an exogenous gene can include a homologous gene that occupies a different location in the genome of the cell or is under different control, relative to the endogenous copy of the gene. An exogenous gene may be present in more than one copy in the cell. An exogenous gene may be maintained in a cell, for example, as an insertion into the genome (nuclear or plastid) or as an episomal molecule.

"Fatty acids" shall mean free fatty acids, fatty acid salts, or fatty acyl moieties in a glycerolipid. It will be understood that fatty acyl groups of glycerolipids can be described in terms of the carboxylic acid or anion of a carboxylic acid that is produced when the triglyceride is hydrolyzed or saponified.

"Microalgae" are microbial organisms that contain a chloroplast or other plastid, and optionally that are capable of performing photosynthesis, or a prokaryotic microbial organism capable of performing photosynthesis. Microalgae include obligate photoautotrophs, which cannot metabolize a fixed carbon source as energy, as well as heterotrophs, which can live solely off of a fixed carbon source. Microalgae include unicellular organisms that separate from sister cells shortly after cell division, such as *Chlamydomonas*, as well as microbes such as, for example, Volvox, which is a simple multicellular photosynthetic microbe of two distinct cell types. Microalgae include cells such as *Chlorella*, *Dunaliella*, and *Prototheca*. Microalgae also include other microbial photosynthetic organisms that exhibit cell-cell adhesion, such as *Agmenellum, Anabaena*, and *Pyrobotrys*. Microalgae also include obligate heterotrophic microorganisms that have lost the ability to perform photosynthesis, such as certain dinoflagellate algae species and species of the genus *Prototheca*.

An "oleaginous" cell is a cell capable of producing at least 20% lipid by dry cell weight, naturally or through recombinant or classical strain improvement. An "oleaginous microbe" or "oleaginous microorganism" is a microbe, including a microalga that is oleaginous.

The term "percent sequence identity," in the context of two or more amino acid or nucleic acid sequences, refers to two or more sequences or subsequences that are the same or have a specified percentage of amino acid residues or nucleotides that are the same, when compared and aligned for maximum correspondence, as measured using a sequence comparison algorithm or by visual inspection. For sequence comparison to determine percent nucleotide or amino acid identity, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted using the NCBI BLAST software (ncbi.nlm.nih.gov/BLAST/) set to default parameters. For example, to compare two nucleic acid sequences, one may use blastn with the "BLAST 2 Sequences" tool Version 2.0.12 (Apr. 21, 2000) set at the following default parameters: Matrix: BLOSUM62; Reward for match: 1; Penalty for mismatch: −2; Open Gap: 5 and Extension Gap: 2 penalties; Gap x drop-off: 50; Expect: 10; Word Size: 11; Filter: on. For a pairwise comparison of two amino acid sequences, one may use the "BLAST 2 Sequences" tool Version 2.0.12 (Apr. 21, 2000) with blastp set, for example, at the following default parameters: Matrix: BLOSUM62; Open Gap: 11 and Extension Gap: 1 penalties; Gap x drop-off 50; Expect: 10; Word Size: 3; Filter: on.

Numbering of a given amino acid polymer or nucleic acid polymer "corresponds to" or is "relative to" the numbering of a selected amino acid polymer or nucleic acid polymer when the position of any given polymer component (e.g., amino acid, nucleotide, also referred to generically as a "residue") is designated by reference to the same or to an equivalent position (e.g., based on an optimal alignment or a consensus sequence) in the selected amino acid or nucleic acid polymer, rather than by the actual numerical position of the component in the given polymer.

A "variant" is a polypeptide comprising a sequence which differs in one or more amino acid position(s) from that of a parent polypeptide sequence (e.g., by substitution, deletion, or insertion). A variant may comprise a sequence which differs from the parent polypeptides sequence in up to 40% of the total number of residues of the parent polypeptide sequence, such as in up to 40%, 35%, 30%, 25%, 20%, 15%, 10%, 9%, 8%, 7%, 6%, 5%, 4%, 3% 2% or 1% of the total number of residues of the parent polypeptide sequence. For example, a variant of a 400 amino acid polypeptide sequence comprises a sequence which differs in up to 40% of the total number of residues of the parent polypeptide sequence, that is, in up to 160 amino acid positions within the 400 amino acid polypeptide sequence (such as in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 78, 79, 80, 85, 90, 95, 100, 105, 110, 115, 120, 125, 130, 135, 140, 145, 150, 155, or 160 amino acid positions within the reference sequence.

"Naturally occurring" as applied to a composition that can be found in nature as distinct from being artificially produced by man. For example, a polypeptide or polynucleotide that is present in an organism (including viruses, bacteria, protozoa, insects, plants or mammalian tissue) that can be isolated from a source in nature and which has not been intentionally modified by man in the laboratory is naturally occurring. "Non-naturally occurring" (also termed "synthetic" or "artificial") as applied to an object means that the object is not naturally-occurring—i.e., the object cannot be found in nature as distinct from being artificially produced by man.

In connection with a cell oil, a "profile" is the distribution of particular species or triglycerides or fatty acyl groups within the oil. A "fatty acid profile" is the distribution of fatty acyl groups in the triglycerides of the oil without reference to attachment to a glycerol backbone. Fatty acid profiles are typically determined by conversion to a fatty acid methyl ester (FAME), followed by gas chromatography (GC) analysis with flame ionization detection (FID). The fatty acid profile can be expressed as one or more percent of a fatty acid in the total fatty acid signal determined from the area under the curve for that fatty acid. FAME-GC-FID measurement approximate weight percentages of the fatty acids.

As used herein, an oil is said to be "enriched" in one or more particular fatty acids if there is at least a 10% increase in the mass of that fatty acid in the oil relative to the non-enriched oil. For example, in the case of a cell expressing a heterologous FatB gene described herein, the oil produced by the cell is said to be enriched in, e.g., C8 and C16 fatty acids if the mass of these fatty acids in the oil is at least 10% greater than in oil produced by a cell of the same type that does not express the heterologous FatB gene (e.g., wild type oil).

"Recombinant" is a cell, nucleic acid, protein or vector that has been modified due to the introduction of an exogenous nucleic acid or the alteration of a native nucleic acid. Thus, e.g., recombinant (host) cells can express genes that are not found within the native (non-recombinant) form of the cell or express native genes differently than those genes are expressed by a non-recombinant cell. Recombinant cells can, without limitation, include recombinant nucleic acids that encode a gene product or suppression elements such as mutations, knockouts, antisense, interfering RNA (RNAi) or dsRNA that reduce the levels of active gene product in a cell. A "recombinant nucleic acid" is a nucleic acid originally formed in vitro, in general, by the manipulation of nucleic acid, e.g., using polymerases, ligases, exonucleases, and endonucleases, using chemical synthesis, or otherwise in a form not normally found in nature. Recombinant nucleic acids may be produced, for example, to place two or more nucleic acids in operable linkage. Thus, an isolated nucleic acid or an expression vector formed in vitro by nucleic by ligating DNA molecules that are not normally joined in nature, are both considered recombinant herein. Recombinant nucleic acids can also be produced in other ways; e.g., using chemical DNA synthesis. Once a recombinant nucleic acid is made and introduced into a host cell or organism, it may replicate using the in vivo cellular machinery of the host cell; however, such nucleic acids, once produced recombinantly, although subsequently replicated intracellularly, are still considered recombinant herein. Similarly, a "recombinant protein" is a protein made using recombinant techniques, i.e., through the expression of a recombinant nucleic acid.

Embodiments relate to the use of novel FatB acyl-ACP thioesterase genes (e.g. in the form of cDNA, vectors, and constructs in vitro or in host cells) gene-variants, and peptides isolated from plants which can be expressed in a host cell in order to alter the fatty acid profile of an oil produced by the cell. The genes were discovered by obtaining cDNA from various plant species and transforming a model organism—the obligate heterotrophic microalga, *Prototheca moriformis*. Although *P. moriformis* was used to screen the FatB genes for ability to the alter fatty acid profile, the genes and corresponding gene-products are useful in a wide variety of host cells. For example, the genes can be expressed in bacteria, other microalgae, or higher plants. The genes can be expressed in higher plants according to the methods of U.S. Pat. Nos. 5,850,022; 5,723,761; 5,639,790; 5,807,893; 5,455,167; 5,654,495; 5,512,482; 5,298,421; 5,667,997; 5,344,771; and 5,304,481. The fatty acids can be further converted to triglycerides, fatty aldehydes, fatty alcohols and other oleochemicals either synthetically or biosynthetically.

Additionally, in the course of obtaining the novel FatB sequences, we discovered that certain N-terminal deletions in the FatB cDNAs led to desirably altered fatty acid profiles in the microalgal model.

In an embodiment, there is a polynucleotide comprising a nucleic acid sequence operably linked to a heterologous expression control sequence, wherein said nucleic acid sequence is selected from the group consisting of SEQ ID NOs: 19-36, a sequence encoding the amino acid sequence of the group consisting of SEQ ID NOs: 1-18, or a variant thereof with acyl-ACP thioesterase activity when expressed in a plastidic oleaginous cell.

In an embodiment, triglycerides are produced by a host cell expressing a novel FatB gene of Table 1. A triglyceride-containing cell oil can be recovered from the host cell. The cell oil can be refined, degummed, bleached and/or deodorized. The oil, in its natural or processed form, can be used for foods, chemicals, fuels, cosmetics, plastics, and other uses.

The genes can be used in a variety of genetic constructs including plasmids or other vectors for expression or recombination in a host cell. The genes can be codon optimized for expression in a target host cell (e.g., using the codon usage tables of Tables 2-5.) For example, at least 60, 65, 70, 75, 80, 85, 90, 95 or 100% of the codons used can be the most preferred codon according to Table 2, 3, 4 or 5. Alternately, at least 60, 65, 70, 75, 80, 85, 90, 95 or 100% of the codons used can be the first or second most preferred codon according to Table 2, 3, or 5. The proteins produced by the genes can be used in vivo or in purified form.

For example, the gene can be prepared in an expression vector comprising an operably linked promoter and 5'UTR. Where a plastidic cell is used as the host, a suitably active plastid targeting peptide (also "transit peptide") can be fused to the FATB gene, as in the examples below. Transit peptides are denoted by underlined or outlined text in some of the FATB peptide sequences that appear below. Generally, for the newly identified FATB genes, there are roughly 50 amino acids at the N-terminal that constitute a plastid transit peptide, which are responsible for transporting the enzyme to the chloroplast. In the examples below, this transit peptide is replaced with a 38 amino acid sequence (SEQ ID NO: 37) that is effective in *Prototheca moriformis* host cells for transporting the enzyme to the plastids of those cells. Thus, we contemplate deletions and fusion proteins in order to optimize enzyme activity in a given host cell. For example, a transit peptide from the host or related species may be used instead of that of the newly discovered plant genes described here. In general, plastid targeting peptides are less conserved than the enzymatic domains of FATB genes. Plastid targeting peptides can be substituted with other sequences such as those found in plant-derived sequences of plastid targeting genes (e.g., those for FATA, FATB, SAD or KAS genes) in the ThYme database of thioesters-active enzymes hosted by Iowa State University/NSF Engineering Research Center for Biorenewable Chemicals. Accordingly, certain embodiments describe percent identity to gene or protein sequences to FATB genes lacking the plastid targeting peptide.

A selectable marker gene may be included in the vector to assist in isolating a transformed cell. Examples of selectable markers useful in microalgae include sucrose invertase, antibiotic resistance, and thiamine synthesis genes.

The gene sequences disclosed can also be used to prepare antisense, or inhibitory RNA (e.g., RNAi or hairpin RNA) to inhibit complementary genes in a plant or other organism.

FatB genes found to be useful in producing desired fatty acid profiles in a cell are summarized below in Table 1. Nucleic acids or proteins having the sequence of SEQ ID NOS: 19-36 can be used to alter the fatty acid profile of a recombinant cell. Variant nucleic acids can also be used; e.g., variants having at least 65, 70, 80, 85, 86, 87, 88, 89, 90, 91, 92, 93, 94, 95, 96, 97, 98, or 99% sequence identity to SEQ ID NOS: 19-36. Codon optimization of the genes for a variety of host organisms is contemplated, as is the use of gene fragments. Preferred codons for *Prototheca* strains and for *Chlorella protothecoides* are shown below in Tables 2 and 3, respectively. Codon usage for *Cuphea wrightii* is shown in Table 4. Codon usage for *Arabidopsis* is shown in Table 5; for example, the most preferred of codon for each amino acid can be selected. Codon tables for other organisms including microalgae and higher plants are known in the art. In some embodiments, the first and/or second most preferred *Prototheca* codons are employed for codon optimization. In specific embodiments, the novel amino acid sequences contained in the sequence listings below are converted into nucleic acid sequences according to the preferred codon usage in *Prototheca, Chlorella, Cuphea wrightii*, or *Arabidopsis* as set forth in tables 2 through 5 or nucleic acid sequences having at least 65, 70, 80, 85, 86, 87, 88, 89, 90, 91, 92, 93, 94, 95, 96, 97, 98, or 99% sequence identity to these derived nucleic acid sequences.

In embodiments, there is protein or a nucleic acid encoding a protein having any of SEQ ID NOS: 1-18. In an embodiment, there is protein or a nucleic acid encoding a protein having at least 80, 85, 85.1, 85.2, 85.3, 85.4, 85.5, 86, 86.5, 86.6, 86.7, 87, 87.5, 87.6, 87.7, 87.8, 87.9, 88, 89, 90, 91, 92, 92.5, 92.6, 92.7, 92.8, 92.9, 93, 93.5, 93.6, 93.7, 93.8, 94, 94.1, 94.2, 94.3, 94.4, 94.5, 94.6, 94.7, 94.8, 94.9, 95, 95.1, 95.2, 95.3, 95.4, 95.6, 95.7, 95.8, 95.9, 96, 96.1, 96.2, 96.3, 96.4, 96.5, 97, 98, 99, or 100% sequence identity with any of SEQ ID NOS: 1-18. An embodiment comprises a fragment of any of the above-described proteins or nucleic acids (including fragments of protein or nucleic acid variants), wherein the protein fragment has acyl-ACP thioesterase activity or the nucleic acid fragment encodes such a protein fragment. In other embodiments, the fragment includes a domain of an acyl-ACP thioesterase that mediates a particular function, e.g., a specificity-determining domain. Illustrative fragments can be produced by C-terminal and/or N-terminal truncations and include at least 50%, 55%, 60%, 65%, 70%, 75%, 80%, 85%, 90%, 95%, 96%, 97%, 98%, or 99% of the full-length sequences disclosed herein.

In certain embodiments, percent sequence identity for variants of the nucleic acids or proteins discussed above can be calculated by using the full-length nucleic acid sequence (e.g., one of SEQ ID NOS: 19-36) or full-length amino acid sequence (e.g., one of SEQ ID NOS: 1-18) as the reference sequence and comparing the full-length test sequence to this reference sequence. In some embodiments relating to fragments, percent sequence identity for variants of nucleic acid or protein fragments can be calculated over the entire length of the fragment.

The nucleic acids can be in isolated form, or part of a vector or other construct, chromosome or host cell. It has been found that is many cases the full length gene (and protein) is not needed; for example, deletion of some or all of the N-terminal hydrophobic domain (typically an 18 amino acid domain starting with LPDW (SEQ ID NO: 62)) yields a still-functional gene. In addition, fusions of the specificity determining regions of the genes in Table 1 with catalytic domains of other acyl-ACP thioesterases can yield functional genes. Certain embodiments encompass functional fragments (e.g., specificity determining regions) of the disclosed nucleic acid or amino acids fused to heterologous acyl-ACP thioesterase nucleic acid or amino acid sequences, respectively.

TABLE 1

FatB genes and proteins according to embodiments

| GENE (species, abbreviation) | Amino acid sequence SEQ ID NO: | Amino acid sequence (without targeting peptide) | Native plant nucleic acid sequence | Plant nucleic acid sequence codon-optimized for *Prototheca moriformis* |
|---|---|---|---|---|
| *Cuphea crassiflora* (CcrasFATB1) | 1 | 10 | 19 | 28 |
| *Cuphea koehneana* (CkoeFATB3) | 2 | 11 | 20 | 29 |
| *Cuphea leptopoda* (CleptFATB1) | 3 | 12 | 21 | 30 |

TABLE 1-continued

FatB genes and proteins according to embodiments

| GENE (species, abbreviation) | Amino acid sequence SEQ ID NO: | Amino acid sequence (without targeting peptide) | Native plant nucleic acid sequence | Plant nucleic acid sequence codon-optimized for Prototheca moriformis |
|---|---|---|---|---|
| Cuphea angustifolia (CangFATB1) | 4 | 13 | 22 | 31 |
| Cuphea llavea (CllaFATB1) | 5 | 14 | 23 | 32 |
| Cuphea lophostoma (ClopFATB1) | 6 | 15 | 24 | 33 |
| Sassafras albidum FATB1(SalFATB1) | 7 | 16 | 25 | 34 |
| Sassafras albidum FATB2 (SalFATB2) | 8 | 17 | 26 | 35 |
| Lindera benzoin FATB1 (LbeFATB1) | 9 | 18 | 27 | 36 |

TABLE 2

Preferred codon usage in Prototheca strains

| Ala | GCG | 345 (0.36) |
| | GCA | 66 (0.07) |
| | GCT | 101 (0.11) |
| | GCC | 442 (0.46) |
| Cys | TGT | 12 (0.10) |
| | TGC | 105 (0.90) |
| Asp | GAT | 43 (0.12) |
| | GAC | 316 (0.88) |
| Glu | GAG | 377 (0.96) |
| | GAA | 14 (0.04) |
| Phe | TTT | 89 (0.29) |
| | TTC | 216 (0.71) |
| Gly | GGG | 92 (0.12) |
| | GGA | 56 (0.07) |
| | GGT | 76 (0.10) |
| | GGC | 559 (0.71) |
| His | CAT | 42 (0.21) |
| | CAC | 154 (0.79) |
| Ile | ATA | 4 (0.01) |
| | ATT | 30 (0.08) |
| | ATC | 338 (0.91) |
| Lys | AAG | 284 (0.98) |
| | AAA | 7 (0.02) |
| Leu | TTG | 26 (0.04) |
| | TTA | 3 (0.00) |
| | CTG | 447 (0.61) |
| | CTA | 20 (0.03) |
| | CTT | 45 (0.06) |
| | CTC | 190 (0.26) |
| Met | ATG | 191 (1.00) |
| Asn | AAT | 8 (0.04) |
| | AAC | 201 (0.96) |
| Pro | CCG | 161 (0.29) |
| | CCA | 49 (0.09) |
| | CCT | 71 (0.13) |
| | CCC | 267 (0.49) |
| Gln | CAG | 226 (0.82) |
| | CAA | 48 (0.18) |

TABLE 2-continued

Preferred codon usage in Prototheca strains

| Arg | AGG | 33 (0.06) |
| | AGA | 14 (0.02) |
| | CGG | 102 (0.18) |
| | CGA | 49 (0.08) |
| | CGT | 51 (0.09) |
| | CGC | 331 (0.57) |
| Ser | AGT | 16 (0.03) |
| | AGC | 123 (0.22) |
| | TCG | 152 (0.28) |
| | TCA | 31 (0.06) |
| | TCT | 55 (0.10) |
| | TCC | 173 (0.31) |
| Thr | ACG | 184 (0.38) |
| | ACA | 24 (0.05) |
| | ACT | 21 (0.05) |
| | ACC | 249 (0.52) |
| Val | GTG | 308 (0.50) |
| | GTA | 9 (0.01) |
| | GTT | 35 (0.06) |
| | GTC | 262 (0.43) |
| Trp | TGG | 107 (1.00) |
| Tyr | TAT | 10 (0.05) |
| | TAC | 180 (0.95) |
| Stop | | TGA/TAG/TAA |

TABLE 3

Preferred codon usage in Chlorella protothecoides

| TTC (Phe) | TAC (Tyr) | TGC (Cys) | TGA (Stop) |
| TGG (Trp) | CCC (Pro) | CAC (His) | CGC (Arg) |
| CTG (Leu) | CAG (Gln) | ATC (Ile) | ACC (Thr) |
| GAC (Asp) | TCC (Ser) | ATG (Met) | AAG (Lys) |
| GCC (Ala) | AAC (Asn) | GGC (Gly) | GTG (Val) |
| GAG (Glu) | | | |

TABLE 4

Codon usage for *Cuphea wrightii* (codon, amino acid, frequency, per thousand, number)

| | | | |
|---|---|---|---|
| UUU F 0.48 19.5 (52) | UCU S 0.21 19.5 (52) | UAU Y 0.45 6.4 (17) | UGU C 0.41 10.5 (28) |
| UUC F 0.52 21.3 (57) | UCC S 0.26 23.6 (63) | UAC Y 0.55 7.9 (21) | UGC C 0.59 15.0 (40) |
| UUA L 0.07 5.2 (14) | UCA S 0.18 16.8 (45) | UAA * 0.33 0.7 (2) | UGA * 0.33 0.7 (2) |
| UUG L 0.19 14.6 (39) | UCG S 0.11 9.7 (26) | UAG * 0.33 0.7 (2) | UGG W 1.00 15.4 (41) |
| CUU L 0.27 21.0 (56) | CCU P 0.48 21.7 (58) | CAU H 0.60 11.2 (30) | CGU R 0.09 5.6 (15) |
| CUC L 0.22 17.2 (46) | CCC P 0.16 7.1 (19) | CAC H 0.40 7.5 (20) | CGC R 0.13 7.9 (21) |
| CUA L 0.13 10.1 (27) | CCA P 0.21 9.7 (26) | CAA Q 0.31 8.6 (23) | CGA R 0.11 6.7 (18) |
| CUG L 0.12 9.7 (26) | CCG P 0.16 7.1 (19) | CAG Q 0.69 19.5 (52) | CGG R 0.16 9.4 (25) |
| AUU I 0.44 22.8 (61) | ACU T 0.33 16.8 (45) | AAU N 0.66 31.4 (84) | AGU S 0.18 16.1 (43) |
| AUC I 0.29 15.4 (41) | ACC T 0.27 13.9 (37) | AAC N 0.34 16.5 (44) | AGC S 0.07 6.0 (16) |
| AUA I 0.27 13.9 (37) | ACA T 0.26 13.5 (36) | AAA K 0.42 21.0 (56) | AGA R 0.24 14.2 (38) |
| AUG M 1.00 28.1 (75) | ACG T 0.14 7.1 (19) | AAG K 0.58 29.2 (78) | AGG R 0.27 16.1 (43) |
| GUU V 0.28 19.8 (53) | GCU A 0.35 31.4 (84) | GAU D 0.63 35.9 (96) | GGU G 0.29 26.6 (71) |
| GUC V 0.21 15.0 (40) | GCC A 0.20 18.0 (48) | GAC D 0.37 21.0 (56) | GGC G 0.20 18.0 (48) |
| GUA V 0.14 10.1 (27) | GCA A 0.33 29.6 (79) | GAA E 0.41 18.3 (49) | GGA G 0.35 31.4 (84) |
| GUG V 0.36 25.1 (67) | GCG A 0.11 9.7 (26) | GAG E 0.59 26.2 (70) | GGG G 0.16 14.2 (38) |

TABLE 5

Codon usage for *Arabidopsis* (codon, amino acid, frequency, per thousand)

| | | | |
|---|---|---|---|
| UUU F 0.51 21.8 | UCU S 0.28 25.2 | UAU Y 0.52 14.6 | UGU C 0.60 10.5 |
| UUC F 0.49 20.7 | UCC S 0.13 11.2 | UAC Y 0.48 13.7 | UGC C 0.40 7.2 |
| UUA L 0.14 12.7 | UCA S 0.20 18.3 | UAA * 0.36 0.9 | UGA * 0.44 1.2 |
| UUG L 0.22 20.9 | UCG S 0.10 9.3 | UAG * 0.20 0.5 | UGG W 1.00 12.5 |
| CUU L 0.26 24.1 | CCU P 0.38 18.7 | CAU H 0.61 13.8 | CGU R 0.17 9.0 |
| CUC L 0.17 16.1 | CCC P 0.11 5.3 | CAC H 0.39 8.7 | CGC R 0.07 3.8 |
| CUA L 0.11 9.9 | CCA P 0.33 16.1 | CAA Q 0.56 19.4 | CGA R 0.12 6.3 |
| CUG L 0.11 9.8 | CCG P 0.18 8.6 | CAG Q 0.44 15.2 | CGG R 0.09 4.9 |
| AUU I 0.41 21.5 | ACU T 0.34 17.5 | AAU N 0.52 22.3 | AGU S 0.16 14.0 |
| AUC I 0.35 18.5 | ACC T 0.20 10.3 | AAC N 0.48 20.9 | AGC S 0.13 11.3 |
| AUA I 0.24 12.6 | ACA T 0.31 15.7 | AAA K 0.49 30.8 | AGA R 0.35 19.0 |
| AUG M 1.00 24.5 | ACG T 0.15 7.7 | AAG K 0.51 32.7 | AGG R 0.20 11.0 |
| GUU V 0.40 27.2 | GCU A 0.43 28.3 | GAU D 0.68 36.6 | GGU G 0.34 22.2 |
| GUC V 0.19 12.8 | GCC A 0.16 10.3 | GAC D 0.32 17.2 | GGC G 0.14 9.2 |
| GUA V 0.15 9.9 | GCA A 0.27 17.5 | GAA E 0.52 34.3 | GGA G 0.37 24.2 |
| GUG V 0.26 17.4 | GCG A 0.14 9.0 | GAG E 0.48 32.2 | GGG G 0.16 10.2 |

Host Cells

The host cell can be a single cell (e.g., microalga, bacteria, yeast) or part of a multicellular organism such as a plant or fungus. Methods for expressing Fatb genes in a plant are described, e.g., in U.S. Pat. Nos. 5,850,022; 5,723,761; 5,639,790; 5,807,893; 5,455,167; 5,654,495; 5,512,482; 5,298,421; 5,667,997; 5,344,771; and 5,304,481, or can be obtained using other techniques generally known in plant biotechnology. Engineering of oleaginous microbes including those of Chlorophyta is disclosed in WO2010/063032, WO2011/150411, and WO2012/106560 and in the examples below.

Examples of oleaginous host cells include plant cells and microbial cells having a type II fatty acid biosynthetic pathway, including plastidic oleaginous cells such as those of oleaginous algae. Specific examples of microalgal cells include heterotrophic or obligate heterotrophic microalgae of the phylum Chlorophtya, the class Trebouxiophytae, the order Chlorellales, or the family Chlorellacae. Examples of oleaginous microalgae are provided in Published PCT Patent Applications WO2008/151149, WO2010/06032, WO2011/150410, and WO2011/150411, including species of *Chlorella* and *Prototheca*, a genus comprising obligate heterotrophs. The oleaginous cells can be, for example, capable of producing 20, 25, 30, 40, 50, 60, 70, 80, 85, or about 90% oil by cell weight, ±5%. Optionally, the oils produced can be low in DHA or EPA fatty acids. For example, the oils can comprise less than 5%, 2%, or 1% DHA and/or EPA. The above-mentioned publications also disclose methods for cultivating such cells and extracting oil, especially from microalgal cells; such methods are applicable to the cells disclosed herein and incorporated by reference for these teachings. When microalgal cells are used they can be cultivated autotrophically (unless an obligate heterotroph) or in the dark using a sugar (e.g., glucose, fructose and/or sucrose). In any of the embodiments described herein, the cells can be heterotrophic cells comprising an exogenous invertase gene so as to allow the cells to produce oil from a sucrose feedstock. Alternately, or in addition, the cells can metabolize xylose from cellulosic feedstocks. For example, the cells can be genetically engineered to express one or more xylose metabolism genes such as those encoding an active xylose transporter, a xylulose-5-phosphate transporter, a xylose isomerase, a xylulokinase, a xylitol dehydrogenase and a xylose reductase. See WO2012/154626, "GENETICALLY ENGINEERED MICROORGANISMS THAT METABOLIZE XYLOSE", published Nov. 15, 2012. The cells can be cultivated on a depolymerized cellulosic feedstock such as acid or enzyme hydrolyzed bagasse, sugar beet pulp, corn stover, wood chips, sawdust or switchgrass. Optionally, the cells can be cultivated on a depolymerized cellulosic feedstock comprising glucose and at least 5, 10, 20, 30 or 40% xylose, while producing at least 20% lipid by dry weight. Optionally, the lipid comprises triglycerides having a fatty acid profile characterized by at least 10, 15 or 20% C12:0

Oils and Related Products

The oleaginous cells express one or more exogenous genes encoding fatty acid biosynthesis enzymes. As a result, some embodiments feature cell oils that were not obtainable from a non-plant or non-seed oil, or not obtainable at all.

The oleaginous cells produce a storage oil, which is primarily triacylglyceride and may be stored in storage bodies of the cell. A raw oil may be obtained from the cells by disrupting the cells and isolating the oil. WO2008/151149, WO2010/06032, WO2011/150410, and WO2011/1504 disclose heterotrophic cultivation and oil isolation techniques. For example, oil may be obtained by cultivating, drying and pressing the cells. Methods for pressing cells are given in WO2010/120939. The oils produced may be refined, bleached and deodorized (RBD) as known in the art or as described in WO2010/120939. The raw or RBD oils may be used in a variety of food, chemical, and industrial products or processes. After recovery of the oil, a valuable residual biomass remains. Uses for the residual biomass include the production of paper, plastics, absorbents, adsorbents, as animal feed, for human nutrition, or for fertilizer.

Where a fatty acid profile of a triglyceride (also referred to as a "triacylglyceride" or "TAG") cell oil is given here, it will be understood that this refers to a nonfractionated sample of the storage oil extracted from the cell analyzed under conditions in which phospholipids have been removed or with an analysis method that is substantially insensitive to the fatty acids of the phospholipids (e.g. using chromatography and mass spectrometry). The oil may be subjected to an RBD process to remove phospholipids, free fatty acids and odors yet have only minor or negligible changes to the fatty acid profile of the triglycerides in the oil. Because the cells are oleaginous, in some cases the storage oil will constitute the bulk of all the TAGs in the cell.

The stable carbon isotope value $\delta 13C$ is an expression of the ratio of 13C/12C relative to a standard (e.g. PDB, carbonite of fossil skeleton of Belemnite americana from Peedee formation of South Carolina). The stable carbon isotope value $\delta 13C$ (0/00) of the oils can be related to the $\delta 13C$ value of the feedstock used. In some embodiments, the oils are derived from oleaginous organisms heterotrophically grown on sugar derived from a C4 plant such as corn or sugarcane. In some embodiments the $\delta 13C$ (0/00) of the oil is from −10 to −17 0/00 or from −13 to −16 0/00.

The oils produced according to the above methods in some cases are made using a microalgal host cell. As described above, the microalga can be, without limitation, fall in the classification of Chlorophyta, Trebouxiophyceae, Chlorellales, Chlorellaceae, or Chlorophyceae. It has been found that microalgae of Trebouxiophyceae can be distinguished from vegetable oils based on their sterol profiles. Oil produced by Chlorella protothecoides was found to produce sterols that appeared to be brassicasterol, ergosterol, campesterol, stigmasterol, and β-sitosterol, when detected by GC-MS. However, it is believed that all sterols produced by Chlorella have C24β stereochemistry. Thus, it is believed that the molecules detected as campesterol, stigmasterol, and β-sitosterol, are actually 22,23-dihydrobrassicasterol, proferasterol and clionasterol, respectively. Thus, the oils produced by the microalgae described above can be distinguished from plant oils by the presence of sterols with C24β stereochemistry and the absence of C24α stereochemistry in the sterols present. For example, the sterols produced may contain 22,23-dihydrobrassicasterol while lacking campesterol; contain clionasterol, while lacking in β-sitosterol, and/or contain poriferasterol while lacking stigmasterol. Alternately, or in addition, the oils may contain significant amounts of $\Delta^7$-poriferasterol.

In one embodiment, the oils provided herein are not vegetable oils. Vegetable oils are oils extracted from plants and plant seeds. Vegetable oils can be distinguished from the non-plant oils provided herein on the basis of their oil content. A variety of methods for analyzing the oil content can be employed to determine the source of the oil or whether adulteration of an oil provided herein with an oil of a different (e.g. plant) origin has occurred. The determination can be made on the basis of one of or a combination of the analytical methods. These tests include but are not limited to analysis of one or more of free fatty acids, fatty acid profile, total triacylglycerol content, diacylglycerol content, peroxide values, spectroscopic properties (e.g. UV absorption), sterol profile, sterol degradation products, antioxidants (e.g. tocopherols), pigments (e.g. chlorophyll), d13C values and sensory analysis (e.g. taste, odor, and mouth feel). Many such tests have been standardized for commercial oils such as the Codex Alimentarius standards for edible fats and oils.

Sterol profile analysis is a particularly well-known method for determining the biological source of organic matter. Campesterol, b-sitosterol, and stigmasterol are common plant sterols, with b-sitosterol being a principle plant sterol. For example, b-sitosterol was found to be in greatest abundance in an analysis of certain seed oils, approximately 64% in corn, 29% in rapeseed, 64% in sunflower, 74% in cottonseed, 26% in soybean, and 79% in olive oil (Gul et al. J. Cell and Molecular Biology 5:71-79, 2006).

Oil isolated from Prototheca moriformis strain UTEX1435 were separately clarified (CL), refined and bleached (RB), or refined, bleached and deodorized (RBD) and were tested for sterol content according to the procedure described in JAOCS vol. 60, no. 8, August 1983. Results of the analysis are shown below (units in mg/100 g):

TABLE 6

| | Sterol | Crude | Clarified | Refined & bleached | Refined, bleached, & deodorized |
|---|---|---|---|---|---|
| 1 | Ergosterol | 384 (56%) | 398 (55%) | 293 | 302 (50%) |
| 2 | 5,22-cholestadien-24-methyl-3-ol (Brassicasterol) | 14.6 (2.1%) | 18.8 (2.6%) | 14 (2.4%) | 15.2 (2.5%) |
| 3 | 24-methylcholest-5-en-3-ol (Campesterol or 22,23-dihydrobrassicasterol) | 10.7 (1.6%) | 11.9 (1.6%) | 10.9 (1.8%) | 10.8 (1.8%) |
| 4 | 5,22-cholestadien-24-ethyl-3-ol (Stigmasterol or poriferasterol) | 57.7 (8.4%) | 59.2 (8.2%) | 46.8 (7.9%) | 49.9 (8.3%) |
| 5 | 24-ethylcholest-5-en-3-ol (β-Sitosterol or clionasterol) | 9.64 (1.4%) | 9.92 (1.4%) | 9.26 (1.6%) | 10.2 (1.7%) |
| 6 | Other sterols | 209 | 221 | 216 | 213 |
| | Total sterols | 685.64 | 718.82 | 589.96 | 601.1 |

These results show three striking features. First, ergosterol was found to be the most abundant of all the sterols, accounting for about 50% or more of the total sterols. The amount of ergosterol is greater than that of campesterol, β-sitosterol, and stigmasterol combined. Ergosterol is steroid commonly found in fungus and not commonly found in plants, and its presence particularly in significant amounts serves as a useful marker for non-plant oils. Secondly, the oil was found to contain brassicasterol. With the exception of rapeseed oil, brassicasterol is not commonly found in plant based oils. Thirdly, less than 2% β-sitosterol was found to be present. β-sitosterol is a prominent plant sterol not commonly found in microalgae, and its presence particularly in significant amounts serves as a useful marker for oils of plant origin. In summary, *Prototheca moriformis* strain UTEX1435 has been found to contain both significant amounts of ergosterol and only trace amounts of β-sitosterol as a percentage of total sterol content. Accordingly, the ratio of ergosterol:β-sitosterol or in combination with the presence of brassicasterol can be used to distinguish this oil from plant oils.

In some embodiments, the oil content of an oil provided herein contains, as a percentage of total sterols, less than 20%, 15%, 10%, 5%, 4%, 3%, 2%, or 1% β-sitosterol. In other embodiments the oil is free from β-sitosterol.

In some embodiments, the oil is free from one or more of β-sitosterol, campesterol, or stigmasterol. In some embodiments the oil is free from β-sitosterol, campesterol, and stigmasterol. In some embodiments the oil is free from campesterol. In some embodiments the oil is free from stigmasterol.

In some embodiments, the oil content of an oil provided herein comprises, as a percentage of total sterols, less than 20%, 15%, 10%, 5%, 4%, 3%, 2%, or 1% 24-ethylcholest-5-en-3-ol. In some embodiments, the 24-ethylcholest-5-en-3-ol is clionasterol. In some embodiments, the oil content of an oil provided herein comprises, as a percentage of total sterols, at least 1%, 2%, 3%, 4%, 5%, 6%, 7%, 8%, 9%, or 10% clionasterol.

In some embodiments, the oil content of an oil provided herein contains, as a percentage of total sterols, less than 20%, 15%, 10%, 5%, 4%, 3%, 2%, or 1% 24-methylcholest-5-en-3-ol. In some embodiments, the 24-methylcholest-5-en-3-ol is 22,23-dihydrobrassicasterol. In some embodiments, the oil content of an oil provided herein comprises, as a percentage of total sterols, at least 1%, 2%, 3%, 4%, 5%, 6%, 7%, 8%, 9%, or 10% 22,23-dihydrobrassicasterol.

In some embodiments, the oil content of an oil provided herein contains, as a percentage of total sterols, less than 20%, 15%, 10%, 5%, 4%, 3%, 2%, or 1% 5,22-cholestadien-24-ethyl-3-ol. In some embodiments, the 5,22-cholestadien-24-ethyl-3-ol is poriferasterol. In some embodiments, the oil content of an oil provided herein comprises, as a percentage of total sterols, at least 1%, 2%, 3%, 4%, 5%, 6%, 7%, 8%, 9%, or 10% poriferasterol.

In some embodiments, the oil content of an oil provided herein contains ergosterol or brassicasterol or a combination of the two. In some embodiments, the oil content contains, as a percentage of total sterols, at least 5%, 10%, 20%, 25%, 35%, 40%, 45%, 50%, 55%, 60%, or 65% ergosterol. In some embodiments, the oil content contains, as a percentage of total sterols, at least 25% ergosterol. In some embodiments, the oil content contains, as a percentage of total sterols, at least 40% ergosterol. In some embodiments, the oil content contains, as a percentage of total sterols, at least 5%, 10%, 20%, 25%, 35%, 40%, 45%, 50%, 55%, 60%, or 65% of a combination of ergosterol and brassicasterol.

In some embodiments, the oil content contains, as a percentage of total sterols, at least 1%, 2%, 3%, 4% or 5% brassicasterol. In some embodiments, the oil content contains, as a percentage of total sterols less than 10%, 9%, 8%, 7%, 6%, or 5% brassicasterol.

In some embodiments the ratio of ergosterol to brassicasterol is at least 5:1, 10:1, 15:1, or 20:1.

In some embodiments, the oil content contains, as a percentage of total sterols, at least 5%, 10%, 20%, 25%, 35%, 40%, 45%, 50%, 55%, 60%, or 65% ergosterol and less than 20%, 15%, 10%, 5%, 4%, 3%, 2%, or 1% β-sitosterol. In some embodiments, the oil content contains, as a percentage of total sterols, at least 25% ergosterol and less than 5% β-sitosterol. In some embodiments, the oil content further comprises brassicasterol.

Sterols contain from 27 to 29 carbon atoms (C27 to C29) and are found in all eukaryotes. Animals exclusively make C27 sterols as they lack the ability to further modify the C27 sterols to produce C28 and C29 sterols. Plants however are able to synthesize C28 and C29 sterols, and C28/C29 plant sterols are often referred to as phytosterols. The sterol profile of a given plant is high in C29 sterols, and the primary sterols in plants are typically the C29 sterols b-sitosterol and stigmasterol. In contrast, the sterol profile of non-plant organisms contain greater percentages of C27 and C28 sterols. For example the sterols in fungi and in many microalgae are principally C28 sterols. The sterol profile and particularly the striking predominance of C29 sterols over C28 sterols in plants has been exploited for determining the proportion of plant and marine matter in soil samples (Huang, Wen-Yen, Meinschein W. G., "Sterols as ecological indicators"; Geochimica et Cosmochimia Acta. Vol 43. pp 739-745).

In some embodiments the primary sterols in the microalgal oils provided herein are sterols other than b-sitosterol and stigmasterol. In some embodiments of the microalgal oils, C29 sterols make up less than 50%, 40%, 30%, 20%, 10%, or 5% by weight of the total sterol content.

In some embodiments the microalgal oils provided herein contain C28 sterols in excess of C29 sterols. In some embodiments of the microalgal oils, C28 sterols make up greater than 50%, 60%, 70%, 80%, 90%, or 95% by weight of the total sterol content. In some embodiments the C28 sterol is ergosterol. In some embodiments the C28 sterol is brassicasterol.

In embodiments, oleaginous cells expressing one or more of the genes of Table 1 can produce an oil with at least 20, 40, 60 or 70% of C8, C10, C12, C14 or C16 fatty acids. In a specific embodiment, the level of myristate (C14:0) in the oil is greater than 30%.

Thus, in embodiments, there is a process for producing an oil, triglyceride, fatty acid, or derivative of any of these, comprising transforming a cell with any of the nucleic acids discussed herein. In another embodiment, the transformed cell is cultivated to produce an oil and, optionally, the oil is extracted. Oil extracted in this way can be used to produce food, oleochemicals or other products.

The oils discussed above alone or in combination are useful in the production of foods, fuels and chemicals (including plastics, foams, films, etc). The oils, triglycerides, fatty acids from the oils may be subjected to C—H activation, hydroamino methylation, methoxy-carbonation, ozonolysis, enzymatic transformations, epoxidation, methylation, dimerization, thiolation, metathesis, hydro-alkylation, lactonization, or other chemical processes.

After extracting the oil, a residual biomass may be left, which may have use as a fuel, as an animal feed, or as an ingredient in paper, plastic, or other product. For example, residual biomass from heterotrophic algae can be used in such products.

Deletion Mutants of FATB Genes that Enhance Production of Mid-Chain Fatty Acids in Host Cells In another embodiment, there is a method for increasing the production of C12 or C10 fatty acids. The method comprises producing a polynucleotide having a sequence encoding a FATB acyl-ACP thioesterase but encoding a deletion mutation in the region corresponding to amino acids 66-98 of the SalFATB2 gene (SEQ ID NO: 8); i.e., a deletion in the FATB region corresponding to that characterized by SEQ ID NO: 42. In some cases, the region of the deletion mutant for the starting FATB already contains gaps; in this case, further residues in the region can be removed. For example, UcFATB2 has a 2-residue gap at positions 95-96 relative to SalFatB2, UcFatB1 has a 6-residue gap at positions 92-97 relative to SalFatB2, and LbeFatB1 has a 4-residue gap at positions 94-97 relative to SalFatB2. The full 32 amino acid deletion or shorter deletions (i.e., of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 amino acid residues) may also be effective in increasing C12 fatty acids in the FATB enzymes disclosed here or others known in the art (e.g., those with at least 80, 85, 90 or 95% identity to one of SEQ ID NOs: 1-18); this can readily be determined using the techniques disclosed here including the Examples.

Vectors containing genes that encode the deletion mutants can be expressed in an oleaginous host cell (single or multicellular) and compared to an untransformed cell to select mutants that increase the production of mid-chain fatty acids by the cell. This can be determined by extracting the oil and using has chromatography techniques.

Accordingly, in an embodiment, there is a method for increasing the production of C10-C14 fatty acids in a cell. The method comprises producing or providing an exogenous polynucleotide, the exogenous polynucleotide comprising an, optionally heterologous, control sequence fused to a coding region that encodes a plastid targeting sequence and a mutant FATB acyl-ACP thioesterase enzyme domain. The FATB acyl-ACP thioesterase enzyme domain has a deletion in the region corresponding to amino acids 66-98 of SEQ ID NO: 8. The exogenous polynucleotide is expressed in an oleaginous host cell. As a result of the expression, the host cell produces an oil that is enriched in C12 fatty acids, relative to a control cell lacking the exogenous polynucleotide. In specific embodiments, the sum of C10 and C12 fatty acids in the fatty acid profile of the oil is increased by at least 10, 20, 30, 50, 100, 150, or 200%. For example, the amount of C12 fatty acids in the oil is increased by at least 2-fold relative to the control cell. The starting FATB gene is not the CcFATB4 gene (SEQ ID NO: 46), because this gene already has a gap spanning the domain in which the deletion is made. In a related embodiment, the deletion leads to an increase in C8 and/or C10 fatty acids.

In an embodiment, there is a polynucleotide encoding a protein sequence having at least 75, 80, 85, 85.5, 86, 86.5, 87, 87.5, 88, 88.5, 89, 89.5, 90, 90.5, 91, 91.5, 92, 92.5, 93, 93.5, 94, 94.5, 95, 95.5, 96, 96.5, 97, 97.5, 98, 98.5 or 99% amino acid identity to any of SEQ ID NOs: 43-46, 50, 51, 54 or 55. The polynucleotide can comprise at least 60, 65, 70, 75, 80, 85, 85.5, 86, 86.5, 87, 87.5, 88, 88.5, 89, 89.5, 90, 90.5, 91, 91.5, 92, 92.5, 93, 93.5, 94, 94.5, 95, 95.5, 96, 96.5, 97, 97.5, 98, 98.5 or 99% sequence identity to any of SEQ ID NOs 47, 48, 52, or 56, or equivalent sequence by virtue of the degeneracy of the genetic code. The sequence has a deletion in the region corresponding to amino acids 66-98, and is not that of CcFatB4 (SEQ ID NO: 46). In related embodiments, there is a protein encoded by one of the above sequences, a vector for transforming a host cell, or a host cell expressing one of the sequences. There is also a method of producing an oil comprising expressing one of these sequences in an oleaginous host cell, cultivating the cell, and isolating an oil from the cell. The oil recovered can be elevated in C12 fatty acids 10, 20, 50, 100, 150, 200% or more relative to a control cell lacking the polynucleotide. Example 3 demonstrates the increase in C12:0 fatty acids resulting from expression of the deletion mutants in a Eukaryotic microalga, relative to controls lacking the deletion.

The polynucleotide sequence can be codon optimized for a variety of organisms including according to Tables 2-5.

TABLE 7

FatB Deletion mutant sequences

| GENE (species, abbreviation) | Amino acid sequence SEQ ID NO: | Mature amino acid sequence (without targeting peptide) | Plant nucleic acid sequence codon-optimized for *Prototheca moriformis* |
|---|---|---|---|
| *Sassafras albidum* FATB1a (SalFATB1a) | 40 | 42 | 44 |
| *Lindera benzoin* FATB1a (LbeFATB1a) | 41 | 43 | 45 |
| CpauFATB1Δ28 (deletion mutant of Cuphea paucipetala FATB1) | 50 | 51 | 52 |
| ChFATB2Δ27 (deletion mutant of Cuphea hookeriana FATB1) | 54 | 55 | 56 |

In accordance with an embodiment, a method of genetically engineering a cell includes expressing in the cell, a polynucleotide that encodes a protein having at least 65, 70, 80, 85, 86, 86, 88, 89, 90, 91, 92, 93, 94, 95, 96, 97, 98, or 99% sequence identity to any of SEQ ID NOS: 40 to 43, 50, 51, 54 or 55; or has at least 65, 70, 80, 85, 86, 86, 88, 89, 90, 91, 92, 93, 94, 95, 96, 97, 98, or 99% sequence identity to SEQ ID NO: 44, 45, 52 or 56, or equivalent sequence by virtue of the degeneracy of the genetic code. In a specific embodiment, a method of genetically engineering a cell includes expressing in the cell, a polynucleotide that encodes a protein having at least 86.7% sequence identity to 42, at least 80.7% sequence identity to 43, at least 88.2% sequence identity SEQ ID NOS: 51.

Example 1. Discovery of Novel FATB Sequences

RNA was extracted from dried plant seeds and submitted for paired-end sequencing using the Illumina Hiseq 2000 platform. RNA sequence reads were assembled into corresponding seed transcriptomes using the Trinity software package and putative thioesterase-containing cDNA contigs were identified by mining transcriptomes for sequences with homology to known thioesterases. In some cases, these in silico identified putative thioesterase cDNAs were verified by direct reverse transcription PCR analysis using seed RNA and primer pairs targeting full-length thioesterase cDNAs. The resulting amplified products were cloned and sequenced de novo to confirm authenticity of identified thioesterase genes and to identify sequence variants arising from expression of different gene alleles or diversity of sequences within a population of seeds. For some sequences, a high-confidence, full-length transcript was assembled using Trinity and reverse transcription was not deemed to be necessary. The resulting amino acid sequences of all new putative FATB thioesterases were subjected to phylogenetic analyses using published full-length (Mayer and Shanklin, 2007) and truncated (THYME database) sequences as well as an extensive in-house phylogeny developed at Solazyme from FATB sequences identified in numerous oilseed transcriptomes. The in-house phylogeny comprising the acyl-ACP FATB thioesterases allows for prediction, in many cases, of the midchain specificity for each thioesterase; the FATBs predicted to be involved in biosynthesis of C8-C12 fatty acids were pursued.

The amino acid sequence and nucleic acid CDSs (native to the plant and codon optimized for *Prototheca moriformis*) of the novel FatB genes with and without their N-terminal plastid targeting peptides are shown in Table 1, above.

Example 2. Expression of Transforming Vectors Expressing Acyl-ACP FATB Thioesterases The nine acyl-ACP FATB thioesterase genes of Example 1 were synthesized in a codon-optimized form to reflect *Prototheca moriformis* (UTEX 1435) codon usage. A representative transforming construct and the sequence of the FATB enzymes is provided in SEQ ID NO: 38, using CcrasFATB1 as an example. The new thioesterases were synthesized with a modified transit peptide from *Chlorella protothecoides* (Cp) (SEQ ID NO: 40) in place of the native transit peptide. The modified transit peptide derived from the CpSAD1 gene, "CpSAD1tp_trimmed", was synthesized as an in-frame, N-terminal fusion to the FATB thioesterases in place of the native transit peptide.

Transgenic strains were generated via transformation of the base strain S7485 with a construct encoding 1 of the 12 FatB thioesterases. The construct pSZ5342/D4219 encoding CcrasFATB1 is shown as an example, but identical methods were used to generate each of the remaining 11 constructs encoding the different respective thioesterases. Construct pSZ5342 can be written as THI4A_5'::CrTUB2-ScSUC2-PmPGH:PmSAD2-2ver3-CpSAD1tp_trmd:CcrasFATB1-CvNR-THI4A_3'. The relevant restriction sites in the construct from 5'-3', BspQI, KpnI, BamHI, EcoRV, SpeI, XhoI, SacI, BspQI, respectively, are indicated in lowercase, bold, and underlined. BspQI sites delimit the 5' and 3' ends of the transforming DNA. Bold, lowercase sequences at the 5' and 3' end of the construct represent genomic DNA from UTEX 1435 that target integration to the THI4A locus via homologous recombination. Proceeding in the 5' to 3' direction, the selection cassette has the *C. reinhardtii* β-tubulin promoter driving expression of the *S. cerevisiae* gene SUC2 (conferring the ability to grow on sucrose) and the *P. moriformis* PGH gene 3' UTR. The promoter is indicated by lowercase, boxed text. The initiator ATG and terminator TGA for ScSUC2 are indicated by bold, uppercase italics, while the coding region is indicated with lowercase italics. The 3' UTR is indicated by lowercase underlined text. The spacer region between the two cassettes is indicated by upper case text. The second cassette containing the codon optimized CcrasFATB1 gene from *Cuphea crassiflora* fused to the heterologous *C. protothecoides* SAD1 plastid-targeting transit peptide, CpSAD1tp_trimmed, is driven by the *P. moriformis* SAD2-2ver3 pH5-responsive promoter and has the *Chlorella vulgaris* Nitrate Reductase (NR) gene 3' UTR. In this cassette, the PmSAD2-2ver3 promoter is indicated by lowercase, boxed text. The initiator ATG and terminator TGA for the CcrasFATB1 gene are indicated in bold, uppercase italics, while the coding region is indicated by lowercase italics. The 3' UTR is indicated by lowercase underlined text.

The sequence for all of the thioesterase constructs is identical with the exception of the encoded thioesterase. The full sequence for pSZ5342/D4219 integrating construct (SEQ ID NO: 38) is provided.

Constructs encoding heterologous FATB genes were transformed into a high-lipid-producing *Prototheca* strain and selected for the ability to grow on sucrose. Transformations, cell culture, lipid production and fatty acid analysis were all carried out as in WO2013/158938. Multiple transformations were performed. The fatty acid profiles of the strain with the highest C10 (for the first 6 genes listed), or C12 production (for the remaining genes) is reported in Table 8.

TABLE 8

Fatty acid profiles of top performing strain from each transformation (%; primary lipid)

| Species | Gene Name | C8:0 | C10:0 | C12:0 | C14:0 | C16:0 | C18:0 | C18:1 | C18:2 | C18:3α |
|---|---|---|---|---|---|---|---|---|---|---|
| *Cuphea crassiflora* | CcrasFATB1 | 0 | 4 | 1 | 3 | 35 | 3 | 47 | 5 | 0 |
| *Cuphea koehneana* | CkoeFATB3 | 0 | 9 | 2 | 3 | 32 | 3 | 45 | 5 | 0 |
| *Cuphea leptopoda* | CleptFATB1 | 0 | 6 | 1 | 3 | 34 | 4 | 46 | 5 | 0 |
| *Cuphea angustifolia* | CangFATB1 | 0 | 4 | 1 | 3 | 34 | 3 | 48 | 5 | 1 |
| *Cuphea llavea* | CllaFATB1 | 0 | 9 | 1 | 4 | 33 | 3 | 43 | 5 | 1 |
| *Cuphea lophostoma* | ClopFATB1 | 0 | 7 | 1 | 4 | 33 | 3 | 45 | 5 | 1 |
| *Sassafras albidum* | SalFATB1 | 0 | 0 | 7 | 3 | 32 | 4 | 47 | 5 | 1 |
| *Sassafras albidum* | SalFATB2 | 0 | 0 | 0 | 2 | 36 | 3 | 52 | 5 | 1 |
| *Lindera benzoin* | LbeFATB1 | 0 | 1 | 11 | 3 | 23 | 2 | 53 | 6 | 1 |
| None (Parent strain) | None | 0 | 0 | 0 | 2 | 38 | 4 | 48 | 5 | 1 |

The six thioesterases from the Lythraceae cluster all display specificity towards C10:0 fatty acids: CcrasFATB1, which exhibits 4% C10:0 and 1% C12:0 fatty acid levels; CkoeFATB3, which exhibits 9% C10:0 and 2% C12:0 fatty acid levels; CleptFATB1, which exhibits 6% C10:0 and 1% C12:0 fatty acid levels; CangFATB1, which exhibits 4% C10:0 and 1% C12:0 fatty acid levels; CllaFATB1, which exhibits 9% C10:0 and 1% C12:0 fatty acid levels; and, ClopFATB1, which exhibits 7% C10:0 and 1% C12:0 fatty acid levels.

SalFATB1 and LbeFATB1, both of the Lauraceae family, exhibit substantial activity towards C12:0 fatty acids.

Example 3. FATB Deletion Mutants of Lauraceae FATB Genes

Transforming vectors for deletion variants, of SalFATB1, and LbeFATB1, known respectively as SalFATB1a and LbeFATB1a, were synthesized, using the expression cassette and transit-peptide described in Example 2. The deletion variants had deletions in the region corresponding to amino acids 66-98 of the SalFATB2 gene (SEQ ID NO: 8). The constructs were codon-optimized to reflect UTEX 1435 codon usage. Transformations, cell culture, lipid production and fatty acid analysis were carried out as in Example 2. Constructs encoding heterologous FATB genes were transformed into a *Prototheca moriformis* strain and selected for the ability to grow on sucrose. The results for the two novel FATB thioesterases are displayed in Table 9.

TABLE 9

Fatty acid profiles of strains expressing deletion mutants of fatty acyl-ACP FATB genes (FATB1a) compared to wildtype genes lacking the deletion (FATB1).

| Gene | C8:0 | C10:0 | C12:0 | C14:0 | C16:0 | C18:0 | C18:1 | C18:2 | C18:3 |
|---|---|---|---|---|---|---|---|---|---|
| SalFATB1 | 0 | 0 | 7 | 3 | 32 | 4 | 47 | 5 | 1 |
| SalFATB1a | 0 | 0 | 15 | 3 | 27 | 3 | 45 | 5 | 1 |
| LbeFATB1 | 0 | 1 | 11 | 3 | 23 | 2 | 53 | 6 | 1 |
| LbeFATB1a | 0 | 3 | 28 | 5 | 18 | 2 | 37 | 4 | 0 |

SalFATB1 and LbeFATB1, both of the Lauraceae family, exhibit substantial activity towards C12:0 fatty acids. SalFATB1a, which has a deletion of the 32 amino acids LFAVITTIFSVAEKQWTNLEWKPKPKPRLPQL (SEQ ID NO: 47), produced up to 15% C12:0 compared to 7% produced by the wild-type SalFATB1. The mean C12:0 level in SalFATB1a was 8.3% compared to 3.7% in SalFATB1, demonstrating a greater than 2-fold increase in activity upon deletion of the 32 amino acids. LbeFATB1a, which had a deletion of the 28 amino acids LLTVITTIFSAAEKQWTNLERKPKPPHL (SEQ ID NO: 48), produced up to 28% C12:0 compared to 11% produced by the wild-type LbeFATB1. The mean C12:0 level in LbeFATB1a is 17.2% compared to just 5.7% in LbeFATB1, demonstrating a greater than 3.0-fold increase in activity upon deletion of the 28 amino acids. The data suggest that deletion of those amino acids significantly improves (e.g., by 2-3 fold) the C12 activity of two other Lauraceae family thioesterases, SalFATB1 and LbeFATB1.

Example 4. Additional Deletion Mutants from FATB Genes from Lythraceae

*P. moriformis* was transformed with additional deletion mutants of Lythraceae FATB genes above for Lauraceae FATB genes. Two deletion mutants were identified that showed elevated midchain (C8-14) fatty acid levels in cell-oil extracted from the microalga relative an equivalent transformation lacking the deletion. These are listed in Table 9, above in which they appear as CpauFATB1Δ28 and ChFATB2Δ27. Fatty acid profiles obtained in the *P. moriformis* model system are reported below in Table 10. ChFATB2Δ27 demonstrated an increase in C8 and C10 fatty acids when compared to the wild-type, elaborating an average of 3.8% C8:0 and 11.5% C10:0 compared to 2.7% C8:0 and 8.0% C10:0, respectively. CpauFATB1Δ28 demonstrates an increase in C10, C12 and C14 fatty acids when compared to the wild-type, elaborating an average of 7.6% C10:0 compared to 4.1% C10:0, respectively.

Example 5. Modify *Brassica napus* Thioesterase (BnOTE) Enzyme Specificity by Site Directed Mutagenesis In the example below, we demonstrate the ability of modifying the enzyme specificity of a FATA thioesterase originally isolated from *Brassica napus* (BnOTE, accession CAA52070), by site directed mutagenesis targeting two amino acids positions (D124 and D209).

To determine the impact of each amino acid substitution on the enzyme specificity of the BnOTE, the wild-type and the mutant BnOTE genes were cloned into a vector enabling expression within the lower palmitate *P. moriformis* strain S8588. The *Saccharomyces carlsbergensis* MEL1 gene (Accession no: AAA34770) was utilized as the selectable marker to introduce the wild-type and mutant BnOTE genes into FAD2-2 locus of *P. moriformis* strain S8588 by homologous recombination using previously described transformation methods (biolistics). The constructs that have been expressed in S8588 are listed in Table 11. S8588 is a recombinant *P. moriformis* strain having a FATA knockout and expressing an exogenous SUC2 gene and an exogenous *P. moriformis* KASII gene in the FATA locus. FATA knockouts that express sucrose invertase and/or KASII are described in co-owned applications WO2012/106560, WO2013/158938, WO2015/051319 and their respective priority applications thereof, all of which are herein incorporated by reference.

TABLE 11

DNA lot# and plasmid ID of DNA constructs that expressing wild-type and mutant BnOTE genes

| DNA Lot# | Solazyme Plasmid | SEQ ID NO: | Construct |
|---|---|---|---|
| D5309 | pSZ6315 | 57 | FAD2-2::PmHXT1-ScarMEL1-PmPGK:PmSAD2-2 V3-CpSADtp-BnOTE-PmSAD2-1 utr::FAD2-2 |
| D5310 | pSZ6316 | 58 | FAD2-2::PmHXT1-ScarMEL1-PmPGK:PmSAD2-2 V3-CpSADtp-BnOTE(D124A)-PmSAD2-1 utr::FAD2-2 |

TABLE 10

Fatty acid profiles of cell-oil from *P. moriformis* transformed with *Lythraceae* FATB deletion mutants for top performing transformants (mean given in parenthesis).

| Mutant | C8:0 | C10:0 | C12:0 | C14:0 | C16:0 | C18:0 | C18:1 | C18:2 | C18:3 |
|---|---|---|---|---|---|---|---|---|---|
| CpauFATB1 | 0 (0.0) | 9 (4.1) | 1 (0.6) | 3 (2.7) | 31 | 2 | 45 | 6 | 1 |
| CpauFATB1Δ28 | 0 (0.0) | 14 (7.6) | 2 (1.1) | 4 (3.0) | 30 | 3 | 42 | 5 | 1 |
| ChFATB2 | 7 (2.7) | 16 (8.0) | 0 (0.2) | 2 (2.0) | 21 | 3 | 44 | 5 | 1 |
| ChFATB2Δ27 | 9 (3.8) | 20 (11.5) | 0 (0.2) | 1 (1.8) | 17 | 2 | 45 | 5 | 0 |

TABLE 11-continued

DNA lot# and plasmid ID of DNA constructs that expressing wild-type and mutant BnOTE genes

| DNA Lot# | Solazyme Plasmid | SEQ ID NO: | Construct |
|---|---|---|---|
| D5311 | pSZ6317 | 59 | FAD2-2::PmHXT1-ScarMEL1-PmPGK:PmSAD2-2 V3-CpSADtp-BnOTE(D209A)-PmSAD2-1 utr::FAD2-2 |
| D5312 | pSZ6318 | 60 | FAD2-2::PmHXT1-ScarMEL1-PmPGK:PmSAD2-2 V3-CpSADtp-BnOTE(D124A, D209A)-PmSAD2-1 utr::FAD2-2 |

Construct pSZ6315: FAD2-2::PmHXT1-ScarMEL1-PmPGK:PmSAD2-2 V3-CpSADtp-BnOTE-PmSAD2-1 utr::FAD2-2

The sequence of the pSZ6315 transforming DNA is provided in SEQ ID NO: 57. Relevant restriction sites in pSZ6315 are indicated in lowercase, bold and underlining and are 5'-3' SgrAI, Kpn I, SnaBI, AvrII, SpeI, AscI, ClaI, Sac I, SbfI, respectively. SgrAI and SbfI sites delimit the 5' and 3' ends of the transforming DNA. Bold, lowercase sequences represent FAD2-2 genomic DNA that permit targeted integration at FAD2-2 locus via homologous recombination. Proceeding in the 5' to 3' direction, the *P. moriformis* HXT1 promoter driving the expression of the *Saccharomyces carlsbergensis* MEL1 gene is indicated by boxed text. The initiator ATG and terminator TGA for MEL1 gene are indicated by uppercase, bold italics while the coding region is indicated in lowercase italics. The *P. moriformis* PGK 3' UTR is indicated by lowercase underlined text followed by the *P. moriformis* SAD2-2 V3 promoter, indicated by boxed italics text. The Initiator ATG and terminator TGA codons of the wild-type BnOTE are indicated by uppercase, bold italics, while the remainder of the coding region is indicated by bold italics. The three-nucleotide codon corresponding to the target two amino acids, D124 and D209, are double underlined. The *P. moriformis* SAD2-1 3'UTR is again indicated by lowercase underlined text followed by the FAD2-2 genomic region indicated by bold, lowercase text.

Construct pSZ6316: FAD2-2::PmHXT1-ScarMEL1-PmPGK:PmSAD2-2 V3-CpSADtp-BnOTE (D124A)-PmSAD2-1 utr::FAD2-2

The sequence of the pSZ6316 transforming DNA is same as pSZ6315 except the D124A point mutation, the BnOTE D124A DNA sequence is provided in SEQ ID NO: 58.

Construct pSZ6317: FAD2-2::PmHXT1-ScarMEL1-PmPGK:PmSAD2-2 V3-CpSADtp-BnOTE (D209A)-PmSAD2-1 utr::FAD2-2

The sequence of the pSZ6317 transforming DNA is same as pSZ6315 except the D209A point mutation, the BnOTE D209A DNA sequence is provided in SEQ ID NO: 59.

Construct pSZ6318: FAD2-2::PmHXT1-ScarMEL1-PmPGK:PmSAD2-2 V3-CpSADtp-BnOTE (D124A, D209A)-PmSAD2-1 utr::FAD2-2

The sequence of the pSZ6318 transforming DNA is same as pSZ6315 except two point mutations, D124A and D209A, the BnOTE (D124A, D209A) DNA sequence is provided in SEQ ID NO:60.

Results

The DNA constructs containing the wild-type and mutant BnOTE genes were transformed into the low palmitate parental strain S8588, primary transformants were clonally purified and grown under standard lipid production conditions at pH5.0. The resulting profiles from representative clones arising from transformations with pSZ6315, pSZ6316, pSZ6317, and pSZ6318 into S8588 are shown in Table 12. The parental strain S8588 produces 5.4% C18:0, when transformed with the DNA cassette expressing wild-type BnOTE, the transgenic lines produce approximately 11% C18:0. The BnOTE mutant (D124A) increased the amount of C18:0 by at least 2 fold compared to the wild-type protein. In contrast, the BnOTE D209A mutation appears to have no impact on the enzyme activity/specificity of the BnOTE thioesterase. Finally, expression of the BnOTE (D124A, D209A) resulted in very similar fatty acid profile to what we observed in the transformants from S8588 expressing BnOTE (S124A), again indicating that D209A has no significant impact on the enzyme activity.

TABLE 12

Fatty acid profiles in S8588 and derivative transgenic lines transformed with wild-type and mutant BnOTE genes

| | | Fatty Acid Area % | | | |
|---|---|---|---|---|---|
| Transforming DNA | Sample ID | C16:0 | C18:0 | C18:1 | C18:2 |
| | pH 5; S8588 (parental strain) | 3.00 | 5.43 | 81.75 | 6.47 |
| D5309, pSZ6315, wild-type BnOTE | pH 5; S8588, D5309-6; | 3.86 | 11.68 | 76.51 | 5.06 |
| | pH 5; S8588, D5309-2; | 3.50 | 11.00 | 77.80 | 4.95 |
| | pH 5; S8588, D5309-9; | 3.51 | 10.72 | 78.03 | 5.00 |
| | pH 5; S8588, D5309-10; | 3.55 | 10.69 | 78.06 | 4.96 |
| | pH 5; S8588, D5309-11; | 3.61 | 10.69 | 78.05 | 4.95 |
| D5310, pSZ6316, BnOTE (D124A) | pH 5; S8588, D5310-6; | 4.27 | 31.55 | 55.31 | 5.30 |
| | pH 5; S8588, D5310-1; | 4.53 | 30.85 | 54.71 | 6.03 |
| | pH 5; S8588, D5310-5; | 5.21 | 20.75 | 65.43 | 5.02 |
| | pH 5; S8588, D5310-10; | 4.99 | 19.18 | 67.75 | 5.00 |
| | pH 5; S8588, D5310-2; | 4.90 | 18.92 | 68.17 | 4.98 |
| D5311, pSZ6317, BnOTE (D209A) | pH 5; S8588, D5311-3; | 3.50 | 11.90 | 76.95 | 4.98 |
| | pH 5; S8588, D5311-4; | 3.63 | 11.35 | 77.44 | 4.94 |
| | pH 5; S8588, D5311-14; | 3.47 | 11.23 | 77.68 | 4.98 |
| | pH 5; S8588, D5311-10; | 3.60 | 11.20 | 77.53 | 5.00 |
| | pH 5; S8588, D5311-12; | 3.53 | 11.12 | 77.59 | 5.09 |
| D5312, pSZ6318, BnOTE (D127A, D212A) | pH 5; S8588, D5312-20; | 4.79 | 37.97 | 47.74 | 6.01 |
| | pH 5; S8588, D5312-40; | 5.97 | 22.94 | 62.20 | 5.11 |
| | pH 5; S8588, D5312-39; | 6.07 | 22.75 | 62.24 | 5.17 |
| | pH 5; S8588, D5312-16; | 5.25 | 18.81 | 67.36 | 5.09 |
| | pH 5; S8588, D5312-26; | 4.93 | 18.70 | 68.37 | 4.96 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for producing an oil, the method comprising:
   (a) providing an oleaginous microalgal cell, the cell expressing a functional, acyl-ACP thioesterase comprising at least 95, 96, 97, 98, or 99% sequence identity to SEQ ID NO:51, wherein the thioesterase does not comprise amino acid residues 83-110 of SEQ ID NO: 49;
   (b) cultivating the cell to produce a cell-oil; and
   (c) isolating the cell-oil from the cell, wherein the oil is enriched in C10, C12 and C14 fatty acids in comparison to oil produced by an oleaginous microalgal expressing a wild-type thioesterase.

2. A cDNA encoding a functional, acyl-ACP thioesterase comprising at least 95, 96, 97, 98, or 99% sequence identity to SEQ ID NO:51, wherein the thioesterase does not comprise amino acid residues 83-110 of SEQ ID NO: 49.

3. A method of genetically engineering a cell comprising expressing in the cell, a polynucleotide or equivalent sequence by virtue of the degeneracy of the genetic code, the polynucleotide encoding a functional acyl-ACP thioesterase comprising at least 95, 96, 97, 98, or 99% sequence identity to SEQ ID NO:51, wherein the thioesterase does not comprise amino acid residues 83-110 of SEQ ID NO: 49.

4. An oil produced according to the method of claim 1, wherein the oil is produced by a microalgae that has a microalgal sterol profile, and optionally, lacks C24-alpha sterols.

5. An oil-derived product that is derived from the oil of claim 4, wherein the oil-derived product is, optionally a fatty acid, fuel, chemical, or food.

6. The method of claim 1, wherein the oleaginous microalgal cell is a heterotrophic microalgae.

7. The method of claim 1, wherein the oleaginous microalgal cell is of the phylum Chlorophtya.

8. The method of claim 1, wherein the oleaginous microalgal cell is of the class Trebouxiophytae.

9. The method of claim 1, wherein the oleaginous microalgal cell is of the order Chlorellales.

10. The method of claim 1, wherein the oleaginous microalgal cell is of the family Chlorellacae.

11. The method of claim 1, wherein the oleaginous microalgal cell is of the genus *Prototheca*.

12. The method of claim 1, wherein the oleaginous microalgal cell is of the species *Prototheca moriformis*.

13. An expression cassette comprising the cDNA of claim 2.

14. An oleaginous microalgal cell comprising the expression cassette of claim 13.

15. The oleaginous microalgal cell of claim 14, wherein the oleaginous microalgal cell is a heterotrophic microalgae.

16. The oleaginous microalgal cell of claim 14, wherein the oleaginous microalgal cell is of the phylum Chlorophtya.

17. The oleaginous microalgal cell of claim 14, wherein the oleaginous microalgal cell is of the class Trebouxiophytae.

18. The oleaginous microalgal cell of claim 14, wherein the oleaginous microalgal cell is of the order Chlorellales.

19. The oleaginous microalgal cell of claim 14, wherein the oleaginous microalgal cell is of the family Chlorellacae.

20. The oleaginous microalgal cell of claim 14, wherein the oleaginous microalgal cell is of the genus *Prototheca*.

21. The oleaginous microalgal cell of claim 14, wherein the oleaginous microalgal cell is of the species *Prototheca moriformis*.

* * * * *

UNITED STATES PATENT AND TRADEMARK OFFICE
CERTIFICATE OF CORRECTION

| | | |
|---|---|---|
| PATENT NO. | : 10,125,382 B2 | Page 1 of 1 |
| APPLICATION NO. | : 14/858527 | |
| DATED | : November 13, 2018 | |
| INVENTOR(S) | : Jason Casolari et al. | |

It is certified that error appears in the above-identified patent and that said Letters Patent is hereby corrected as shown below:

In the Claims

In Claim 1, Column 135, Line 20, please insert --cell-- after the word 'microalgal'

Signed and Sealed this
Twenty-third Day of April, 2019

Andrei Iancu
*Director of the United States Patent and Trademark Office*

SEQUENCE LISTING

```
<160> NUMBER OF SEQ ID NOS: 62

<210> SEQ ID NO 1
<211> LENGTH: 418
<212> TYPE: PRT
<213> ORGANISM: Cuphea crassiflora

<400> SEQUENCE: 1

Met Val Ala Ala Ala Ser Ser Ala Phe Phe Pro Val Pro Ala Pro
1               5                   10                  15

Gly Thr Ser Thr Lys Pro Arg Lys Ser Gly Asn Trp Pro Ser Arg Leu
                20                  25                  30

Ser Pro Ser Ser Lys Pro Lys Ser Ile Pro Asn Gly Gly Phe Gln Val
                35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Thr Ala Ile Thr Thr Val Phe Val Ala Ala Glu Lys Gln Trp Thr Met
                100                 105                 110

Leu Asp Arg Lys Ser Lys Arg Pro Asp Met Leu Val Asp Ser Val Gly
                115                 120                 125

Leu Lys Ser Ile Val Arg Asp Gly Leu Val Ser Arg Gln Ser Phe Ser
                130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
                180                 185                 190

Asp Leu Ile Trp Val Leu Thr Lys Met Gln Ile Met Val Asn Arg Tyr
                195                 200                 205

Pro Thr Trp Gly Asp Thr Val Glu Ile Asn Thr Trp Phe Ser Gln Ser
                210                 215                 220

Gly Lys Ile Gly Met Gly Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
                260                 265                 270

Thr Pro His Phe Val Asp Ser Pro His Val Ile Glu Asp Asn Asp Arg
                275                 280                 285

Lys Leu His Lys Phe Asp Val Lys Thr Gly Asp Ser Ile Arg Lys Gly
                290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335
```

-continued

```
Glu Thr Gln Glu Leu Cys Ser Leu Thr Val Gly Tyr Arg Arg Glu Cys
                340                 345                 350

Gly Met Asp Ser Lys Leu Glu Ser Val Thr Ala Met Asp Pro Ser Glu
            355                 360                 365

Glu Asp Gly Val Arg Ser Gln Tyr Asn His Leu Leu Arg Leu Glu Asp
        370                 375                 380

Gly Thr Asp Val Val Lys Gly Arg Thr Glu Trp Arg Pro Lys Asn Ala
385                 390                 395                 400

Gly Thr Asn Gly Ala Ile Ser Thr Gly Lys Thr Ser Asn Gly Asn Ser
                405                 410                 415

Val Ser

<210> SEQ ID NO 2
<211> LENGTH: 415
<212> TYPE: PRT
<213> ORGANISM: Cuphea koehneana

<400> SEQUENCE: 2

Met Val Thr Ala Ala Ser Ser Ala Phe Phe Pro Val Pro Ala Pro
1               5                   10                  15

Gly Thr Ser Pro Lys Pro Gly Lys Ser Trp Pro Ser Ser Leu Ser Pro
            20                  25                  30

Ser Phe Lys Pro Lys Ser Ile Pro Asn Ala Gly Phe Gln Val Lys Ala
        35                  40                  45

Asn Ala Ser Ala His Pro Lys Ala Asn Gly Ser Ala Val Asn Leu Lys
    50                  55                  60

Ser Gly Ser Leu Asn Thr Gln Glu Asp Thr Ser Ser Pro Pro Pro
65                  70                  75                  80

Arg Ala Phe Leu Asn Gln Leu Pro Asp Trp Ser Met Leu Leu Thr Ala
                85                  90                  95

Ile Thr Thr Val Phe Val Ala Ala Glu Lys Gln Trp Thr Met Arg Asp
            100                 105                 110

Arg Lys Ser Lys Arg Pro Asp Met Leu Val Asp Ser Val Gly Ser Lys
        115                 120                 125

Ser Ile Val Leu Asp Gly Leu Val Ser Arg Gln Ile Phe Ser Ile Arg
    130                 135                 140

Ser Tyr Glu Ile Gly Ala Asp Arg Thr Ala Ser Ile Glu Thr Leu Met
145                 150                 155                 160

Asn His Leu Gln Glu Thr Ser Ile Asn His Cys Lys Ser Leu Gly Leu
                165                 170                 175

Leu Asn Asp Gly Phe Gly Arg Thr Pro Gly Met Cys Lys Asn Asp Leu
            180                 185                 190

Ile Trp Val Leu Thr Lys Met Gln Ile Met Val Asn Arg Tyr Pro Thr
        195                 200                 205

Trp Gly Asp Thr Val Glu Ile Asn Thr Trp Phe Ser His Ser Gly Lys
    210                 215                 220

Ile Gly Met Ala Ser Asp Trp Leu Ile Thr Asp Cys Asn Thr Gly Glu
225                 230                 235                 240

Ile Leu Ile Arg Ala Thr Ser Val Trp Ala Met Met Asn Gln Lys Thr
                245                 250                 255

Arg Arg Phe Ser Arg Leu Pro Tyr Glu Val Arg Gln Glu Leu Thr Pro
            260                 265                 270

His Tyr Val Asp Ser Pro His Val Ile Glu Asp Asn Asp Arg Lys Leu
        275                 280                 285
```

His Lys Phe Asp Val Lys Thr Gly Asp Ser Ile Arg Lys Gly Leu Thr
    290                 295                 300

Pro Lys Trp Asn Asp Leu Asp Val Asn Gln His Val Asn Asn Val Lys
305                 310                 315                 320

Tyr Ile Gly Trp Ile Leu Glu Ser Met Pro Ile Glu Val Leu Glu Thr
                    325                 330                 335

Gln Glu Leu Cys Ser Leu Thr Val Glu Tyr Arg Arg Glu Cys Gly Met
                340                 345                 350

Asp Ser Val Leu Glu Ser Val Thr Ala Met Asp Pro Ser Glu Asp Gly
            355                 360                 365

Gly Leu Ser Gln Tyr Lys His Leu Leu Arg Leu Glu Asp Gly Thr Asp
370                 375                 380

Ile Val Lys Gly Arg Thr Glu Trp Arg Pro Lys Asn Ala Gly Thr Asn
385                 390                 395                 400

Gly Ala Ile Ser Thr Ala Lys Pro Ser Asn Gly Asn Ser Val Ser
                    405                 410                 415

<210> SEQ ID NO 3
<211> LENGTH: 417
<212> TYPE: PRT
<213> ORGANISM: Cuphea leptopoda

<400> SEQUENCE: 3

Met Val Gly Ala Ala Ala Ser Ser Ala Phe Phe Pro Ala Pro Ala Pro
1               5                   10                  15

Gly Thr Ser Pro Lys Pro Gly Lys Ser Gly Asn Trp Pro Ser Ser Leu
                20                  25                  30

Ser Pro Ser Leu Lys Pro Lys Ser Ile Pro Asn Gly Gly Phe Gln Val
            35                  40                  45

Lys Ala Asn Ala Ser Ala His Pro Lys Ala Asn Gly Ala Ala Val Asn
50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Thr Ala Ile Thr Thr Val Phe Val Ala Ala Glu Lys Gln Trp Thr Met
                    100                 105                 110

Leu Asp Arg Lys Ser Lys Arg Pro Asp Met Leu Val Asp Ser Val Gly
                115                 120                 125

Leu Lys Asn Ile Val Arg Asp Gly Leu Val Ser Arg Gln Ser Phe Ser
            130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
                    180                 185                 190

Asp Leu Ile Trp Val Leu Thr Lys Met Gln Ile Leu Val Asn Arg Tyr
                195                 200                 205

Pro Ala Trp Gly Asp Thr Val Glu Ile Asn Thr Trp Phe Ser Gln Ser
            210                 215                 220

Gly Lys Ile Gly Met Gly Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255

```
Lys Thr Arg Arg Phe Ser Arg Leu Pro Tyr Glu Val Arg Gln Glu Leu
                260                 265                 270

Thr Pro His Phe Val Asp Ser Pro His Val Ile Glu Asp Asn Asp Arg
            275                 280                 285

Lys Leu His Lys Phe Asp Val Lys Thr Gly Asp Ser Ile Arg Lys Gly
        290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335

Glu Thr Gln Glu Leu Cys Ser Leu Thr Val Glu Tyr Arg Arg Glu Cys
            340                 345                 350

Gly Met Asp Ser Val Leu Glu Ser Val Thr Ala Arg Asp Pro Ser Glu
        355                 360                 365

Asp Gly Gly Arg Ser Gln Tyr Asn His Leu Leu Arg Leu Glu Asp Gly
    370                 375                 380

Thr Asp Val Val Lys Gly Arg Thr Glu Trp Arg Ser Lys Asn Ala Gly
385                 390                 395                 400

Thr Asn Gly Ala Thr Ser Thr Ala Lys Thr Ser Asn Gly Asn Ser Val
                405                 410                 415

Ser

<210> SEQ ID NO 4
<211> LENGTH: 417
<212> TYPE: PRT
<213> ORGANISM: Cuphea angustifolia

<400> SEQUENCE: 4

Met Val Ala Ala Ala Ser Ser Ala Phe Phe Pro Val Pro Ala Pro
1               5                   10                  15

Gly Thr Ser Leu Lys Pro Gly Lys Ser Gly Asn Trp Pro Ser Ser Leu
            20                  25                  30

Ser Pro Ser Phe Lys Pro Lys Thr Ile Pro Ser Gly Gly Leu Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asp Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Thr Ala Ile Thr Thr Val Phe Val Ala Ala Glu Lys Gln Trp Thr Met
            100                 105                 110

Leu Asp Arg Lys Ser Lys Arg Pro Glu Met Leu Val Asp Ser Val Gly
        115                 120                 125

Leu Lys Ser Ser Val Arg Asp Gly Leu Val Ser Arg Gln Ser Phe Ser
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205
```

```
Pro Thr Trp Gly Asp Thr Val Glu Val Asn Thr Trp Phe Ser Gln Ser
    210                 215                 220

Gly Lys Ile Gly Met Ala Ser Asp Trp Leu Ile Ser Asp Cys Asn Thr
225             230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
            260                 265                 270

Thr Pro His Tyr Val Asp Ser Pro His Val Ile Glu Asp Asn Asp Arg
        275                 280                 285

Lys Leu His Lys Phe Asp Val Lys Thr Gly Asp Ser Ile Arg Lys Gly
    290                 295                 300

Leu Thr Pro Arg Trp Asn Asp Leu Asp Val Asn Gln His Val Ser Asn
305             310                 315                 320

Val Lys Tyr Ile Gly Trp Ile Leu Glu Ser Met Pro Ile Glu Val Leu
                325                 330                 335

Glu Thr Gln Glu Leu Cys Ser Leu Thr Val Glu Tyr Arg Arg Glu Cys
            340                 345                 350

Gly Met Asp Ser Val Leu Glu Ser Val Thr Ala Met Asp Pro Ser Glu
        355                 360                 365

Asp Gly Gly Val Ser Gln Tyr Lys His Leu Leu Arg Leu Glu Asp Gly
    370                 375                 380

Thr Asp Ile Val Lys Gly Arg Thr Glu Trp Arg Pro Lys Asn Ala Gly
385             390                 395                 400

Thr Asn Gly Ala Thr Ser Lys Ala Lys Thr Ser Asn Gly Asn Ser Val
                405                 410                 415

Ser

<210> SEQ ID NO 5
<211> LENGTH: 417
<212> TYPE: PRT
<213> ORGANISM: Cuphea llavea

<400> SEQUENCE: 5

Met Val Ala Ala Ala Ser Ala Phe Phe Pro Ala Pro Ala Pro
1               5                   10                  15

Gly Ser Ser Pro Lys Pro Gly Lys Pro Gly Asn Trp Pro Ser Ser Leu
            20                  25                  30

Ser Pro Ser Phe Lys Pro Lys Ser Ile Pro Asn Gly Arg Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65              70                  75                  80

Pro Pro Arg Ala Phe Leu Asn Gln Leu Pro Asp Trp Ser Met Leu Leu
                85                  90                  95

Ser Ala Ile Thr Thr Val Phe Val Ala Ala Glu Lys Gln Trp Thr Met
            100                 105                 110

Leu Asp Arg Lys Ser Lys Arg Pro Asp Met Leu Val Asp Ser Val Gly
        115                 120                 125

Leu Lys Asn Ile Val Arg Asp Gly Leu Val Ser Arg Gln Ser Phe Ser
    130                 135                 140

Ile Arg Ser Tyr Glu Ile Gly Ala Asp Arg Thr Ala Ser Ile Glu Thr
145             150                 155                 160
```

```
Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205

Pro Ala Trp Gly Asp Thr Val Glu Ile Asn Thr Trp Phe Ser Gln Ser
    210                 215                 220

Gly Lys Ile Gly Met Gly Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
            260                 265                 270

Thr Pro His Phe Val Asp Ser Pro His Val Ile Glu Asp Asn Asp Arg
        275                 280                 285

Lys Leu His Lys Phe Asp Val Lys Thr Gly Asp Ser Ile Arg Lys Gly
    290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335

Glu Thr Gln Glu Leu Cys Ser Leu Thr Val Glu Tyr Arg Arg Glu Cys
            340                 345                 350

Gly Met Asp Ser Val Leu Glu Ser Val Thr Ala Ile Asp Pro Ser Glu
        355                 360                 365

Asp Gly Gly Arg Ser Gln Tyr Asn His Leu Leu Arg Leu Asp Asp Gly
    370                 375                 380

Thr Asp Val Val Lys Gly Arg Thr Glu Trp Arg Pro Lys Asn Ala Gly
385                 390                 395                 400

Thr Asn Gly Ala Ile Ser Thr Gly Lys Thr Ser Asn Gly Asn Ser Val
                405                 410                 415

Ser

<210> SEQ ID NO 6
<211> LENGTH: 417
<212> TYPE: PRT
<213> ORGANISM: Cuphea lophostoma

<400> SEQUENCE: 6

Met Val Ala Ala Ala Ser Ser Ala Phe Phe Pro Val Pro Ala Pro
1               5                   10                  15

Gly Thr Ser Leu Lys Pro Trp Lys Gly Asn Trp Pro Ser Ser Leu
            20                  25                  30

Ser Pro Ser Phe Lys Pro Lys Thr Ile Pro Ser Gly Gly Phe Gln Val
        35                  40                  45

Lys Ala Asn Ala Ser Ala Gln Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Thr Ala Ile Thr Thr Val Phe Val Ala Ala Glu Lys Gln Trp Thr Met
            100                 105                 110
```

```
Leu Asp Arg Lys Ser Lys Arg Pro Glu Lys Leu Val Asp Ser Val Gly
            115                 120                 125

Leu Lys Ser Ser Val Arg Asp Gly Leu Val Ser Arg Gln Ser Phe Ser
        130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
                180                 185                 190

Asp Leu Ile Trp Val Leu Thr Lys Met Gln Ile Met Val Asn Arg Tyr
                195                 200                 205

Pro Thr Trp Gly Asp Thr Val Glu Ile Asn Thr Trp Phe Ser Gln Ser
        210                 215                 220

Gly Lys Ile Gly Met Ala Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
                260                 265                 270

Thr Pro His Tyr Val Asp Ser Pro His Val Ile Glu Asp Asn Asp Arg
                275                 280                 285

Lys Leu His Lys Phe Asp Val Lys Thr Gly Asp Ser Ile Arg Lys Gly
        290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335

Glu Thr Gln Glu Leu Cys Ser Leu Thr Val Glu Tyr Arg Arg Glu Cys
                340                 345                 350

Gly Met Asp Ser Val Leu Glu Ser Val Thr Ala Met Asp Pro Ser Glu
                355                 360                 365

Asp Glu Gly Arg Ser Gln Tyr Lys His Leu Leu Arg Leu Glu Asp Gly
                370                 375                 380

Thr Asp Ile Val Lys Gly Arg Thr Glu Trp Arg Pro Lys Asn Ala Gly
385                 390                 395                 400

Thr Asn Gly Ala Ile Ser Thr Ala Lys Asn Ser Asn Gly Asn Ser Val
                405                 410                 415

Ser

<210> SEQ ID NO 7
<211> LENGTH: 384
<212> TYPE: PRT
<213> ORGANISM: Sassafras albidum

<400> SEQUENCE: 7

Met Ala Thr Thr Ser Leu Ala Ser Ala Phe Cys Ser Met Lys Ala Val
1               5                   10                  15

Met Leu Ala Arg Asp Gly Arg Gly Met Lys Pro Arg Ser Ser Asp Leu
                20                  25                  30

Gln Leu Arg Ala Gly Asn Ala Gln Thr Pro Leu Lys Met Ile Asn Gly
            35                  40                  45

Thr Lys Phe Ser Tyr Thr Glu Ser Leu Lys Arg Leu Pro Asp Trp Ser
        50                  55                  60
```

```
Met Leu Phe Ala Val Ile Thr Thr Ile Phe Ser Val Ala Glu Lys Gln
 65                  70                  75                  80

Trp Thr Asn Leu Glu Trp Lys Pro Lys Pro Lys Pro Arg Leu Pro Gln
                 85                  90                  95

Leu Leu Asp Asp His Phe Gly Leu His Gly Leu Val Phe Arg Arg Thr
            100                 105                 110

Phe Ala Ile Arg Ser Tyr Glu Val Gly Pro Asp Arg Ser Thr Ser Ile
            115                 120                 125

Val Ala Val Met Asn His Leu Gln Glu Ala Thr Leu Asn His Ala Lys
130                 135                 140

Ser Val Gly Ile Leu Gly Asp Gly Phe Gly Thr Thr Leu Glu Met Ser
145                 150                 155                 160

Lys Arg Asp Leu Ala Trp Val Val Arg Arg Thr His Val Ala Val Glu
                165                 170                 175

Arg Tyr Pro Ala Trp Gly Asp Thr Val Glu Val Glu Cys Trp Ile Gly
            180                 185                 190

Ala Ser Gly Asn Asn Gly Met Arg Arg Asp Phe Leu Val Arg Asp Cys
            195                 200                 205

Lys Thr Gly Glu Ile Leu Thr Arg Cys Thr Ser Leu Ser Val Met Met
210                 215                 220

Asn Thr Arg Thr Arg Arg Leu Ser Lys Ile Pro Glu Glu Val Arg Gly
225                 230                 235                 240

Glu Ile Gly Pro Leu Phe Ile Asp Asn Val Ala Val Lys Asp Glu Glu
                245                 250                 255

Ile Lys Lys Leu Gln Lys Leu Asn Ser Ser Ala Asp Tyr Ile Gln
            260                 265                 270

Gly Gly Leu Thr Pro Arg Trp Asn Asp Leu Asp Val Asn Gln His Val
            275                 280                 285

Asn Asn Ile Lys Tyr Val Gly Trp Ile Leu Glu Thr Val Pro Asp Ser
290                 295                 300

Ile Phe Glu Ser His His Ile Ser Ser Ile Thr Leu Glu Tyr Arg Arg
305                 310                 315                 320

Glu Cys Thr Arg Asp Ser Val Leu Gln Ser Leu Thr Thr Val Ser Gly
                325                 330                 335

Gly Ser Leu Glu Ala Gly Leu Val Cys Asp His Leu Leu Gln Leu Glu
            340                 345                 350

Gly Gly Ser Glu Val Leu Arg Ala Arg Thr Glu Trp Arg Pro Lys Leu
            355                 360                 365

Thr Asp Ser Phe Arg Gly Ile Ile Val Ile Pro Ala Glu Pro Ser Val
370                 375                 380

<210> SEQ ID NO 8
<211> LENGTH: 384
<212> TYPE: PRT
<213> ORGANISM: Sassafras albidum

<400> SEQUENCE: 8

Met Ala Thr Thr Ser Leu Ala Ser Ala Phe Cys Ser Met Lys Ala Val
 1               5                  10                  15

Met Leu Ala Arg Asp Gly Arg Gly Met Lys Pro Arg Ser Ser Asp Leu
                20                  25                  30

Gln Leu Arg Ala Gly Asn Ala Gln Thr Pro Leu Lys Met Ile Asn Gly
            35                  40                  45

Thr Lys Phe Ser Tyr Thr Glu Ser Leu Lys Arg Leu Pro Asp Trp Ser
```

```
              50                  55                  60
    Met Leu Phe Ala Val Ile Thr Thr Ile Phe Ser Val Ala Glu Lys Gln
     65                  70                  75                  80

Trp Thr Asn Leu Glu Trp Lys Pro Lys Pro Lys Pro Arg Leu Pro Gln
                     85                  90                  95

Leu Leu Asp Asp His Phe Gly Leu His Gly Leu Val Phe Arg Arg Thr
                    100                 105                 110

Phe Ala Ile Arg Ser Tyr Glu Val Gly Pro Asp Arg Ser Thr Ser Ile
                    115                 120                 125

Val Ala Val Met Asn His Leu Gln Glu Ala Thr Leu Asn His Ala Lys
    130                 135                 140

Ser Val Gly Ile Leu Gly Asp Gly Phe Gly Thr Thr Leu Glu Met Ser
    145                 150                 155                 160

Lys Arg Asp Leu Ala Trp Val Val Arg Thr His Val Ala Val Glu
                    165                 170                 175

Arg Tyr Pro Ala Trp Gly Asp Thr Val Glu Val Glu Ala Trp Val Gly
                    180                 185                 190

Ala Ser Gly Asn Ile Gly Met Arg Arg Asp Phe Leu Val Arg Asp Cys
                    195                 200                 205

Lys Thr Gly His Ile Leu Ala Arg Cys Thr Ser Val Ser Val Met Met
                    210                 215                 220

Asn Ala Arg Thr Arg Arg Leu Ser Lys Ile Pro Gln Glu Val Arg Ala
    225                 230                 235                 240

Glu Ile Asp Pro Leu Phe Ile Glu Lys Val Ala Val Lys Glu Gly Glu
                    245                 250                 255

Ile Lys Lys Leu Gln Lys Phe Asn Asp Ser Thr Ala Asp Tyr Ile Gln
                    260                 265                 270

Gly Gly Trp Thr Pro Arg Trp Asn Asp Leu Asp Val Asn Gln His Val
                    275                 280                 285

Asn Asn Ile Lys Tyr Ile Gly Trp Ile Phe Lys Ser Val Pro Asp Ser
    290                 295                 300

Ile Ser Glu Asn His Tyr Leu Ser Ser Ile Thr Leu Glu Tyr Arg Arg
    305                 310                 315                 320

Glu Cys Thr Arg Gly Ser Ala Leu Gln Ser Leu Thr Thr Val Cys Gly
                    325                 330                 335

Asp Ser Ser Glu Ala Gly Ile Ile Cys Glu His Leu Leu Gln Leu Glu
                    340                 345                 350

Asp Gly Pro Glu Val Leu Arg Ala Arg Thr Glu Trp Arg Pro Lys Leu
                    355                 360                 365

Thr Asp Ser Phe Arg Gly Ile Ile Val Ile Pro Ala Glu Pro Ser Val
                    370                 375                 380

<210> SEQ ID NO 9
<211> LENGTH: 380
<212> TYPE: PRT
<213> ORGANISM: Lindera benzoin

<400> SEQUENCE: 9

Met Val Ala Thr Ser Leu Ala Ser Ala Phe Cys Ser Met Lys Ala Val
     1               5                  10                  15

Met Leu Ala Asp Asp Gly Arg Gly Met Lys Pro Arg Ser Ser Asp Leu
                     20                  25                  30

Gln Leu Arg Ala Gly Asn Ala Gln Thr Ser Leu Lys Met Ile Asp Gly
                     35                  40                  45
```

```
Thr Lys Phe Ser Tyr Thr Glu Ser Leu Lys Arg Leu Pro Asp Trp Ser
    50              55                  60
Lys Leu Leu Thr Val Ile Thr Thr Ile Phe Ser Ala Ala Glu Lys Gln
 65              70                  75                  80
Trp Thr Asn Leu Glu Arg Lys Pro Lys Pro Pro His Leu Leu Asp Asp
                 85                  90                  95
Arg Phe Gly Leu His Gly Leu Val Phe Arg Arg Thr Phe Ala Ile Arg
                100                 105                 110
Ser Tyr Glu Val Gly Pro Asp Arg Ser Ala Ser Ile Leu Ala Val Leu
                115                 120                 125
Asn His Leu Gln Glu Ala Thr Leu Asn His Ala Glu Ser Val Gly Ile
            130                 135                 140
Leu Gly Asp Arg Phe Gly Glu Thr Leu Glu Met Ser Lys Arg Asp Leu
145                 150                 155                 160
Met Trp Val Val Arg Arg Thr Tyr Val Ala Val Glu Arg Tyr Pro Ala
                165                 170                 175
Trp Gly Asp Thr Val Glu Ile Glu Ser Trp Ile Gly Ala Ser Gly Asn
                180                 185                 190
Asn Gly Met Arg Arg Glu Phe Leu Val Arg Asp Phe Lys Thr Gly Glu
            195                 200                 205
Ile Leu Thr Arg Cys Thr Ser Leu Ser Val Met Met Asn Thr Arg Thr
210                 215                 220
Arg Arg Leu Ser Lys Ile Pro Glu Glu Val Arg Gly Glu Ile Gly Pro
225                 230                 235                 240
Val Phe Ile Asp Asn Val Ala Val Lys Asp Glu Glu Ile Lys Lys Leu
                245                 250                 255
Gln Lys Leu Asn Asp Ser Thr Ala Asp Tyr Ile Gln Gly Gly Leu Ile
                260                 265                 270
Pro Arg Trp Asn Asp Leu Asp Leu Asn Gln His Val Asn Asn Ile Lys
            275                 280                 285
Tyr Val Ser Trp Ile Leu Glu Thr Val Pro Asp Ser Ile Leu Glu Ser
            290                 295                 300
Tyr His Met Ser Ser Ile Thr Leu Glu Tyr Arg Arg Glu Cys Thr Arg
305                 310                 315                 320
Asp Ser Val Leu Gln Ser Leu Thr Thr Val Ser Gly Gly Ser Ser Glu
                325                 330                 335
Ala Gly Leu Val Cys Glu His Ser Leu Leu Glu Gly Gly Ser Glu
                340                 345                 350
Val Leu Arg Ala Arg Thr Glu Trp Arg Pro Lys Leu Thr Asp Ser Phe
            355                 360                 365
Arg Gly Ile Ser Val Ile Pro Ala Glu Gln Ser Val
            370                 375                 380

<210> SEQ ID NO 10
<211> LENGTH: 418
<212> TYPE: PRT
<213> ORGANISM: Cuphea crassiflora

<400> SEQUENCE: 10

Met Val Ala Ala Ala Ser Ser Ala Phe Phe Pro Val Pro Ala Pro
 1               5                  10                  15
Gly Thr Ser Thr Lys Pro Arg Lys Ser Gly Asn Trp Pro Ser Arg Leu
                 20                  25                  30
Ser Pro Ser Ser Lys Pro Lys Ser Ile Pro Asn Gly Gly Phe Gln Val
                 35                  40                  45
```

Lys Ala Asn Ala Ser Ala His Pro Lys Ala Asn Gly Ser Ala Val Asn
 50                  55                  60

Leu Lys Ser Gly Ser Leu Asn Thr Gln Glu Asp Thr Ser Ser Ser Pro
 65                  70                  75                  80

Pro Pro Arg Ala Phe Leu Asn Gln Leu Pro Asp Trp Ser Met Leu Leu
                 85                  90                  95

Thr Ala Ile Thr Thr Val Phe Val Ala Ala Glu Lys Gln Trp Thr Met
            100                 105                 110

Leu Asp Arg Lys Ser Lys Arg Pro Asp Met Leu Val Asp Ser Val Gly
        115                 120                 125

Leu Lys Ser Ile Val Arg Asp Gly Leu Val Ser Arg Gln Ser Phe Ser
130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205

Pro Thr Trp Gly Asp Thr Val Glu Ile Asn Thr Trp Phe Ser Gln Ser
210                 215                 220

Gly Lys Ile Gly Met Gly Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
            260                 265                 270

Thr Pro His Phe Val Asp Ser Pro His Val Ile Glu Asp Asn Asp Arg
        275                 280                 285

Lys Leu His Lys Phe Asp Val Lys Thr Gly Asp Ser Ile Arg Lys Gly
290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335

Glu Thr Gln Glu Leu Cys Ser Leu Thr Val Glu Tyr Arg Arg Glu Cys
            340                 345                 350

Gly Met Asp Ser Lys Leu Glu Ser Val Thr Ala Met Asp Pro Ser Glu
        355                 360                 365

Glu Asp Gly Val Arg Ser Gln Tyr Asn His Leu Leu Arg Leu Glu Asp
370                 375                 380

Gly Thr Asp Val Val Lys Gly Arg Thr Glu Trp Arg Pro Lys Asn Ala
385                 390                 395                 400

Gly Thr Asn Gly Ala Ile Ser Thr Gly Lys Thr Ser Asn Gly Asn Ser
                405                 410                 415

Val Ser

<210> SEQ ID NO 11
<211> LENGTH: 415
<212> TYPE: PRT
<213> ORGANISM: Cuphea koehneana

<400> SEQUENCE: 11

```
Met Val Thr Ala Ala Ser Ser Ala Phe Phe Pro Val Pro Ala Pro
1               5                   10                  15

Gly Thr Ser Pro Lys Pro Gly Lys Ser Trp Pro Ser Ser Leu Ser Pro
            20                  25                  30

Ser Phe Lys Pro Lys Ser Ile Pro Asn Ala Gly Phe Gln Val Lys Ala
        35                  40                  45

Asn Ala Ser Ala His Pro Lys Ala Asn Gly Ser Ala Val Asn Leu Lys
50                  55                  60

Ser Gly Ser Leu Asn Thr Gln Glu Asp Thr Ser Ser Pro Pro
65                  70                  75              80

Arg Ala Phe Leu Asn Gln Leu Pro Asp Trp Ser Met Leu Leu Thr Ala
                85                  90                  95

Ile Thr Thr Val Phe Val Ala Ala Glu Lys Gln Trp Thr Met Arg Asp
                100                 105                 110

Arg Lys Ser Lys Arg Pro Asp Met Leu Val Asp Ser Val Gly Ser Lys
            115                 120                 125

Ser Ile Val Leu Asp Gly Leu Val Ser Arg Gln Ile Phe Ser Ile Arg
            130                 135                 140

Ser Tyr Glu Ile Gly Ala Asp Arg Thr Ala Ser Ile Glu Thr Leu Met
145                 150                 155                 160

Asn His Leu Gln Glu Thr Ser Ile Asn His Cys Lys Ser Leu Gly Leu
                165                 170                 175

Leu Asn Asp Gly Phe Gly Arg Thr Pro Gly Met Cys Lys Asn Asp Leu
                180                 185                 190

Ile Trp Val Leu Thr Lys Met Gln Ile Met Val Asn Arg Tyr Pro Thr
        195                 200                 205

Trp Gly Asp Thr Val Glu Ile Asn Thr Trp Phe Ser His Ser Gly Lys
        210                 215                 220

Ile Gly Met Ala Ser Asp Trp Leu Ile Thr Asp Cys Asn Thr Gly Glu
225                 230                 235                 240

Ile Leu Ile Arg Ala Thr Ser Val Trp Ala Met Met Asn Gln Lys Thr
                245                 250                 255

Arg Arg Phe Ser Arg Leu Pro Tyr Glu Val Arg Gln Glu Leu Thr Pro
                260                 265                 270

His Tyr Val Asp Ser Pro His Val Ile Glu Asp Asn Asp Arg Lys Leu
        275                 280                 285

His Lys Phe Asp Val Lys Thr Gly Asp Ser Ile Arg Lys Gly Leu Thr
        290                 295                 300

Pro Lys Trp Asn Asp Leu Asp Val Asn Gln His Val Asn Asn Val Lys
305                 310                 315                 320

Tyr Ile Gly Trp Ile Leu Glu Ser Met Pro Ile Glu Val Leu Glu Thr
                325                 330                 335

Gln Glu Leu Cys Ser Leu Thr Val Glu Tyr Arg Arg Glu Cys Gly Met
                340                 345                 350

Asp Ser Val Leu Glu Ser Val Thr Ala Met Asp Pro Ser Glu Asp Gly
            355                 360                 365

Gly Leu Ser Gln Tyr Lys His Leu Leu Arg Leu Glu Asp Gly Thr Asp
            370                 375                 380

Ile Val Lys Gly Arg Thr Glu Trp Arg Pro Lys Asn Ala Gly Thr Asn
385                 390                 395                 400

Gly Ala Ile Ser Thr Ala Lys Pro Ser Asn Gly Asn Ser Val Ser
                405                 410                 415
```

<210> SEQ ID NO 12
<211> LENGTH: 417
<212> TYPE: PRT
<213> ORGANISM: Cuphea leptopoda

<400> SEQUENCE: 12

```
Met Val Gly Ala Ala Ser Ser Ala Phe Phe Pro Ala Pro Ala Pro
1               5                   10                  15

Gly Thr Ser Pro Lys Pro Gly Lys Ser Gly Asn Trp Pro Ser Ser Leu
            20                  25                  30

Ser Pro Ser Leu Lys Pro Lys Ser Ile Pro Asn Gly Gly Phe Gln Val
            35                  40                  45

Lys Ala Asn Ala Ser Ala His Pro Lys Ala Asn Gly Ala Ala Val Asn
50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Thr Ala Ile Thr Thr Val Phe Val Ala Ala Glu Lys Gln Trp Thr Met
                100                 105                 110

Leu Asp Arg Lys Ser Lys Arg Pro Asp Met Leu Val Asp Ser Val Gly
            115                 120                 125

Leu Lys Asn Ile Val Arg Asp Gly Leu Val Ser Arg Gln Ser Phe Ser
130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
                180                 185                 190

Asp Leu Ile Trp Val Leu Thr Lys Met Gln Ile Leu Val Asn Arg Tyr
            195                 200                 205

Pro Ala Trp Gly Asp Thr Val Glu Ile Asn Thr Trp Phe Ser Gln Ser
210                 215                 220

Gly Lys Ile Gly Met Gly Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
            260                 265                 270

Thr Pro His Phe Val Asp Ser Pro His Val Ile Glu Asp Asn Asp Arg
            275                 280                 285

Lys Leu His Lys Phe Asp Val Lys Thr Gly Asp Ser Ile Arg Lys Gly
290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335

Glu Thr Gln Glu Leu Cys Ser Leu Thr Val Glu Tyr Arg Arg Glu Cys
            340                 345                 350

Gly Met Asp Ser Val Leu Glu Ser Val Thr Ala Arg Asp Pro Ser Glu
            355                 360                 365

Asp Gly Gly Arg Ser Gln Tyr Asn His Leu Leu Arg Leu Glu Asp Gly
370                 375                 380
```

```
Thr Asp Val Val Lys Gly Arg Thr Glu Trp Arg Ser Lys Asn Ala Gly
385                 390                 395                 400

Thr Asn Gly Ala Thr Ser Thr Ala Lys Thr Ser Asn Gly Asn Ser Val
            405                 410                 415

Ser

<210> SEQ ID NO 13
<211> LENGTH: 417
<212> TYPE: PRT
<213> ORGANISM: Cuphea angustifolia

<400> SEQUENCE: 13

Met Val Ala Ala Ala Ser Ser Ala Phe Phe Pro Val Pro Ala Pro
1               5                   10                  15

Gly Thr Ser Leu Lys Pro Gly Lys Ser Gly Asn Trp Pro Ser Ser Leu
                20                  25                  30

Ser Pro Ser Phe Lys Pro Lys Thr Ile Pro Ser Gly Gly Leu Gln Val
            35                  40                  45

Lys Ala Asn Ala Ser Ala His Pro Lys Ala Asn Gly Ser Ala Val Asn
50                  55                  60

Leu Lys Ser Gly Ser Leu Asp Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Thr Ala Ile Thr Thr Val Phe Val Ala Ala Glu Lys Gln Trp Thr Met
                100                 105                 110

Leu Asp Arg Lys Ser Lys Arg Pro Glu Met Leu Val Asp Ser Val Gly
            115                 120                 125

Leu Lys Ser Ser Val Arg Asp Gly Leu Val Ser Arg Gln Ser Phe Ser
130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205

Pro Thr Trp Gly Asp Thr Val Glu Val Asn Thr Trp Phe Ser Gln Ser
210                 215                 220

Gly Lys Ile Gly Met Ala Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
            260                 265                 270

Thr Pro His Tyr Val Asp Ser Pro His Val Ile Glu Asp Asn Asp Arg
        275                 280                 285

Lys Leu His Lys Phe Asp Val Lys Thr Gly Asp Ser Ile Arg Lys Gly
290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335
```

```
Glu Thr Gln Glu Leu Cys Ser Leu Thr Val Glu Tyr Arg Arg Glu Cys
                340                 345                 350

Gly Met Asp Ser Val Leu Glu Ser Val Thr Ala Met Asp Pro Ser Glu
            355                 360                 365

Asp Gly Gly Val Ser Gln Tyr Lys His Leu Leu Arg Leu Glu Asp Gly
        370                 375                 380

Thr Asp Ile Val Lys Gly Arg Thr Glu Trp Arg Pro Lys Asn Ala Gly
385                 390                 395                 400

Thr Asn Gly Ala Thr Ser Lys Ala Lys Thr Ser Asn Gly Asn Ser Val
                405                 410                 415

Ser
```

<210> SEQ ID NO 14
<211> LENGTH: 417
<212> TYPE: PRT
<213> ORGANISM: Cuphea llavea

<400> SEQUENCE: 14

```
Met Val Ala Ala Ala Ser Ser Ala Phe Phe Pro Ala Pro Ala Pro
1               5                   10                  15

Gly Ser Ser Pro Lys Pro Gly Lys Pro Gly Asn Trp Pro Ser Ser Leu
                20                  25                  30

Ser Pro Ser Phe Lys Pro Lys Ser Ile Pro Asn Gly Arg Phe Gln Val
            35                  40                  45

Lys Ala Asn Ala Ser Ala His Pro Lys Ala Asn Gly Ser Ala Val Asn
        50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Ser Ala Ile Thr Thr Val Phe Val Ala Ala Glu Lys Gln Trp Thr Met
                100                 105                 110

Leu Asp Arg Lys Ser Lys Arg Pro Asp Met Leu Val Asp Ser Val Gly
            115                 120                 125

Leu Lys Asn Ile Val Arg Asp Gly Leu Val Ser Arg Gln Ser Phe Ser
        130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205

Pro Ala Trp Gly Asp Thr Val Glu Ile Asn Thr Trp Phe Ser Gln Ser
210                 215                 220

Gly Lys Ile Gly Met Gly Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
            260                 265                 270

Thr Pro His Phe Val Asp Ser Pro His Val Ile Glu Asp Asn Asp Arg
        275                 280                 285
```

-continued

Lys Leu His Lys Phe Asp Val Lys Thr Gly Asp Ser Ile Arg Lys Gly
    290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335

Glu Thr Gln Glu Leu Cys Ser Leu Thr Val Glu Tyr Arg Arg Glu Cys
            340                 345                 350

Gly Met Asp Ser Val Leu Glu Ser Val Thr Ala Ile Asp Pro Ser Glu
        355                 360                 365

Asp Gly Gly Arg Ser Gln Tyr Asn His Leu Leu Arg Leu Asp Asp Gly
    370                 375                 380

Thr Asp Val Val Lys Gly Arg Thr Glu Trp Arg Pro Lys Asn Ala Gly
385                 390                 395                 400

Thr Asn Gly Ala Ile Ser Thr Gly Lys Thr Ser Asn Gly Asn Ser Val
                405                 410                 415

Ser

<210> SEQ ID NO 15
<211> LENGTH: 417
<212> TYPE: PRT
<213> ORGANISM: Cuphea lophostoma

<400> SEQUENCE: 15

Met Val Ala Ala Ala Ser Ser Ala Phe Phe Pro Val Pro Ala Pro
1               5                   10                  15

Gly Thr Ser Leu Lys Pro Trp Lys Ser Gly Asn Trp Pro Ser Ser Leu
                20                  25                  30

Ser Pro Ser Phe Lys Pro Lys Thr Ile Pro Ser Gly Gly Phe Gln Val
            35                  40                  45

Lys Ala Asn Ala Ser Ala Gln Pro Lys Ala Asn Gly Ser Ala Val Asn
        50                  55                  60

Leu Lys Ser Gly Ser Leu Asn Thr Gln Glu Asp Thr Thr Ser Ser Pro
65                  70                  75                  80

Pro Pro Arg Ala Phe Leu Asn Gln Leu Pro Asp Trp Ser Met Leu Leu
                85                  90                  95

Thr Ala Ile Thr Thr Val Phe Val Ala Ala Glu Lys Gln Trp Thr Met
            100                 105                 110

Leu Asp Arg Lys Ser Lys Arg Pro Glu Lys Leu Val Asp Ser Val Gly
        115                 120                 125

Leu Lys Ser Ser Val Arg Asp Gly Leu Val Ser Arg Gln Ser Phe Ser
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205

Pro Thr Trp Gly Asp Thr Val Glu Ile Asn Thr Trp Phe Ser Gln Ser
    210                 215                 220

Gly Lys Ile Gly Met Ala Ser Asp Trp Leu Ile Ser Asp Cys Asn Thr
225                 230                 235                 240

```
Gly Glu Ile Leu Ile Arg Ala Thr Ser Val Trp Ala Met Met Asn Gln
            245                 250                 255

Lys Thr Arg Arg Phe Ser Arg Leu Pro Tyr Glu Val Arg Gln Glu Leu
        260                 265                 270

Thr Pro His Tyr Val Asp Ser Pro His Val Ile Glu Asp Asn Asp Arg
    275                 280                 285

Lys Leu His Lys Phe Asp Val Lys Thr Gly Asp Ser Ile Arg Lys Gly
290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335

Glu Thr Gln Glu Leu Cys Ser Leu Thr Val Glu Tyr Arg Arg Glu Cys
            340                 345                 350

Gly Met Asp Ser Val Leu Glu Ser Val Thr Ala Met Asp Pro Ser Glu
        355                 360                 365

Asp Glu Gly Arg Ser Gln Tyr Lys His Leu Leu Arg Leu Glu Asp Gly
    370                 375                 380

Thr Asp Ile Val Lys Gly Arg Thr Glu Trp Arg Pro Lys Asn Ala Gly
385                 390                 395                 400

Thr Asn Gly Ala Ile Ser Thr Ala Lys Asn Ser Asn Gly Asn Ser Val
                405                 410                 415

Ser

<210> SEQ ID NO 16
<211> LENGTH: 384
<212> TYPE: PRT
<213> ORGANISM: Sassafras albidum

<400> SEQUENCE: 16

Met Ala Thr Thr Ser Leu Ala Ser Ala Phe Cys Ser Met Lys Ala Val
1               5                   10                  15

Met Leu Ala Arg Asp Gly Arg Gly Met Lys Pro Arg Ser Ser Asp Leu
            20                  25                  30

Gln Leu Arg Ala Gly Asn Ala Gln Thr Pro Leu Lys Met Ile Asn Gly
        35                  40                  45

Thr Lys Phe Ser Tyr Thr Glu Ser Leu Lys Arg Leu Pro Asp Trp Ser
    50                  55                  60

Met Leu Phe Ala Val Ile Thr Thr Ile Phe Ser Val Ala Glu Lys Gln
65                  70                  75                  80

Trp Thr Asn Leu Glu Trp Lys Pro Lys Pro Lys Pro Arg Leu Pro Gln
                85                  90                  95

Leu Leu Asp Asp His Phe Gly Leu His Gly Leu Val Phe Arg Arg Thr
            100                 105                 110

Phe Ala Ile Arg Ser Tyr Glu Val Gly Pro Asp Arg Ser Thr Ser Ile
        115                 120                 125

Val Ala Val Met Asn His Leu Gln Glu Ala Thr Leu Asn His Ala Lys
    130                 135                 140

Ser Val Gly Ile Leu Gly Asp Gly Phe Gly Thr Thr Leu Glu Met Ser
145                 150                 155                 160

Lys Arg Asp Leu Ala Trp Val Val Arg Arg Thr His Val Ala Val Glu
                165                 170                 175

Arg Tyr Pro Ala Trp Gly Asp Thr Val Glu Val Glu Cys Trp Ile Gly
            180                 185                 190
```

```
Ala Ser Gly Asn Asn Gly Met Arg Arg Asp Phe Leu Val Arg Asp Cys
            195                 200                 205

Lys Thr Gly Glu Ile Leu Thr Arg Cys Thr Ser Leu Ser Val Met Met
210                 215                 220

Asn Thr Arg Thr Arg Arg Leu Ser Lys Ile Pro Glu Glu Val Arg Gly
225                 230                 235                 240

Glu Ile Gly Pro Leu Phe Ile Asp Asn Val Ala Val Lys Asp Glu Glu
            245                 250                 255

Ile Lys Lys Leu Gln Lys Leu Asn Asp Ser Ser Ala Asp Tyr Ile Gln
            260                 265                 270

Gly Gly Leu Thr Pro Arg Trp Asn Asp Leu Asp Val Asn Gln His Val
            275                 280                 285

Asn Asn Ile Lys Tyr Val Gly Trp Ile Leu Glu Thr Val Pro Asp Ser
290                 295                 300

Ile Phe Glu Ser His His Ile Ser Ser Ile Thr Leu Glu Tyr Arg Arg
305                 310                 315                 320

Glu Cys Thr Arg Asp Ser Val Leu Gln Ser Leu Thr Val Ser Gly
            325                 330                 335

Gly Ser Leu Glu Ala Gly Leu Val Cys Asp His Leu Leu Gln Leu Glu
            340                 345                 350

Gly Gly Ser Glu Val Leu Arg Ala Arg Thr Glu Trp Arg Pro Lys Leu
            355                 360                 365

Thr Asp Ser Phe Arg Gly Ile Ile Val Ile Pro Ala Glu Pro Ser Val
            370                 375                 380

<210> SEQ ID NO 17
<211> LENGTH: 384
<212> TYPE: PRT
<213> ORGANISM: Sassafras albidum

<400> SEQUENCE: 17

Met Ala Thr Thr Ser Leu Ala Ser Ala Phe Cys Ser Met Lys Ala Val
1               5                   10                  15

Met Leu Ala Arg Asp Gly Arg Gly Met Lys Pro Arg Ser Ser Asp Leu
            20                  25                  30

Gln Leu Arg Ala Gly Asn Ala Gln Thr Pro Leu Lys Met Ile Asn Gly
            35                  40                  45

Thr Lys Phe Ser Tyr Thr Glu Ser Leu Lys Arg Leu Pro Asp Trp Ser
        50                  55                  60

Met Leu Phe Ala Val Ile Thr Thr Ile Phe Ser Val Ala Glu Lys Gln
65                  70                  75                  80

Trp Thr Asn Leu Glu Trp Lys Pro Lys Pro Lys Pro Arg Leu Pro Gln
            85                  90                  95

Leu Leu Asp Asp His Phe Gly Leu His Gly Leu Val Phe Arg Arg Thr
            100                 105                 110

Phe Ala Ile Arg Ser Tyr Glu Val Gly Pro Asp Arg Ser Thr Ser Ile
            115                 120                 125

Val Ala Val Met Asn His Leu Gln Glu Ala Thr Leu Asn His Ala Lys
130                 135                 140

Ser Val Gly Ile Leu Gly Asp Gly Phe Gly Thr Thr Leu Glu Met Ser
145                 150                 155                 160

Lys Arg Asp Leu Ala Trp Val Val Arg Arg Thr His Val Ala Val Glu
            165                 170                 175

Arg Tyr Pro Ala Trp Gly Asp Thr Val Glu Val Glu Ala Trp Val Gly
```

```
            180                 185                 190
Ala Ser Gly Asn Ile Gly Met Arg Arg Asp Phe Leu Val Arg Asp Cys
            195                 200                 205
Lys Thr Gly His Ile Leu Ala Arg Cys Thr Ser Val Ser Val Met Met
            210                 215                 220
Asn Ala Arg Thr Arg Arg Leu Ser Lys Ile Pro Gln Glu Val Arg Ala
225                 230                 235                 240
Glu Ile Asp Pro Leu Phe Ile Glu Lys Val Ala Val Lys Glu Gly Glu
                245                 250                 255
Ile Lys Lys Leu Gln Lys Phe Asn Asp Ser Thr Ala Asp Tyr Ile Gln
            260                 265                 270
Gly Gly Trp Thr Pro Arg Trp Asn Asp Leu Asp Val Asn Gln His Val
            275                 280                 285
Asn Asn Ile Lys Tyr Ile Gly Trp Ile Phe Lys Ser Val Pro Asp Ser
            290                 295                 300
Ile Ser Glu Asn His Tyr Leu Ser Ser Ile Thr Leu Glu Tyr Arg Arg
305                 310                 315                 320
Glu Cys Thr Arg Gly Ser Ala Leu Gln Ser Leu Thr Val Cys Gly
                325                 330                 335
Asp Ser Ser Glu Ala Gly Ile Ile Cys Glu His Leu Leu Gln Leu Glu
            340                 345                 350
Asp Gly Pro Glu Val Leu Arg Ala Arg Thr Glu Trp Arg Pro Lys Leu
            355                 360                 365
Thr Asp Ser Phe Arg Gly Ile Ile Val Ile Pro Ala Glu Pro Ser Val
370                 375                 380

<210> SEQ ID NO 18
<211> LENGTH: 380
<212> TYPE: PRT
<213> ORGANISM: Lindera benzoin

<400> SEQUENCE: 18

Met Val Ala Thr Ser Leu Ala Ser Ala Phe Cys Ser Met Lys Ala Val
1               5                   10                  15
Met Leu Ala Asp Asp Gly Arg Gly Met Lys Pro Arg Ser Ser Asp Leu
            20                  25                  30
Gln Leu Arg Ala Gly Asn Ala Gln Thr Ser Leu Lys Met Ile Asp Gly
        35                  40                  45
Thr Lys Phe Ser Tyr Thr Glu Ser Leu Lys Arg Leu Pro Asp Trp Ser
50                  55                  60
Lys Leu Leu Thr Val Ile Thr Thr Ile Phe Ser Ala Ala Glu Lys Gln
65                  70                  75                  80
Trp Thr Asn Leu Glu Arg Lys Pro Lys Pro Pro His Leu Leu Asp Asp
                85                  90                  95
Arg Phe Gly Leu His Gly Leu Val Phe Arg Arg Thr Phe Ala Ile Arg
            100                 105                 110
Ser Tyr Glu Val Gly Pro Asp Arg Ser Ala Ser Ile Leu Ala Val Leu
        115                 120                 125
Asn His Leu Gln Glu Ala Thr Leu Asn His Ala Glu Ser Val Gly Ile
    130                 135                 140
Leu Gly Asp Arg Phe Gly Glu Thr Leu Glu Met Ser Lys Arg Asp Leu
145                 150                 155                 160
Met Trp Val Val Arg Arg Thr Tyr Val Ala Val Glu Arg Tyr Pro Ala
                165                 170                 175
```

```
Trp Gly Asp Thr Val Glu Ile Glu Ser Trp Ile Ala Ser Gly Asn
            180                 185                 190

Asn Gly Met Arg Arg Glu Phe Leu Val Arg Asp Phe Lys Thr Gly Glu
        195                 200                 205

Ile Leu Thr Arg Cys Thr Ser Leu Ser Val Met Met Asn Thr Arg Thr
    210                 215                 220

Arg Arg Leu Ser Lys Ile Pro Glu Glu Val Arg Gly Glu Ile Gly Pro
225                 230                 235                 240

Val Phe Ile Asp Asn Val Ala Val Lys Asp Glu Ile Lys Lys Leu
            245                 250                 255

Gln Lys Leu Asn Asp Ser Thr Ala Asp Tyr Ile Gln Gly Gly Leu Ile
        260                 265                 270

Pro Arg Trp Asn Asp Leu Asp Leu Asn Gln His Val Asn Asn Ile Lys
    275                 280                 285

Tyr Val Ser Trp Ile Leu Glu Thr Val Pro Asp Ser Ile Leu Glu Ser
        290                 295                 300

Tyr His Met Ser Ser Ile Thr Leu Glu Tyr Arg Arg Glu Cys Thr Arg
305                 310                 315                 320

Asp Ser Val Leu Gln Ser Leu Thr Thr Val Ser Gly Gly Ser Ser Glu
            325                 330                 335

Ala Gly Leu Val Cys Glu His Ser Leu Leu Leu Glu Gly Gly Ser Glu
        340                 345                 350

Val Leu Arg Ala Arg Thr Glu Trp Arg Pro Lys Leu Thr Asp Ser Phe
    355                 360                 365

Arg Gly Ile Ser Val Ile Pro Ala Glu Gln Ser Val
370                 375                 380

<210> SEQ ID NO 19
<211> LENGTH: 1257
<212> TYPE: DNA
<213> ORGANISM: Cuphea crassiflora

<400> SEQUENCE: 19
atggtggctg ctgcagcaag ttctgcattc ttccctgttc ctgccccagg aacctccact      60
aaacccagga agtccggcaa ttggccatcg agattgagcc cttcctccaa gcccaagtca     120
atccccaatg gcggatttca ggttaaggca aatgccagtg cccatcctaa ggctaacggt     180
tctgcagtaa atctaaagtc tggcagcctc aacactcagg aggacacttc gtcgtcccct     240
cctcctcggg ctttccttaa ccagttgcct gattggagta tgcttctgac tgcaatcacg     300
accgttttcg tggcggcaga gaagcagtgg acaatgcttg atcggaaatc taagaggcct     360
gacatgctcg tggactcggt tgggttgaag agtattgttc gggatgggct cgtgtccaga     420
caaagttttt cgatcaggtc ttatgaaata ggcgctgatc gaacagcctc tatagagacg     480
ctgatgaacc acttgcagga acatctatt aatcattgta agagtttggg ccttctcaat     540
gacggctttg gtcggactcc tgggatgtgt aaaaacgacc tcatttgggt gcttacaaaa     600
atgcagatca tggtgaatcg ctacccaact ggggcgata ctgttgagat caatacctgg     660
ttctcccagt cggggaaaat cggtatgggt agcgattggc taataagtga ttgcaataca     720
ggagaaattc ttataagggc aacgagcgtg tgggccatga tgaatcaaaa gacgagaaga     780
ttctcaagac ttccatacga ggttcgccag gagttaacgc tcattttgt ggactctcct     840 catgtcattg aagacaatga tcggaaattg cataagtttg atgtgaagac tggcgattct     900
attcgcaagg gtctaactcc gaggtggaat gatttggatg tcaatcagca cgtaagcaac     960
```

```
gtgaagtaca ttgggtggat tctcgagagt atgccaatag aagttctgga gacccaggag   1020
ctatgctctc tgacagttga atataggcgg gaatgcggaa tggacagtaa gctggagtcc   1080
gtgactgcta tggatccctc agaagaagat ggagtccggt ctcagtacaa tcaccttctg   1140
cggcttgagg atgggactga tgtcgtgaag ggcagaactg agtggcgacc gaagaatgca   1200
ggaactaacg gggcgatatc aacaggaaag acttcaaatg gaaactcggt ttcttag     1257
```

<210> SEQ ID NO 20
<211> LENGTH: 1248
<212> TYPE: DNA
<213> ORGANISM: Cuphea koehneana

<400> SEQUENCE: 20

```
atggtcactg ctgcagcaag ttctgcattc ttccctgttc cagccccggg aacctcccct     60
aaacccggga agtcctggcc atcgagcttg agcccttcct tcaagcccaa gtcaatcccc    120
aatgccggat ttcaggttaa ggcaaatgcc agtgcccatc ctaaggctaa cggttctgca    180
gtaaatctaa agtctggcag cctcaacact caggaggaca cttcgtcgtc cctcctcct     240 cgggctttcc ttaaccagtt gcctgattgg agtatgcttc tgactgcaat cacgaccgtc    300
ttcgtggcgg cagagaagca gtggactatg cgtgatcgga atctaagag gcctgacatg     360 ctcgtggact cggttggatc gaagagtatt gttctggatg gctcgtgtc cagacagatt     420 ttttcgatta gatcttatga aataggcgct gatcgaacag cctctataga gacgctgatg    480
aaccacttgc aggaaacatc tatcaatcat gtaagagtt tgggtcttct caatgacggc     540
tttggtcgta ctcctgggat gtgtaaaaac gacctcattt gggtgcttac aaaaatgcag    600
atcatggtga atcgctaccc aacttggggc gatactgttg agatcaatac ctggttctcc    660
cattcgggga aaatcggtat ggctagcgat tggctaataa ctgattgcaa cacaggagaa    720
attcttataa gagcaacgag cgtgtgggcc atgatgaatc aaaagacgag aagattctca    780
agacttccat acgaggttcg ccaggagtta acgcctcatt atgtggactc tcctcatgtc    840
attgaagata tgatcggaa attgcataag tttgatgtga agactggtga ttccattcgt     900
aagggtctaa ctccgaagtg gaatgacttg gatgtcaatc agcacgtcaa caacgtgaag   960
tacatcgggt ggattctcga gagtatgcca atagaagttt tggagactca ggagctatgc   1020
tctctcaccg ttaatatag gcgggaatgc ggaatggaca gtgtgctgga gtccgtgact    1080
gctatggatc cctcagaaga tggaggccta tctcagtaca agcaccttct gcggcttgag   1140
gatgggactg acatcgtgaa gggcagaact gagtggcgac cgaagaatgc aggaactaac   1200
ggggcgatat caacagcaaa gccttcaaat ggaaactcgg tctcttag                1248
```

<210> SEQ ID NO 21
<211> LENGTH: 1254
<212> TYPE: DNA
<213> ORGANISM: Cuphea leptopoda

<400> SEQUENCE: 21

```
atggtgggtg ctgcagcaag ttctgcattc ttccctgctc cagccccggg aacctcccct     60
aaacccggga agtccggcaa ttggccatca agcttgagcc cttccttaaa gcccaagtca    120
atccccaatg gcggatttca ggttaaggca aatgccagtg cccatcctaa ggctaacggt    180
gctgcagtaa atctaaagtc tggcagcctc aacactcagg aggacacttc gtcgtccct     240 cctcctcggg ctttccttaa ccagttgcct gattggagta tgcttctgac tgcaatcacg    300
accgtcttcg tggcggcaga gaagcagtgg actatgcttg atcggaaatc taagaggcct   360
```

```
gacatgctcg tggactcggt tgggttgaag aatattgttc gggatgggct cgtgtccaga    420
cagagttttt cgatcaggtc ttatgaaata ggcgctgatc gaacagcctc tatagagacg    480
ctgatgaacc acttgcagga aacatctatc aatcattgta agagtttggg tcttctcaat    540
gacggctttg tcgtactcc tgggatgtgt aaaaacgacc tcatttgggt gcttacaaaa     600
atgcagatcc tggtgaatcg ctacccagct ggggagata ctgttgagat caatacctgg     660
ttctctcagt cggggaaaat cggcatgggt agtgattggc taataagtga ttgcaacaca    720
ggagaaattc ttataagagc aacgagcgtg tgggcaatga tgaatcaaaa gacgagaaga    780
ttctcaagac ttccatacga ggttcgccag gagttaacgc ctcattttgt agactcacct    840
catgtcattg aagacaatga tcggaaattg cataagtttg atgtgaagac tggtgattct    900
attcgcaagg gtctaactcc gaggtggaat gacttggatg tcaatcaaca cgtaagcaac    960
gtgaagtaca ttgggtggat tctcgagagt atgccaatag aagttttgga gactcaggag    1020
ctatgctctc tcaccgttga atataggcgg gaatgcggaa tggacagtgt gctggagtcc    1080
gtgactgcta gggatccctc agaagatgga ggccggtctc agtacaatca ccttctgcgg    1140
cttgaggatg ggactgatgt cgtgaagggc agaactgagt ggcgatcgaa gaatgcagga    1200
actaacgggg cgacatcaac agcaaagact tcaaatggaa actcggtctc ttag          1254
```

<210> SEQ ID NO 22
<211> LENGTH: 1254
<212> TYPE: DNA
<213> ORGANISM: Cuphea angustifolia

<400> SEQUENCE: 22

```
atggtggctg ctgcagcaag ttctgcattc ttccctgttc cagccccggg aacatccctt    60
aaacccggga agtccggcaa ttggccatcg agcttgagcc cttccttcaa gcccaagaca    120
atccccagtg gcggacttca ggttaaggca aatgccagtg cccatcctaa ggctaacggt    180
tctgcagtaa atctaaagtc tggcagcctc gacactcagg aggacacttc gtcgtcccct    240
cctcctcggg ctttccttaa ccagttgcct gattggagta tgcttctgac tgcaatcacg    300
accgtcttcg tggcggcaga aagcagtgg actatgcttg ataggaaatc taagaggcct    360
gaaatgctcg tggactcggt tgggttgaag agtagtgttc gggatgggct cgtgtccaga    420
cagagttttt cgattaggtc ttatgaaata ggcgctgatc gaacagcctc tatagagacg    480
ctgatgaacc acttgcagga aacatctatc aatcattgta agagtttggg tcttctcaac    540
gatggctttg tcgtactcc tgggatgtgt aaaaacgacc tcatttgggt gcttacaaaa     600
atgcagatca tggtgaatcg ctacccaact ggggcgata ctgttgaggt caatacctgg     660
ttctcccagt cggggaaaat cggtatggct agcgattggc taatcagtga ttgcaacaca    720
ggagaaattc ttataagagc aacaagcgtg tgggccatga tgaatcaaaa gacgagaaga    780
ttctcaagac ttccatacga ggttcgccag gagctaacac ctcattatgt ggactctcct    840
catgtcattg aagataatga tcggaaattg cataagtttg atgtgaagac tggtgattcc    900
attcgcaagg gtctaactcc gaggtggaat gacttggatg tcaatcagca cgtaagcaac    960
gtgaagtaca ttgggtggat tcttgagagt atgccaatag aagttttgga gacccaggag    1020
ctatgctctc tcaccgttga atataggcgg gaatgcggaa tggacagtgt gctggagtcc    1080
gtgactgcta tggatccctc agaagatgga ggcgtgtctc agtacaagca ccttctgcgg    1140
cttgaggatg ggactgatat cgtgaagggc agaactgaat ggcgaccgaa gaatgcagga    1200
```
actaatgggg cgacatcaaa agcaaagact tcaaatggaa actcggtctc ttag      1254

<210> SEQ ID NO 23
<211> LENGTH: 1254
<212> TYPE: DNA
<213> ORGANISM: Cuphea llavea

<400> SEQUENCE: 23
atggtggctg ctgcagcaag ttctgcattc ttccctgctc cagccccggg atcctcacct      60
aaacccggga agcccggtaa ttggccatcg agcttgagcc cttccttcaa gcccaagtca     120
atccccaatg gccgatttca ggttaaggca aatgcgagtg cccatcctaa ggctaacggt     180
tctgcagtaa atctaaagtc tggcagcctc aacactcagg aggacacttc gtcgtcccct     240
cctcctcggg ctttccttaa ccagttgcct gattggagta tgcttctgtc tgcaatcacg     300
actgtattcg tggcggcaga aagcagtgg actatgcttg atcggaaatc taagaggcct     360
gacatgcttg tggactcggt tgggttgaag aatattgttc gggatgggct cgtgtccaga     420
cagagttttt cgattagatc ttatgaaata ggcgctgatc gaacagcttc tatagagaca     480
ctgatgaacc acttgcagga acatctatc aatcattgta gagtttggg tcttctcaat     540 gacggctttg tcgtactcc tgggatgtgt aaaaacgacc tcatttgggt gcttacaaaa     600
atgcagatca tggtgaatcg ctacccagct tggggcgata ctgttgagat caatacatgg     660
ttctcccagt cggggaaaat cggtatgggt agcgattggc taataagtga ttgcaacaca     720
ggagaaattc ttataagagc aacgagcgtg tgggccatga tgaatcaaaa gacgagaaga     780
ttctcaagac ttccatatga ggttcgccag gagttaacgc tcatttttgt ggactctcct     840
catgtcattg aagacaatga tcggaaattg cataagttcg atgtgaagac tggtgattct     900
attcgcaagg tctaactcc gaggtggaat gacttggatg tcaatcaaca cgtaagcaac     960
gtgaagtaca ttgggtggat tctcgagagt atgccaatag aagttttgga gacccaggaa    1020
ctatgctctc tcacagttga atataggcgg gaatgcggaa tggacagtgt gctggagtcc    1080
gtgactgcta tagatccctc agaagatgga gggcggtctc agtacaatca ccttctgcgg    1140
cttgatgatg ggactgatgt cgtgaagggc agaacagagt ggcgaccgaa gaatgcagga    1200
actaacgggg cgatatcaac aggaaagact tcaaatggga actcggtctc ctag         1254

<210> SEQ ID NO 24
<211> LENGTH: 1254
<212> TYPE: DNA
<213> ORGANISM: Cuphea lophostoma

<400> SEQUENCE: 24
atggtggctg ctgcagcaag ttctgcattc ttccctgttc cagccccggg aacctccctt      60
aaaccctgga agtccggaaa ttggccatcg agcttgagcc cttccttcaa gcccaagaca     120
atccccagtg gcggatttca ggttaaggca aatgccagtg cccagcctaa ggctaacggt     180
tctgcagtaa atctaaagtc tggcagcctc aacactcagg aggacacaac gtcgtcgcct     240
cctcctcggg ctttccttaa ccagttgcct gattggagta tgcttctgac tgcaatcacg     300
accgtcttcg tggcggcgga aagcagtgg acaatgcttg ataggaaatc taagaggcct     360
gaaaagctcg tggactcggt tgggttgaag agtagtgttc gggatgggct cgtgtccaga     420
cagagttttt cgattaggtc ttatgaaata ggcgctgatc gaacagcctc tatagagacg     480
ttgatgaacc acttgcagga acatctatc aatcattgta gagtttggg tcttctcaac     540 gacggctttg tcgtactcc tgggatgtgt aaaaacgacc tcatttgggt gcttacgaaa     600

| | |
|---|---|
| atgcagatca tggtgaatcg ctacccaact tggggcgata ctgttgagat caatacctgg | 660 |
| ttctcccagt cggggaaaat cggtatggct agcgattggc taataagtga ttgcaacaca | 720 |
| ggagaaattc ttataagagc aacgagcgtg tgggccatga tgaatcaaaa gacgagaagg | 780 |
| ttctcaagac ttccatacga ggttcgccag gagttaacgc ctcattatgt ggactctcct | 840 |
| catgtcattg aagacaatga tcggaaattg cataagtttg atgtgaagac tggtgattcc | 900 |
| attcgcaagg gtctgactcc gaggtggaat gacttggatg tcaatcagca cgtaagcaac | 960 |
| gtgaagtaca ttgggtggat tctggagagt atgccaatag aagttttgga gacccaggag | 1020 |
| ctatgctctc tcaccgttga atataggcgg gaatgcggga tggacagtgt gctggagtcc | 1080 |
| gtgactgcta tggatccctc agaagatgaa ggccggtctc agtacaagca ccttctgcgg | 1140 |
| cttgaggatg ggactgatat cgtgaagggc agaactgagt ggcgaccgaa gaatgcagga | 1200 |
| actaacgggg cgatatcaac agcaaagaat tcaaatggaa actcggtctc ttag | 1254 |

<210> SEQ ID NO 25
<211> LENGTH: 1155
<212> TYPE: DNA
<213> ORGANISM: Sassafras albidum

<400> SEQUENCE: 25

| | |
|---|---|
| atggccacca cctctttagc ttctgctttc tgctcgatga aagctgtaat gttggctcgt | 60 |
| gatggcaggg gcatgaaacc caggagcagt gatttgcagc tgagggcggg aaatgcacaa | 120 |
| acccctttga agatgatcaa tgggaccaag ttcagttaca cggagagctt gaaaaggttg | 180 |
| cctgactgga gcatgctctt tgcagtgatc acaaccatct tttcggttgc tgagaagcag | 240 |
| tggaccaatc tagagtggaa gccgaagccg aagccgaggc tacccccagtt gcttgatgac | 300 |
| catttttggac tgcatgggtt agttttcagg cgcacctttg ccatcagatc ttatgaggtc | 360 |
| ggacctgacc gctccacatc tatagtggct gttatgaatc acttgcagga ggctacactt | 420 |
| aatcatgcga agagtgtggg aattctagga gatggattcg gtacgacgct agagatgagt | 480 |
| aagagagatc tggcgtgggt tgtgagacgc acgcatgttg ctgtggaacg gtaccctgct | 540 |
| tggggtgata ctgttgaagt agagtgctgg attggtgcat ctggaaataa tggcatgcgc | 600 |
| cgtgatttcc ttgtccggga ctgcaaaaca ggcgaaattc ttacaagatg taccagtctt | 660 |
| tcggtgatga tgaatacaag gacaaggagg ttgtccaaaa tccctgaaga agttagaggg | 720 |
| gagatagggc ctctattcat tgataatgtg gctgtcaagg acgaggaaat taagaaacta | 780 |
| cagaagctca atgacagctc tgcagattac atccaaggag gtttgactcc tcgatggaat | 840 |
| gatttggatg tcaatcagca tgttaacaac atcaaatacg ttggctggat tcttgagact | 900 |
| gtcccagact ccatctttga gagtcatcat atttccagca tcactcttga atacaggaga | 960 |
| gagtgcacca gggatagcgt gctgcagtcc ctgaccactg tctccggtgg ctcgttggag | 1020 |
| gctgggttag tgtgcgatca cttgctccag cttgaaggtg gtctgaggt attgagggca | 1080 |
| agaacagagt ggaggcctaa gcttaccgat agtttcagag ggattattgt gatacccgca | 1140 |
| gaaccgagtg tgtaa | 1155 |

<210> SEQ ID NO 26
<211> LENGTH: 1155
<212> TYPE: DNA
<213> ORGANISM: Sassafras albidum

<400> SEQUENCE: 26

```
atggccacca cctctttagc ttctgctttc tgctcgatga aagctgtaat gttggctcgt      60
gatggcaggg gcatgaaacc caggagcagt gatttgcagc tgagggcggg aaatgcacaa     120
accccttga agatgatcaa tgggaccaag ttcagttaca cggagagctt gaaaaggttg     180
cctgactgga gcatgctctt tgcagtgatc acaaccatct tttcggttgc tgagaagcag     240
tggaccaatc tagagtggaa gccgaagccg aagccgaggc taccccagtt gcttgatgac     300
catttggac tgcatgggtt agttttcagg cgcacctttg ccatcagatc ttatgaggtc     360
ggacctgacc gctccacatc tatagtggct gttatgaatc acttgcagga ggctacactt     420
aatcatgcga gagtgtgggg aattctagga gatggattcg gtacgacgct agagatgagt     480
aagagagatc tggcgtgggt tgtgagacgc acgcatgttg ctgtggaacg gtaccccgct     540
tggggcgata ctgttgaagt cgaggcctgg gtcggtgcat ctggaaacat ggcatgcgc     600
cgcgattttc ttgtccgcga ctgcaaaact ggccacattc ttgcaagatg taccagtgtt     660
tcagtgatga tgaatgcgag gacacggaga ttgtccaaaa ttccccaaga agttagagcc     720
gagattgacc ctcttttcat tgaaaaggtt gcggtcaagg aaggggaaat taagaaatta     780
cagaagttca tgatagcac tgcagattac attcaagggg gttggactcc tcgatggaat     840
gatttggatg tcaatcagca cgtgaacaat atcaaataca ttggctggat ttttaagagc     900
gtcccagact ctatctctga gaatcattat cttttctagca tcactctcga atacaggaga     960
gagtgcacaa ggggcagcgc gctgcagtcc ctgaccactg tttgtggtga ctcgtcggaa    1020
gctgggatca tatgtgagca cctactccag cttgaggatg ggcctgaggt tttgagggca    1080
agaacagagt ggaggcctaa gcttaccgat agtttcagag ggattattgt gatacccgca    1140
gaaccgagtg tgtaa                                                     1155
```

<210> SEQ ID NO 27
<211> LENGTH: 1248
<212> TYPE: DNA
<213> ORGANISM: Lindera benzoin

<400> SEQUENCE: 27

```
atggtcactg ctgcagcaag ttctgcattc ttccctgttc cagccccggg aacctcccct      60
aaacccggga gtcctggcc atcgagcttg agcccttcct tcaagcccaa gtcaatcccc     120
aatgccggat tcaggttaa ggcaaatgcc agtgcccatc ctaaggctaa cggttctgca     180
gtaaatctaa agtctggcag cctcaacact caggaggaca cttcgtcgtc ccctcctcct     240
cgggctttcc ttaaccagtt gcctgattgg agtatgcttc tgactgcaat cacgaccgtc     300
tcgtggcgg cagagaagca gtggactatg cgtgatcgga atctaagag gcctgacatg     360
ctcgtggact cggttggatc gaagagtatt gttctggatg gctcgtgtc cagacagatt     420
ttttcgatta gatcttatga ataggcgct gatcgaacag cctctataga gacgctgatg     480
aaccacttgc aggaaacatc tatcaatcat tgtaagagtt tgggtcttct caatgacggc     540
tttggtcgta ctcctgggat gtgtaaaaac gacctcattt gggtgcttac aaaaatgcag     600
atcatggtga atcgctaccc aacttggggc gatactgttg agatcaatac ctggttctcc     660
cattcgggga aaatcggtat ggctagcgat tggctaataa ctgattgcaa cacaggagaa     720
attcttataa gagcaacgag cgtgtgggcc atgatgaatc aaaagacgag aagattctca     780
agacttccat acgaggttcg ccaggagtta acgcctcatt atgtggactc tcctcatgtc     840
attgaagata tgatcggaa attgcataag tttgatgtga agactggtga ttccattcgt     900
aagggtctaa ctccgaagtg gaatgacttg gatgtcaatc agcacgtcaa caacgtgaag     960
```

```
tacatcgggt ggattctcga gagtatgcca atagaagttt tggagactca ggagctatgc    1020
tctctcaccg ttgaatatag gcgggaatgc ggaatggaca gtgtgctgga gtccgtgact    1080
gctatggatc cctcagaaga tggaggccta tctcagtaca agcaccttct gcggcttgag    1140
gatgggactg acatcgtgaa gggcagaact gagtggcgac cgaagaatgc aggaactaac    1200
ggggcgatat caacagcaaa gccttcaaat ggaaactcgg tctcttag                 1248
```

<210> SEQ ID NO 28
<211> LENGTH: 1257
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

```
atggtggccg ccgccgcctc ctccgccttc ttccccgtgc ccgccccgg cacctccacc      60 aagccccgca gtccggcaa ctggccctcc cgcctgtccc cctcctccaa gcccaagtcc     120
atccccaacg gcggcttcca ggtgaaggcc aacgcctccg cccacccaa ggccaacggc     180 tccgccgtga acctgaagtc cggctccctg aacacccagg aggacacctc ctcctccccc    240
cccccccgcg ccttcctgaa ccagctgccc gactggtcca tgctgctgac cgccatcacc    300
accgtgttcg tggccgccga aagcagtgg accatgctgg accgcaagtc caagcgcccc    360
gacatgctgg tggactccgt gggcctgaag tccatcgtgc gcgacggcct ggtgtcccgc    420
cagtccttct ccatccgctc ctacgagatc ggcgccgacc gcaccgcctc catcgagacc    480
ctgatgaacc acctgcagga gacctccatc aaccactgca gtccctgggg cctgctgaac    540
gacggcttcg gccgcacccc cggcatgtgc aagaacgacc tgatctgggt gctgaccaag    600
atgcagatca tggtgaaccg ctaccccacc tggggcgaca ccgtggagat caacacctgg    660
ttctcccagt ccggcaagat cggcatgggc tccgactggc tgatctccga ctgcaacacc    720
ggcgagatcc tgatccgcgc cacctccgtg tgggccatga tgaaccagaa gacccgccgc    780
ttctcccgcc tgccctacga ggtgcgccag gagctgaccc ccacttcgt ggactccccc     840 cacgtgatcg aggacaacga ccgcaagctg cacaagttcg acgtgaagac cggcgactcc    900
atccgcaagg gcctgacccc ccgctggaac gacctggacg tgaaccagca cgtgtccaac    960
gtgaagtaca tcggctggat cctggagtcc atgcccatcg aggtgctgga gacccaggag   1020
ctgtgctccc tgaccgtgga gtaccgccgc gagtgcggca tggactccaa gctggagtcc   1080
gtgaccgcca tggaccccrc cgaggaggac ggcgtgcgct cccagtacaa ccacctgctg   1140
cgcctggagg acggcaccga cgtggtgaag ggccgcaccg agtggcgccc caagaacgcc   1200
ggcaccaacg gcgccatctc caccggcaag acctccaacg gcaactccgt gtcctga      1257
```

<210> SEQ ID NO 29
<211> LENGTH: 1248
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

```
atggtgaccg ccgccgcctc ctccgccttc ttccccgtgc ccgccccgg cacctccccc      60 aagcccggca gtcctggcc ctcctccctg tcccctcct tcaagcccaa gtccatcccc     120
```

| | |
|---|---|
| aacgccggct tccaggtgaa ggccaacgcc tccgcccacc ccaaggccaa cggctccgcc | 180 |
| gtgaacctga agtccggctc cctgaacacc caggaggaca cctcctcctc cccccccccc | 240 |
| cgcgccttcc tgaaccagct gcccgactgg tccatgctgc tgaccgccat caccaccgtg | 300 |
| ttcgtggccg ccgagaagca gtggaccatg cgcgaccgca agtccaagcg ccccgacatg | 360 |
| ctggtggact ccgtgggctc caagtccatc gtgctggacg gcctggtgtc ccgccagatc | 420 |
| ttctccatcc gctcctacga gatcggcgcc gaccgcaccg cctccatcga ccctgatg | 480 |
| aaccacctgc aggagacctc catcaaccac tgcaagtccc tgggcctgct gaacgacggc | 540 |
| ttcggccgca cccccggcat gtgcaagaac gacctgatct gggtgctgac caagatgcag | 600 |
| atcatggtga accgctaccc cacctggggc gacaccgtgg agatcaacac ctggttctcc | 660 |
| cactccggca gatcggcat ggcctccgac tggctgatca ccgactgcaa caccggcgag | 720 |
| atcctgatcc gcgccacctc cgtgtgggcc atgatgaacc agaagacccg ccgcttctcc | 780 |
| cgcctgccct acgaggtgcg ccaggagctg accccccact acgtggactc ccccacgtg | 840 |
| atcgaggaca acgaccgcaa gctgcacaag ttcgacgtga gaccggcga ctccatccgc | 900 |
| aagggcctga cccccaagtg gaacgacctg acgtgaacc agcacgtgaa caacgtgaag | 960 |
| tacatcggct ggatcctgga gtccatgccc atcgaggtgc tggagaccca ggagctgtgc | 1020 |
| tccctgaccg tggagtaccg ccgcgagtgc ggcatggact ccgtgctgga gtccgtgacc | 1080 |
| gccatggacc cctccgagga cggcggcctg tcccagtaca agcacctgct cgcctggag | 1140 |
| gacggcaccg acatcgtgaa gggccgcacc gagtggcgcc ccaagaacgc cggcaccaac | 1200 |
| ggcgccatct ccaccgccaa gccctccaac ggcaactccg tgtcctga | 1248 |

<210> SEQ ID NO 30
<211> LENGTH: 1254
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30

| | |
|---|---|
| atggtgggcg ccgccgcctc ctccgccttc ttccccgccc ccgccccgg cacctccccc | 60 |
| aagcccggca gtccggcaa ctggccctcc tccctgtccc cctccctgaa gcccaagtcc | 120 |
| atccccaacg gcggcttcca ggtgaaggcc aacgcctccg cccacccaa ggccaacggc | 180 |
| gccgccgtga acctgaagtc cggctccctg aacacccagg aggacacctc ctcctccccc | 240 |
| ccccccgcg ccttcctgaa ccagctgccc gactggtcca tgctgctgac cgccatcacc | 300 |
| accgtgttcg tggccgccga gaagcagtgg accatgctgg accgcaagtc caagcgcccc | 360 |
| gacatgctgt ggactccgt gggcctgaag aacatcgtgc gcgacggcct ggtgtcccgc | 420 |
| cagtccttct ccatccgctc ctacgagatc ggcgccgacc gcaccgcctc catcgagacc | 480 |
| ctgatgaacc acctgcagga gacctccatc aaccactgca gtccctggg cctgctgaac | 540 |
| gacggcttcg gccgcacccc cggcatgtgc aagaacgacc tgatctgggt gctgaccaag | 600 |
| atgcagatcc tggtgaaccg ctaccccgcc tggggcgaca ccgtggagat caacacctgg | 660 |
| ttctcccagt ccggcaagat cggcatgggc tccgactggc tgatctccga ctgcaacacc | 720 |
| ggcgagatcc tgatccgcgc cacctccgtg tgggccatga tgaaccagaa gacccgccgc | 780 |
| ttctcccgcc tgccctacga ggtgcgccag gagctgaccc ccacttcgt ggactccccc | 840 |
| cacgtgatcg aggacaacga ccgcaagctg cacaagttcg acgtgaagac cggcgactcc | 900 |

```
atccgcaagg gcctgacccc ccgctggaac gacctggacg tgaaccagca cgtgtccaac      960
gtgaagtaca tcggctggat cctggagtcc atgcccatcg aggtgctgga gacccaggag     1020
ctgtgctccc tgaccgtgga gtaccgccgc gagtgcggca tggactccgt gctggagtcc     1080
gtgaccgccc gcgacccctc cgaggacggc ggccgctccc agtacaacca cctgctgcgc     1140
ctggaggacg gcaccgacgt ggtgaagggc cgcaccgagt ggcgctccaa gaacgccggc     1200
accaacggcg ccacctccac cgccaagacc tccaacggca actccgtgtc ctga           1254
```

<210> SEQ ID NO 31
<211> LENGTH: 1254
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 31

```
atggtggccg ccgccgcctc ctccgccttc ttccccgtgc ccgccccggg cacctccctg       60
aagcccggca agtccggcaa ctggccctcc tccctgtccc cctccttcaa gcccaagacc      120
atcccctccg gcggcctgca ggtgaaggcc aacgcctccg cccaccccaa ggccaacggc      180
tccgccgtga acctgaagtc cggctccctg acacccagg aggacacctc ctcctccccc      240
cccccccgcg ccttcctgaa ccagctgccc gactggtcca tgctgctgac cgccatcacc      300
accgtgttcg tggccgccga aagcagtgg accatgctgg accgcaagtc caagcgcccc      360
gagatgctgg tggactccgt gggcctgaag tcctccgtgc gcgacggcct ggtgtcccgc      420
cagtccttct ccatccgctc ctacgagatc ggcgccgacc gcaccgcctc catcgagacc      480
ctgatgaacc acctgcagga gacctccatc aaccactgca gtccctgggg cctgctgaac      540
gacggcttcg gccgcacccc cggcatgtgc aagaacgacc tgatctgggt gctgaccaag      600
atgcagatca tggtgaaccg ctaccccacc tggggcgaca ccgtggaggt gaacacctgg      660
ttctcccagt ccggcaagat cggcatggcc tccgactggc tgatctccga ctgcaacacc      720
ggcgagatcc tgatccgcgc cacctccgtg tgggccatga tgaaccagaa gacccgccgc      780
ttctcccgcc tgccctacga ggtgcgccag gagctgaccc ccactacgt ggactccccc      840 cacgtgatcg aggacaacga ccgcaagctg cacaagttcg acgtgaagac cggcgactcc      900
atccgcaagg gcctgacccc ccgctggaac gacctggacg tgaaccagca cgtgtccaac      960
gtgaagtaca tcggctggat cctggagtcc atgcccatcg aggtgctgga gacccaggag     1020
ctgtgctccc tgaccgtgga gtaccgccgc gagtgcggca tggactccgt gctggagtcc     1080
gtgaccgcca tggacccctc cgaggacggc ggcgtgtccc agtacaagca cctgctgcgc     1140
ctggaggacg gcaccgacat cgtgaagggc cgcaccgagt ggcgcccaa gaacgccggc      1200 accaacggcg ccacctccaa ggccaagacc tccaacggca actccgtgtc ctga           1254
```

<210> SEQ ID NO 32
<211> LENGTH: 1254
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32

```
atggtggccg ccgccgcctc ctccgccttc ttccccgccc ccgccccggg ctcctccccc       60
aagcccggca agtccggcaa ctggccctcc tccctgtccc cctccttcaa gcccaagtcc      120
```

```
atccccaacg gccgcttcca ggtgaaggcc aacgcctccg cccacccaa ggccaacggc      180 tccgccgtga acctgaagtc cggctccctg aacacccagg aggacacctc ctcctccccc      240 ccccccgcg ccttcctgaa ccagctgccc gactggtcca tgctgctgtc cgccatcacc      300
accgtgttcg tggccgccga gaagcagtgg accatgctgg accgcaagtc caagcgcccc      360
gacatgctgg tggactccgt gggcctgaag aacatcgtgc gcgacggcct ggtgtcccgc      420
cagtccttct ccatccgctc ctacgagatc ggcgccgacc gcaccgcctc catcgagacc      480
ctgatgaacc acctgcagga gacctccatc aaccactgca agtccctggg cctgctgaac      540
gacggcttcg gccgcacccc cggcatgtgc aagaacgacc tgatctgggt gctgaccaag      600
atgcagatca tggtgaaccg ctaccccgcc tggggcgaca ccgtggagat caacacctgg      660
ttctcccagt ccggcaagat cggcatgggc tccgactggc tgatctccga ctgcaacacc      720
ggcgagatcc tgatccgcgc cacctccgtg tgggccatga tgaaccagaa gacccgccgc      780
ttctcccgcc tgccctacga ggtgcgccag gagctgaccc ccacttcgt ggactccccc       840 cacgtgatcg aggacaacga ccgcaagctg cacaagttcg acgtgaagac cggcgactcc      900
atccgcaagg gcctgacccc cgctggaac gacctggacg tgaaccagca cgtgtccaac       960
gtgaagtaca tcggctggat cctggagtcc atgcccatcg aggtgctgga gacccaggag     1020
ctgtgctccc tgaccgtgga gtaccgccgc gagtgcggca tggactccgt gctggagtcc     1080
gtgaccgcca tcgacccctc cgaggacggc ggccgctccc agtacaacca cctgctgcgc     1140
ctggacgacg gcaccgacgt ggtgaagggc cgcaccgagt ggcgcccaa gaacgccggc      1200 accaacggcg ccatctccac cggcaagacc tccaacggca actccgtgtc ctga           1254
```

<210> SEQ ID NO 33
<211> LENGTH: 1254
<212> TYPE: DNA
<213> ORGANISM: Artificial Sequence
<220> FEATURE:
<223> OTHER INFORMATION: Description of Artificial Sequence: Synthetic
 polynucleotide

<400> SEQUENCE: 33

```
atggtggccg ccgccgcctc ctccgccttc ttccccgtgc ccgccccgg cacctccctg        60 aagccctgga gtccggcaa ctggccctcc tccctgtccc cctccttcaa gcccaagacc       120
atcccctccg gcggcttcca ggtgaaggcc aacgcctccg cccagcccaa ggccaacggc      180
tccgccgtga acctgaagtc cggctccctg aacacccagg aggacaccac ctcctccccc      240 ccccccgcg ccttcctgaa ccagctgccc gactggtcca tgctgctgac cgccatcacc       300
accgtgttcg tggccgccga gaagcagtgg accatgctgg accgcaagtc caagcgcccc      360
gagaagctgg tggactccgt gggcctgaag tcctccgtgc gcgacggcct ggtgtcccgc      420
cagtccttct ccatccgctc ctacgagatc ggcgccgacc gcaccgcctc catcgagacc      480
ctgatgaacc acctgcagga gacctccatc aaccactgca agtccctggg cctgctgaac      540
gacggcttcg gccgcacccc cggcatgtgc aagaacgacc tgatctgggt gctgaccaag      600
atgcagatca tggtgaaccg ctaccccacc tggggcgaca ccgtggagat caacacctgg      660
ttctcccagt ccggcaagat cggcatggcc tccgactggc tgatctccga ctgcaacacc      720
ggcgagatcc tgatccgcgc cacctccgtg tgggccatga tgaaccagaa gacccgccgc      780
ttctcccgcc tgccctacga ggtgcgccag gagctgaccc ccactacgt ggactccccc       840 cacgtgatcg aggacaacga ccgcaagctg cacaagttcg acgtgaagac cggcgactcc      900
```

```
atccgcaagg gcctgacccc ccgctggaac gacctggacg tgaaccagca cgtgtccaac    960
gtgaagtaca tcggctggat cctggagtcc atgcccatcg aggtgctgga gacccaggag   1020
ctgtgctccc tgaccgtgga gtaccgccgc gagtgcggca tggactccgt gctggagtcc   1080
gtgaccgcca tggaccccct cgaggacgag ggccgctccc agtacaagca cctgctgcgc   1140
ctggaggacg gcaccgacat cgtgaagggc cgcaccgagt ggcgccccaa gaacgccggc   1200
accaacggcg ccatctccac cgccaagaac tccaacggca actccgtgtc ctga         1254
```

<210> SEQ ID NO 34
<211> LENGTH: 1155
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34

```
atggccacca cctccctggc ctccgccttc tgctccatga aggccgtgat gctggcccgc     60
gacggccgcg gcatgaagcc ccgctcctcc gacctgcagc tgcgcgccgg caacgcccag    120 accccctga agatgatcaa cggcaccaag ttctcctaca ccgagtccct gaagcgcctg    180
cccgactggt ccatgctgtt cgccgtgatc accaccatct ctccgtggc cgagaagcag    240 tggaccaacc tggagtggaa gcccaagccc agccccgcc tgcccagct gctggacgac    300 cacttcggcc tgcacggcct ggtgttccgc cgcaccttcg ccatccgctc ctacgaggtg    360
ggccccgacc gctccacctc catcgtggcc gtgatgaacc acctgcagga ggccaccctg    420
aaccacgcca gtccgtgggg catcctgggc gacggcttcg gcaccaccct ggagatgtcc    480
aagcgcgacc tggcctgggt ggtgcgccgc acccacgtgg ccgtggagcg ctaccccgcc    540
tggggcgaca ccgtggaggt ggagtgctgg atcggcgcct ccggcaacaa cggcatgcgc    600
cgcgacttcc tggtgcgcga ctgcaagacc ggcgagatcc tgacccgctg cacctccctg    660
tccgtgatga tgaacacccg cacccgccgc ctgtccaaga tccccgagga ggtgcgcggc    720
gagatcggcc ccctgttcat cgacaacgtg gccgtgaagg acgaggagat caagaagctg    780
cagaagctga acgactcctc cgccgactac atccagggcg gcctgacccc ccgctggaac    840
gacctggacg tgaaccagca cgtgaacaac atcaagtacg tgggctggat cctggagacc    900
gtgcccgact ccatcttcga gtcccaccac atctcctcca tcaccctgga gtaccgccgc    960
gagtgcaccc gcgactccgt gctgcagtcc ctgaccaccg tgtccggcgg ctccctggag   1020
gccggcctgg tgtgcgacca cctgctgcag ctggagggcg gctccgaggt gctgcgcgcc   1080
cgcaccgagt ggcgccccaa gctgaccgac tccttccgcg gcatcatcgt gatccccgcc   1140
gagccctccg tgtga                                                    1155
```

<210> SEQ ID NO 35
<211> LENGTH: 1155
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35

```
atggccacca cctccctggc ctccgccttc tgctccatga aggccgtgat gctggcccgc     60
gacggccgcg gcatgaagcc ccgctcctcc gacctgcagc tgcgcgccgg caacgcccag    120
```

| | |
|---|---|
| accccccctga agatgatcaa cggcaccaag ttctcctaca ccgagtccct gaagcgcctg | 180 |
| cccgactggt ccatgctgtt cgccgtgatc accaccatct tctccgtggc cgagaagcag | 240 |
| tggaccaacc tggagtggaa gcccaagccc aagccccgcc tgccccagct gctggacgac | 300 |
| cacttcggcc tgcacggcct ggtgttccgc cgcaccttcg ccatccgctc ctacgaggtg | 360 |
| ggccccgacc gctccacctc catcgtggcc gtgatgaacc acctgcagga ggccacctg | 420 |
| aaccacgcca gtccgtgggg catcctgggc gacggcttcg caccaccct ggagatgtcc | 480 |
| aagcgcgacc tggcctgggt ggtgcgccgc acccacgtgg ccgtggagcg ctaccccgcc | 540 |
| tggggcgaca ccgtggaggt ggaggcctgg gtgggcgcct ccggcaacat cggcatgcgc | 600 |
| cgcgacttcc tggtgcgcga ctgcaagacc ggccacatcc tggcccgctg cacctccgtg | 660 |
| tccgtgatga tgaacgcccg cacccgccgc ctgtccaaga tcccccagga ggtgcgcgcc | 720 |
| gagatcgacc ccctgttcat cgagaaggtg gccgtgaagg agggcgagat caagaagctg | 780 |
| cagaagttca acgactccac cgccgactac atccagggcg gctggacccc cgctggaac | 840 |
| gacctggacg tgaaccagca cgtgaacaac atcaagtaca tcggctggat cttcaagtcc | 900 |
| gtgcccgact ccatctccga gaaccactac ctgtcctcca tcaccctgga gtaccgccgc | 960 |
| gagtgcaccc gcggctccgc cctgcagtcc ctgaccaccg tgtgcggcga ctcctccgag | 1020 |
| gccggcatca tctgcgagca cctgctgcag ctggaggacg ccccgaggt gctgcgcgcc | 1080 |
| cgcaccgagt ggcgccccaa gctgaccgac tccttccgcg gcatcatcgt gatccccgcc | 1140 |
| gagccctccg tgtga | 1155 |

<210> SEQ ID NO 36
<211> LENGTH: 1248
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36

| | |
|---|---|
| atggtgaccg ccgccgcctc ctccgccttc ttccccgtgc ccgccccgg cacctcccc | 60 |
| aagcccggca gtcctggcc ctcctccctg tccccctcct tcaagcccaa gtccatcccc | 120 |
| aacgccggct tccaggtgaa ggccaacgcc tccgcccacc ccaaggccaa cggctccgcc | 180 |
| gtgaacctga gtccggctc cctgaacacc caggaggaca cctcctcctc cccccccccc | 240 |
| cgcgccttcc tgaaccagct gcccgactgg tccatgctgc tgaccgccat caccaccgtg | 300 |
| ttcgtggccg ccgagaagca gtggaccatg cgcgaccgca gtccaagcg ccccgacatg | 360 |
| ctggtggact ccgtgggctc caagtccatc gtgctggacg gcctggtgtc ccgccagatc | 420 |
| ttctccatcc gctcctacga gatcggcgcc gaccgcaccg cctccatcga ccctgatg | 480 |
| aaccacctgc aggagaccctc catcaaccac tgcaagtccc tgggcctgct gaacgacggc | 540 |
| ttcggccgca ccccggcat gtgcaagaac gacctgatct gggtgctgac caagatgcag | 600 |
| atcatggtga accgctaccc cacctggggc gacaccgtgg agatcaacac ctggttctcc | 660 |
| cactccggca gatcggcat ggcctccgac tggctgatca ccgactgcaa caccggcgag | 720 |
| atcctgatcc gcgccacctc cgtgtgggcc atgatgaacc agaagacccg ccgcttctcc | 780 |
| cgcctgccct acgaggtgcg ccaggagctg accccccact acgtggactc ccccacgtg | 840 |
| atcgaggaca acgaccgcaa gctgcacaag ttcgacgtga agaccggcga ctccatccgc | 900 |
| aagggcctga cccccaagtg gaacgacctg acgtgaacc agcacgtgaa caacgtgaag | 960 |

```
tacatcggct ggatcctgga gtccatgccc atcgaggtgc tggagaccca ggagctgtgc    1020
tccctgaccg tggagtaccg ccgcgagtgc ggcatggact ccgtgctgga gtccgtgacc    1080
gccatggacc cctccgagga cggcggcctg tcccagtaca agcacctgct gcgcctggag    1140
gacggcaccg acatcgtgaa gggccgcacc gagtggcgcc caagaacgc cggcaccaac    1200 ggcgccatct ccaccgccaa gccctccaac ggcaactccg tgtcctga                1248

<210> SEQ ID NO 37
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Ala Ala Ile
        35

<210> SEQ ID NO 38
<211> LENGTH: 6398
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
gaagagcgcc caatgtttaa acccctcaac tgcgacgctg ggaaccttct ccgggcaggc    60
gatgtgcgtg ggtttgcctc cttggcacgg ctctacaccg tcgagtacgc catgaggcgg    120
tgatggctgt gtcggttgcc acttcgtcca gagacggcaa gtcgtccatc ctctgcgtgt    180
gtggcgcgac gctgcagcag tccctctgca gcagatgagc gtgactttgg ccatttcacg    240
cactcgagtg tacacaatcc attttctta aagcaaatga ctgctgattg accagatact     300
gtaacgctga tttcgctcca gatcgcacag atagcgacca tgttgctgcg tctgaaaatc    360
tggattccga attcgaccct ggcgctccat ccatgcaaca gatggcgaca cttgttacaa    420
ttcctgtcac ccatcggcat ggagcaggtc cacttagatt cccgatcacc cacgcacatc    480
tcgctaatag tcattcgttc gtgtcttcga tcaatctcaa gtgagtgtgc atggatcttg    540
gttgacgatg cggtatgggt ttgcgccgct ggctgcaggg tctgcccaag caagctaac    600 ccagctcctc tccccgacaa tactctcgca ggcaaagccg tcacttgcc ttccagattg     660 ccaataaact caattatggc ctctgtcatg ccatccatgg gtctgatgaa tggtcacgct    720
cgtgtcctga ccgttcccca gcctctgcg tccctgccc cgccaccag cccacgccgc       780 gcggcagtcg ctgccaaggc tgtctcggag gtaccctttc ttgcgctatg acacttccag    840
caaaaggtag ggcgggctgc gagacggctt cccggcgctg catgcaacac cgatgatgct    900
tcgacccccc gaagctcctt cggggctgca tgggcgctcc gatgccgctc cagggcgagc    960 gctgttaaa tagccaggcc cccgattgca aagacattat agcgagctac caaagccata   1020
ttcaaacacc tagatcacta ccacttctac acaggccact cgagcttgtg atcgcactcc   1080
gctaaggggg cgcctcttcc tcttcgtttc agtcacaacc cgcaaactct agaatatcaa   1140
```

```
tgctgctgca ggccttcctg ttcctgctgg ccggcttcgc cgccaagatc agcgcctcca    1200
tgacgaacga gacgtccgac cgcccccctgg tgcacttcac ccccaacaag ggctggatga   1260
acgaccccaa cggcctgtgg tacgacgaga aggacgccaa gtggcacctg tacttccagt    1320
acaacccgaa cgacaccgtc tggggacgc ccttgttctg gggccacgcc acgtccgacg     1380
acctgaccaa ctgggaggac cagcccatcg ccatcgcccc gaagcgcaac gactccggcg    1440
ccttctccgg ctccatggtg gtggactaca caacacctc cggcttcttc aacgacacca     1500
tcgacccgcg ccagcgctgc gtggccatct ggacctacaa caccccggag tccgaggagc    1560
agtacatctc ctacagcctg gacggcggct acaccttcac cgagtaccag aagaaccccg    1620
tgctggccgc caactccacc cagttccgcg acccgaaggt cttctggtac gagccctccc    1680
agaagtggat catgaccgcg ccaagtccc aggactacaa gatcgagatc tactcctccg     1740
acgacctgaa gtcctggaag ctggagtccg cgttcgccaa cgagggcttc ctcggctacc    1800
agtacgagtg ccccggcctg atcgaggtcc ccaccgagca ggaccccagc aagtcctact    1860
gggtgatgtt catctccatc aaccccggcg ccccggccgg cggctccttc aaccagtact    1920
tcgtcggcag cttcaacggc acccacttcg aggccttcga caaccagtcc cgcgtggtgg    1980
acttcggcaa ggactactac gccctgcaga ccttcttcaa caccgacccg acctacggga    2040
gcgccctggg catcgcgtgg gcctccaact gggagtactc cgccttcgtg cccaccaacc    2100
cctggcgctc ctccatgtcc ctcgtgcgca agttctccct caacaccgag taccaggcca    2160
acccggagac ggagctgatc aacctgaagg ccgagccgat cctgaacatc agcaacgccg    2220 gccccctggag ccggttcgcc accaacacca cgttgacgaa ggccaacagc tacaacgtcg   2280
acctgtccaa cagcaccggc accctggagt tcagctggt gtacgccgtc aacaccaccc    2340
agacgatctc caagtccgtg ttcgcggacc tctccctctg gttcaagggc ctggaggacc    2400
ccgaggagta cctccgcatg ggcttcgagg tgtccgcgtc ctccttcttc ctggaccgcg    2460
ggaacagcaa ggtgaagttc gtgaaggaga ccccctactt caccaaccgc atgagcgtga    2520
acaaccagcc cttcaagagc gagaacgacc tgtcctacta caaggtgtac ggcttgctgg    2580 accagaaacat cctggagctg tacttcaacg acggcgacgc cgtgtccacc aacacctact   2640
tcatgaccac cgggaacgcc ctgggctccg tgaacatgac gacgggggtg gacaacctgt    2700
tctacatcga caagttccag gtgcgcgagg tcaagtgaca attgacgccc gcgcggcgca    2760
cctgacctgt tctctcgagg gcgcctgttc tgccttgcga acaagccccc tggagcatgc    2820
gtgcatgatc gtctctggcg ccccgccgcg cggtttgtcg ccctcgcggg cgccgcggcc    2880 gcggggcgc attgaaattg ttgcaaaccc cacctgacag attgagggcc caggcaggaa    2940
ggcgttgaga tggaggtaca ggagtcaagt aactgaaagt tttatgata actaacaaca   3000 aagggtcgtt tctggccagc gaatgacaag aacaagattc cacatttccg tgtagaggct    3060
tgccatcgaa tgtgagcggg cgggccgcg acccgacaaa accccttacga cgtggtaaga    3120 aaaacgtggc gggcactgtc cctgtagcct gaagaccagc aggagacgat cggaagcatc    3180
acagcacagg atcccgcgtc tcgaacagag cgcgcagagg aacgctgaag gtctcgcctc    3240
tgtcgcacct cagcgcggca taccacaa taaccacctg acgaatgcgc ttggttcttc      3300
gtccattagc gaagcgtccg gttcacacac gtgccacgtt ggcgaggtgg caggtgacaa    3360
tgatcggtgg agctgatggt cgaaacgttc acagcctagg gatatcgtga aaactcgctc    3420
gaccgcccgc gtcccgcagg cagcgatgac gtgtgcgtga cctgggtgtt tcgtcgaaag    3480
gccagcaacc ccaaatcgca ggcgatccgg agattgggat ctgatccgag cttggaccag    3540
```

-continued

```
atcccccacg atgcggcacg ggaactgcat cgactcggcg cggaacccag ctttcgtaaa   3600
tgccagattg gtgtccgata ccttgatttg ccatcagcga aacaagactt cagcagcgag   3660
cgtatttggc gggcgtgcta ccagggttgc atacattgcc catttctgtc tggaccgctt   3720
taccggcgca gagggtgagt tgatgggggtt ggcaggcatc gaaacgcgcg tgcatggtgt   3780
gtgtgtctgt tttcggctgc acaatttcaa tagtcggatg ggcgacggta gaattgggtg   3840
ttgcgctcgc gtgcatgcct cgccccgtcg ggtgtcatga ccgggactgg aatccccct   3900 cgcgaccctc ctgctaacgc tcccgactct cccgcccgcg cgcaggatag actctagttc   3960
aaccaatcga caactagtat ggccaccgcc tccaccttct ccgccttcaa cgcccgctgc   4020
ggcgacctgc gccgctccgc cggctccggc ccccgccgcc ccgcccgccc cctgcccgtg   4080
cgcgccgcca tcaacgcctc cgcccacccc aaggccaacg gctccgccgt gaacctgaag   4140
tccggctccc tgaacaccca ggaggacacc tcctcctccc ccccccccg cgccttcctg   4200 aaccagctgc ccgactggtc catgctgctg accgccatca ccaccgtgtt cgtggccgcc   4260
gagaagcagt ggaccatgct ggaccgcaag tccaagcgcc ccgacatgct ggtggactcc   4320
gtgggcctga agtccatcgt gcgcgacggc ctggtgtccc gccagtcctt ctccatccgc   4380
tcctacgaga tcggcgccga ccgcaccgcc tccatcgaga ccctgatgaa ccacctgcag   4440
gagacctcca tcaaccactg caagtccctg ggcctgctga cgacggcctt cggccgcacc   4500
cccggcatgt gcaagaacga cctgatctgg gtgctgacca agatgcagat catggtgaac   4560
cgctacccca cctggggcga caccgtggag atcaacacct ggttctccca gtccggcaag   4620
atcggcatgg gctccgactg gctgatctcc gactgcaaca ccggcgagat cctgatccgc   4680
gccacctccg tgtgggccat gatgaaccag aagacccgcc gcttctcccg cctgccctac   4740
gaggtgcgcc aggagctgac cccccacttc gtggactccc ccacgtgat cgaggacaac   4800 gaccgcaagc tgcacaagtt cgacgtgaag accggcgact ccatccgcaa gggcctgacc   4860
ccccgctgga acgacctgga cgtgaaccag cacgtgtcca cgtgaagta catcggctgg   4920 atcctggagt ccatgcccat cgaggtgctg gagacccagg agctgtgctc cctgaccgtg   4980
gagtaccgcc gcgagtgcgg catggactcc aagctggagt ccgtgaccgc catggacccc   5040
tccgaggagg acggcgtgcg ctcccagtac aaccacctgc tgcgcctgga ggacggcacc   5100
gacgtggtga agggccgcac cgagtggcgc cccaagaacg ccggcaccaa cggcgccatc   5160
tccaccggca agacctccaa cggcaactcc gtgtccatgg actacaagga ccacgacggc   5220
gactacaagg accacgacat cgactacaag gacgacgacg acaagtgact cgaggcagca   5280
gcagctcaga tagtatcgac acactctgga cgctggtcgt gtgatggact gttgccgcca   5340
cacttgctgc cttgacctgt gaatatccct gccgctttta tcaaacagcc tcagtgtgtt   5400
tgatcttgtg tgtacgcgct tttgcgagtt gctagctgct tgtgctattt gcgaatacca   5460
cccccagcat ccccttccct cgtttcatat cgcttgcatc ccaaccgcaa cttatctacg   5520
ctgtcctgct atccctcagc gctgctcctg ctcctgctca ctgcccctcg cacagccttg   5580
gtttgggctc cgcctgtatt ctcctggtac tgcaacctgt aaaccagcac tgcaatgctg   5640
atgcacggga agtagtggga tgggaacaca aatggaaagc ttgagctcca gcgccatgcc   5700 acgcccttg atggcttcaa gtacgattac ggtgttggat tgtgtgtttg ttgcgtagtg   5760
tgcatggttt agaataatac acttgatttc ttgctcacgg caatctcggc ttgtccgcag   5820
gttcaacccc atttcggagt ctcaggtcag ccgcgcaatg accagccgct acttcaagga   5880
```

```
cttgcacgac aacgccgagg tgagctatgt ttaggacttg attggaaatt gtcgtcgacg    5940
catattcgcg ctccgcgaca gcacccaagc aaaatgtcaa gtgcgttccg atttgcgtcc    6000
gcaggtcgat gttgtgatcg tcggcgccgg atccgccggt ctgtcctgcg cttacgagct    6060
gaccaagcac cctgacgtcc gggtacgcga gctgagattc gattagacat aaattgaaga    6120
ttaaacccgt agaaaaattt gatggtcgcg aaactgtgct cgattgcaag aaattgatcg    6180
tcctccactc cgcaggtcgc catcatcgag cagggcgttg ctcccggcgg cggcgcctgg    6240 ctgggggac agctgttctc ggccatgtgt gtacgtagaa ggatgaattt cagctggttt     6300
tcgttgcaca gctgtttgtg catgatttgt ttcagactat tgttgaatgt ttttagattt    6360
cttaggatgc atgatttgtc tgcatgcgac tgaagagc                            6398
```

<210> SEQ ID NO 39
<211> LENGTH: 32
<212> TYPE: PRT
<213> ORGANISM: Sassafras albidum

<400> SEQUENCE: 39

Leu Phe Ala Val Ile Thr Thr Ile Phe Ser Val Ala Glu Lys Gln Trp
1               5                   10                  15

Thr Asn Leu Glu Trp Lys Pro Lys Pro Lys Pro Arg Leu Pro Gln Leu
            20                  25                  30

<210> SEQ ID NO 40
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Ala Thr Thr Ser Leu Ala Ser Ala Phe Cys Ser Met Lys Ala Val
1               5                   10                  15

Met Leu Ala Arg Asp Gly Arg Gly Met Lys Pro Arg Ser Ser Asp Leu
            20                  25                  30

Gln Leu Arg Ala Gly Asn Ala Gln Thr Pro Leu Lys Met Ile Asn Gly
        35                  40                  45

Thr Lys Phe Ser Tyr Thr Glu Ser Leu Lys Arg Leu Pro Asp Trp Ser
    50                  55                  60

Met Leu Asp Asp His Phe Gly Leu His Gly Leu Val Phe Arg Arg Thr
65                  70                  75                  80

Phe Ala Ile Arg Ser Tyr Glu Val Gly Pro Asp Arg Ser Thr Ser Ile
                85                  90                  95

Val Ala Val Met Asn His Leu Gln Glu Ala Thr Leu Asn His Ala Lys
            100                 105                 110

Ser Val Gly Ile Leu Gly Asp Gly Phe Gly Thr Thr Leu Glu Met Ser
        115                 120                 125

Lys Arg Asp Leu Ala Trp Val Val Arg Arg Thr His Val Ala Val Glu
    130                 135                 140

Arg Tyr Pro Ala Trp Gly Asp Thr Val Glu Val Glu Cys Trp Ile Gly
145                 150                 155                 160

Ala Ser Gly Asn Asn Gly Met Arg Arg Asp Phe Leu Val Arg Asp Cys
                165                 170                 175

Lys Thr Gly Glu Ile Leu Thr Arg Cys Thr Ser Leu Ser Val Met Met
            180                 185                 190

```
Asn Thr Arg Thr Arg Arg Leu Ser Lys Ile Pro Glu Glu Val Arg Gly
            195                 200                 205

Glu Ile Gly Pro Leu Phe Ile Asp Asn Val Ala Val Lys Asp Glu Glu
    210                 215                 220

Ile Lys Lys Leu Gln Lys Leu Asn Asp Ser Ser Ala Asp Tyr Ile Gln
225                 230                 235                 240

Gly Gly Leu Thr Pro Arg Trp Asn Asp Leu Asp Val Asn Gln His Val
                245                 250                 255

Asn Asn Ile Lys Tyr Val Gly Trp Ile Leu Thr Val Pro Asp Ser
            260                 265                 270

Ile Phe Glu Ser His His Ile Ser Ser Ile Thr Leu Glu Tyr Arg Arg
    275                 280                 285

Glu Cys Thr Arg Asp Ser Val Leu Gln Ser Leu Thr Thr Val Ser Gly
290                 295                 300

Gly Ser Leu Glu Ala Gly Leu Val Cys Asp His Leu Leu Gln Leu Glu
305                 310                 315                 320

Gly Gly Ser Glu Val Leu Arg Ala Arg Thr Glu Trp Arg Pro Lys Leu
                325                 330                 335

Thr Asp Ser Phe Arg Gly Ile Ile Val Ile Pro Ala Glu Pro Ser Val
            340                 345                 350

<210> SEQ ID NO 41
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Val Ala Thr Ser Leu Ala Ser Ala Phe Cys Ser Met Lys Ala Val
1               5                   10                  15

Met Leu Ala Asp Asp Gly Arg Gly Met Lys Pro Arg Ser Ser Asp Leu
            20                  25                  30

Gln Leu Arg Ala Gly Asn Ala Gln Thr Ser Leu Lys Met Ile Asp Gly
        35                  40                  45

Thr Lys Phe Ser Tyr Thr Glu Ser Leu Lys Arg Leu Pro Asp Trp Ser
50                  55                  60

Lys Leu Asp Asp Arg Phe Gly Leu His Gly Leu Val Phe Arg Arg Thr
65                  70                  75                  80

Phe Ala Ile Arg Ser Tyr Glu Val Gly Pro Asp Arg Ser Ala Ser Ile
                85                  90                  95

Leu Ala Val Leu Asn His Leu Gln Glu Ala Thr Leu Asn His Ala Glu
            100                 105                 110

Ser Val Gly Ile Leu Gly Asp Arg Phe Gly Thr Leu Glu Met Ser
        115                 120                 125

Lys Arg Asp Leu Met Trp Val Val Arg Arg Thr Tyr Val Ala Val Glu
130                 135                 140

Arg Tyr Pro Ala Trp Gly Asp Thr Val Glu Ile Glu Ser Trp Ile Gly
145                 150                 155                 160

Ala Ser Gly Asn Asn Gly Met Arg Arg Glu Phe Leu Val Arg Asp Phe
                165                 170                 175

Lys Thr Gly Glu Ile Leu Thr Arg Cys Thr Ser Leu Ser Val Met Met
            180                 185                 190

Asn Thr Arg Thr Arg Arg Leu Ser Lys Ile Pro Glu Glu Val Arg Gly
        195                 200                 205
```

```
Glu Ile Gly Pro Val Phe Ile Asp Asn Val Ala Val Lys Asp Glu Glu
            210                 215                 220

Ile Lys Lys Leu Gln Lys Leu Asn Asp Ser Thr Ala Asp Tyr Ile Gln
225                 230                 235                 240

Gly Gly Leu Ile Pro Arg Trp Asn Asp Leu Asp Leu Asn Gln His Val
                    245                 250                 255

Asn Asn Ile Lys Tyr Val Ser Trp Ile Leu Glu Thr Val Pro Asp Ser
                260                 265                 270

Ile Leu Glu Ser Tyr His Met Ser Ser Ile Thr Leu Glu Tyr Arg Arg
            275                 280                 285

Glu Cys Thr Arg Asp Ser Val Leu Gln Ser Leu Thr Thr Val Ser Gly
        290                 295                 300

Gly Ser Ser Glu Ala Gly Leu Val Cys Glu His Ser Leu Leu Leu Glu
305                 310                 315                 320

Gly Gly Ser Glu Val Leu Arg Ala Arg Thr Glu Trp Arg Pro Lys Leu
                325                 330                 335

Thr Asp Ser Phe Arg Gly Ile Ser Val Ile Pro Ala Glu Gln Ser Val
                340                 345                 350

<210> SEQ ID NO 42
<211> LENGTH: 316
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gly Asn Ala Gln Thr Pro Leu Lys Met Ile Asn Gly Thr Lys Phe Ser
1               5                   10                  15

Tyr Thr Glu Ser Leu Lys Arg Leu Pro Asp Trp Ser Met Leu Asp Asp
                20                  25                  30

His Phe Gly Leu His Gly Leu Val Phe Arg Arg Thr Phe Ala Ile Arg
            35                  40                  45

Ser Tyr Glu Val Gly Pro Asp Arg Ser Thr Ser Ile Val Ala Val Met
50                  55                  60

Asn His Leu Gln Glu Ala Thr Leu Asn His Ala Lys Ser Val Gly Ile
65                  70                  75                  80

Leu Gly Asp Gly Phe Gly Thr Thr Leu Glu Met Ser Lys Arg Asp Leu
                85                  90                  95

Ala Trp Val Val Arg Arg Thr His Val Ala Val Glu Arg Tyr Pro Ala
            100                 105                 110

Trp Gly Asp Thr Val Glu Val Glu Cys Trp Ile Gly Ala Ser Gly Asn
        115                 120                 125

Asn Gly Met Arg Arg Asp Phe Leu Val Arg Asp Cys Lys Thr Gly Glu
130                 135                 140

Ile Leu Thr Arg Cys Thr Ser Leu Ser Val Met Met Asn Thr Arg Thr
145                 150                 155                 160

Arg Arg Leu Ser Lys Ile Pro Glu Glu Val Arg Gly Glu Ile Gly Pro
                165                 170                 175

Leu Phe Ile Asp Asn Val Ala Val Lys Asp Glu Glu Ile Lys Lys Leu
            180                 185                 190

Gln Lys Leu Asn Asp Ser Ser Ala Asp Tyr Ile Gln Gly Gly Leu Thr
        195                 200                 205

Pro Arg Trp Asn Asp Leu Asp Val Asn Gln His Val Asn Asn Ile Lys
```

```
            210                 215                 220

Tyr Val Gly Trp Ile Leu Glu Thr Val Pro Asp Ser Ile Phe Glu Ser
225                 230                 235                 240

His His Ile Ser Ser Ile Thr Leu Glu Tyr Arg Arg Glu Cys Thr Arg
                245                 250                 255

Asp Ser Val Leu Gln Ser Leu Thr Thr Val Ser Gly Gly Ser Leu Glu
                260                 265                 270

Ala Gly Leu Val Cys Asp His Leu Leu Gln Leu Glu Gly Gly Ser Glu
            275                 280                 285

Val Leu Arg Ala Arg Thr Glu Trp Arg Pro Lys Leu Thr Asp Ser Phe
        290                 295                 300

Arg Gly Ile Ile Val Ile Pro Ala Glu Pro Ser Val
305                 310                 315

<210> SEQ ID NO 43
<211> LENGTH: 316
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gly Asn Ala Gln Thr Ser Leu Lys Met Ile Asp Gly Thr Lys Phe Ser
1               5                   10                  15

Tyr Thr Glu Ser Leu Lys Arg Leu Pro Asp Trp Ser Lys Leu Asp Asp
            20                  25                  30

Arg Phe Gly Leu His Gly Leu Val Phe Arg Arg Thr Phe Ala Ile Arg
        35                  40                  45

Ser Tyr Glu Val Gly Pro Asp Arg Ser Ala Ser Ile Leu Ala Val Leu
    50                  55                  60

Asn His Leu Gln Glu Ala Thr Leu Asn His Ala Glu Ser Val Gly Ile
65                  70                  75                  80

Leu Gly Asp Arg Phe Gly Glu Thr Leu Glu Met Ser Lys Arg Asp Leu
                85                  90                  95

Met Trp Val Val Arg Arg Thr Tyr Val Ala Val Glu Arg Tyr Pro Ala
            100                 105                 110

Trp Gly Asp Thr Val Glu Ile Glu Ser Trp Ile Gly Ala Ser Gly Asn
        115                 120                 125

Asn Gly Met Arg Arg Glu Phe Leu Val Arg Asp Phe Lys Thr Gly Glu
    130                 135                 140

Ile Leu Thr Arg Cys Thr Ser Leu Ser Val Met Met Asn Thr Arg Thr
145                 150                 155                 160

Arg Arg Leu Ser Lys Ile Pro Glu Glu Val Arg Gly Glu Ile Gly Pro
                165                 170                 175

Val Phe Ile Asp Asn Val Ala Val Lys Asp Glu Glu Ile Lys Lys Leu
            180                 185                 190

Gln Lys Leu Asn Asp Ser Thr Ala Asp Tyr Ile Gln Gly Gly Leu Ile
        195                 200                 205

Pro Arg Trp Asn Asp Leu Asp Leu Asn Gln His Val Asn Asn Ile Lys
    210                 215                 220

Tyr Val Ser Trp Ile Leu Glu Thr Val Pro Asp Ser Ile Leu Glu Ser
225                 230                 235                 240

Tyr His Met Ser Ser Ile Thr Leu Glu Tyr Arg Arg Glu Cys Thr Arg
                245                 250                 255
```

Asp Ser Val Leu Gln Ser Leu Thr Thr Val Ser Gly Gly Ser Ser Glu
            260                 265                 270

Ala Gly Leu Val Cys Glu His Ser Leu Leu Glu Gly Gly Ser Glu
        275                 280                 285

Val Leu Arg Ala Arg Thr Glu Trp Arg Pro Lys Leu Thr Asp Ser Phe
    290                 295                 300

Arg Gly Ile Ser Val Ile Pro Ala Glu Gln Ser Val
305                 310                 315

<210> SEQ ID NO 44
<211> LENGTH: 1134
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44

```
atggccaccg cctccacctt ctccgccttc aacgcccgct gcggcgacct gcgccgctcc      60
gccggctccg gccccgccg ccccgcccgc ccctgcccg tgcgcgccgc catcggcaac     120
gcccagaccc ccctgaagat gatcaacggc accaagttct cctacaccga gtccctgaag     180
cgcctgcccg actggtccat gctggacgac cacttcggcc tgcacggcct ggtgttccgc     240
cgcaccttcg ccatccgctc ctacgaggtg gcccccgacc gctccacctc catcgtggcc     300
gtgatgaacc acctgcagga ggccaccctg aaccacgcca gtccgtggg catcctgggc     360
gacggcttcg gcaccaccct ggagatgtcc aagcgcgacc tggcctgggt ggtgcgccgc     420
acccacgtgg ccgtggagcg ctaccccgcc tggggcgaca ccgtggaggt ggagtgctgg     480
atcggcgcct ccggcaacaa cggcatgcgc gcgacttcc tggtgcgcga ctgcaagacc     540
ggcgagatcc tgacccgctg cacctccctg tccgtgatga tgaacacccg cacccgccgc     600
ctgtccaaga tccccgagga ggtgcgcggc gagatcggcc ccctgttcat cgacaacgtg     660
gccgtgaagg acgaggagat caagaagctg cagaagctga cgactcctc cgccgactac     720
atccagggcg gcctgacccc cgctggaac gacctggacg tgaaccagca cgtgaacaac     780
atcaagtacg tgggctggat cctggagacc gtgcccgact ccatcttcga gtcccaccac     840
atctcctcca tcaccctgga gtaccgccgc gagtgcaccc gcgactccgt gctgcagtcc     900
ctgaccaccg tgtccggcgg ctccctggag gccggcctgg tgtgcgacca cctgctgcag     960
ctggagggcg gctccgaggt gctgcgcgcc cgcaccgagt ggcgccccaa gctgaccgac    1020
tccttccgcg gcatcatcgt gatccccgcc gagccctccg tgatggacta caaggaccac    1080
gacggcgact acaaggacca cgacatcgac tacaaggacg acgacgacaa gtga          1134
```

<210> SEQ ID NO 45
<211> LENGTH: 1134
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45

```
atggccaccg cctccacctt ctccgccttc aacgcccgct gcggcgacct gcgccgctcc      60
gccggctccg gccccgccg ccccgcccgc ccctgcccg tgcgcgccgc catcggcaac     120
gcccagacct ccctgaagat gatcgacggc accaagttct cctacaccga gtccctgaag     180
cgcctgcccg actggtccaa gctggacgac cgcttcggcc tgcacggcct ggtgttccgc     240
```

```
cgcaccttcg ccatccgctc ctacgaggtg ggccccgacc gctccgcctc catcctggcc    300
gtgctgaacc acctgcagga ggccaccctg aaccacgccg agtccgtggg catcctgggc    360
gaccgcttcg gcgagaccct ggagatgtcc aagcgcgacc tgatgtgggt ggtgcgccgc    420
acctacgtgg ccgtggagcg ctaccccgcc tggggcgaca ccgtggagat cgagtcctgg    480
atcggcgcct ccggcaacaa cggcatgcgc cgcgagttcc tggtgcgcga cttcaagacc    540
ggcgagatcc tgacccgctg cacctccctg tccgtgatga tgaacacccg cacccgccgc    600
ctgtccaaga tccccgagga ggtgcgcggc gagatcggcc ccgtgttcat cgacaacgtg    660
gccgtgaagg acgaggagat caagaagctg cagaagctga cgactccac cgccgactac    720
atccagggcg gcctgatccc ccgctggaac gacctggacc tgaaccagca cgtgaacaac    780
atcaagtacg tgtcctggat cctggagacc gtgcccgact ccatcctgga gtcctaccac    840
atgtcctcca tcaccctgga gtaccgccgc gagtgcaccc gcgactccgt gctgcagtcc    900
ctgaccaccg tgtccggcgg ctcctccgag gccggcctgg tgtgcgagca ctccctgctg    960
ctggagggcg gctccgaggt gctgcgcgcc cgcaccgagt ggcgccccaa gctgaccgac   1020
tccttccgcg gcatctccgt gatccccgcc gagcagtccg tgatggacta caaggaccac   1080
gacggcgact acaaggacca cgacatcgac tacaaggacg acgacgacaa gtga         1134
```

<210> SEQ ID NO 46
<211> LENGTH: 357
<212> TYPE: PRT
<213> ORGANISM: Cinnamomum camphora

<400> SEQUENCE: 46

```
Met Val Thr Thr Ser Leu Ala Ser Ala Tyr Phe Ser Met Lys Ala Val
1               5                   10                  15

Met Leu Ala Pro Asp Gly Arg Gly Ile Lys Pro Arg Ser Ser Gly Leu
            20                  25                  30

Gln Val Arg Ala Gly Asn Glu Arg Asn Ser Cys Lys Val Ile Asn Gly
        35                  40                  45

Thr Lys Val Lys Asp Thr Glu Gly Leu Lys Gly Cys Ser Thr Leu Gln
    50                  55                  60

Gly Gln Ser Met Leu Asp Asp His Phe Gly Leu His Gly Leu Val Phe
65                  70                  75                  80

Arg Arg Thr Phe Ala Ile Arg Cys Tyr Glu Val Gly Pro Asp Arg Ser
                85                  90                  95

Thr Ser Ile Met Ala Val Met Asn His Leu Gln Glu Ala Ala Arg Asn
            100                 105                 110

His Ala Glu Ser Leu Gly Leu Leu Gly Asp Gly Phe Gly Glu Thr Leu
        115                 120                 125

Glu Met Ser Lys Arg Asp Leu Ile Trp Val Val Arg Arg Thr His Val
    130                 135                 140

Ala Val Glu Arg Tyr Pro Ala Trp Gly Asp Thr Val Glu Val Glu Ala
145                 150                 155                 160

Trp Val Gly Ala Ser Gly Asn Thr Gly Met Arg Arg Asp Phe Leu Val
                165                 170                 175

Arg Asp Cys Lys Thr Gly His Ile Leu Thr Arg Cys Thr Ser Val Ser
            180                 185                 190

Val Met Met Asn Met Arg Thr Arg Arg Leu Ser Lys Ile Pro Gln Glu
        195                 200                 205

Val Arg Ala Glu Ile Asp Pro Leu Phe Ile Glu Lys Val Ala Val Lys
```

```
                 210                 215                 220

Glu Gly Glu Ile Lys Lys Leu Gln Lys Leu Asn Asp Ser Thr Ala Asp
225                 230                 235                 240

Tyr Ile Gln Gly Gly Trp Thr Pro Arg Trp Asn Asp Leu Asp Val Asn
                245                 250                 255

Gln His Val Asn Asn Ile Ile Tyr Val Gly Trp Ile Phe Lys Ser Val
            260                 265                 270

Pro Asp Ser Ile Ser Glu Asn His His Leu Ser Ser Ile Thr Leu Glu
        275                 280                 285

Tyr Arg Arg Glu Cys Thr Arg Gly Asn Lys Leu Gln Ser Leu Thr Thr
    290                 295                 300

Val Cys Gly Gly Ser Ser Glu Ala Gly Ile Ile Cys Glu His Leu Leu
305                 310                 315                 320

Gln Leu Glu Asp Gly Ser Glu Val Leu Arg Ala Arg Thr Glu Trp Arg
                325                 330                 335

Pro Lys His Thr Asp Ser Phe Gln Gly Ile Ser Glu Arg Phe Pro Gln
            340                 345                 350

Gln Glu Pro His Lys
        355

<210> SEQ ID NO 47
<211> LENGTH: 32
<212> TYPE: PRT
<213> ORGANISM: Sassafras albidum

<400> SEQUENCE: 47

Leu Phe Ala Val Ile Thr Thr Ile Phe Ser Val Ala Glu Lys Gln Trp
1               5                   10                  15

Thr Asn Leu Glu Trp Lys Pro Lys Pro Lys Pro Arg Leu Pro Gln Leu
            20                  25                  30

<210> SEQ ID NO 48
<211> LENGTH: 28
<212> TYPE: PRT
<213> ORGANISM: Lindera benzoin

<400> SEQUENCE: 48

Leu Leu Thr Val Ile Thr Thr Ile Phe Ser Ala Ala Glu Lys Gln Trp
1               5                   10                  15

Thr Asn Leu Glu Arg Lys Pro Lys Pro Pro His Leu
            20                  25

<210> SEQ ID NO 49
<211> LENGTH: 405
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Ala Ala Ile Asn Ala Ser Ala His Pro Lys Ala Asn Gly
        35                  40                  45

Ser Ala Val Asn Leu Lys Ser Gly Ser Leu Asn Thr Gln Glu Asp Thr
    50                  55                  60
```

Ser Ser Ser Pro Pro Arg Ala Phe Leu Asn Gln Leu Pro Asp Trp
 65                  70                  75                  80

Ser Met Leu Leu Thr Ala Ile Thr Thr Val Phe Val Ala Ala Glu Lys
                 85                  90                  95

Gln Trp Thr Met Arg Asp Arg Lys Ser Lys Arg Pro Asp Met Leu Val
            100                 105                 110

Asp Ser Val Gly Leu Lys Ser Val Val Leu Asp Gly Leu Val Ser Arg
            115                 120                 125

Gln Ile Phe Ser Ile Arg Ser Tyr Glu Ile Gly Ala Asp Arg Thr Ala
        130                 135                 140

Ser Ile Glu Thr Leu Met Asn His Leu Gln Thr Ser Ile Asn His
145                 150                 155                 160

Cys Lys Ser Leu Gly Leu Leu Asn Asp Gly Phe Gly Arg Thr Pro Gly
                165                 170                 175

Met Cys Lys Asn Asp Leu Ile Trp Val Leu Thr Lys Met Gln Ile Met
            180                 185                 190

Val Asn Arg Tyr Pro Thr Trp Gly Asp Thr Val Glu Ile Asn Thr Trp
        195                 200                 205

Phe Ser His Ser Gly Lys Ile Gly Met Ala Ser Asp Trp Leu Ile Thr
    210                 215                 220

Asp Cys Asn Thr Gly Glu Ile Leu Ile Arg Ala Thr Ser Val Trp Ala
225                 230                 235                 240

Met Met Asn Gln Lys Thr Arg Arg Phe Ser Arg Leu Pro Tyr Glu Val
                245                 250                 255

Arg Gln Glu Leu Thr Pro His Tyr Val Asp Ser Pro His Val Ile Glu
            260                 265                 270

Asp Asn Asp Arg Lys Leu His Lys Phe Asp Val Lys Thr Gly Asp Ser
        275                 280                 285

Ile Arg Lys Gly Leu Thr Pro Arg Trp Asn Asp Leu Asp Val Asn Gln
    290                 295                 300

His Val Ser Asn Val Lys Tyr Ile Gly Trp Ile Leu Glu Ser Met Pro
305                 310                 315                 320

Ile Glu Val Leu Glu Thr Gln Glu Leu Cys Ser Leu Thr Val Glu Tyr
                325                 330                 335

Arg Arg Glu Cys Gly Met Asp Ser Val Leu Glu Ser Val Thr Ala Met
            340                 345                 350

Asp Pro Ser Glu Asp Glu Gly Arg Ser Gln Tyr Lys His Leu Leu Arg
        355                 360                 365

Leu Glu Asp Gly Thr Asp Ile Val Lys Gly Arg Thr Glu Trp Arg Pro
    370                 375                 380

Lys Asn Ala Gly Thr Asn Gly Ala Ile Ser Thr Ala Lys Pro Ser Asn
385                 390                 395                 400

Gly Asn Ser Val Ser
                405

<210> SEQ ID NO 50
<211> LENGTH: 377
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Met Ala Thr Ala Ser Thr Phe Ser Ala Phe Asn Ala Arg Cys Gly Asp

```
            1               5                  10                 15
        Leu Arg Arg Ser Ala Gly Ser Gly Pro Arg Arg Pro Ala Arg Pro Leu
                        20                 25                 30

Pro Val Arg Ala Ala Ile Asn Ala Ser Ala His Pro Lys Ala Asn Gly
                        35                 40                 45

Ser Ala Val Asn Leu Lys Ser Gly Ser Leu Asn Thr Gln Glu Asp Thr
         50                 55                 60

Ser Ser Ser Pro Pro Arg Ala Phe Leu Asn Gln Leu Pro Asp Trp
         65                 70                 75                 80

Ser Met Leu Val Asp Ser Val Gly Leu Lys Ser Val Val Leu Asp Gly
                        85                 90                 95

Leu Val Ser Arg Gln Ile Phe Ser Ile Arg Ser Tyr Glu Ile Gly Ala
                       100                105                110

Asp Arg Thr Ala Ser Ile Glu Thr Leu Met Asn His Leu Gln Glu Thr
                       115                120                125

Ser Ile Asn His Cys Lys Ser Leu Gly Leu Leu Asn Asp Gly Phe Gly
                       130                135                140

Arg Thr Pro Gly Met Cys Lys Asn Asp Leu Ile Trp Val Leu Thr Lys
        145                150                155                160

Met Gln Ile Met Val Asn Arg Tyr Pro Thr Trp Gly Asp Thr Val Glu
                       165                170                175

Ile Asn Thr Trp Phe Ser His Ser Gly Lys Ile Gly Met Ala Ser Asp
                       180                185                190

Trp Leu Ile Thr Asp Cys Asn Thr Gly Glu Ile Leu Ile Arg Ala Thr
                       195                200                205

Ser Val Trp Ala Met Met Asn Gln Lys Thr Arg Arg Phe Ser Arg Leu
                       210                215                220

Pro Tyr Glu Val Arg Gln Glu Leu Thr Pro His Tyr Val Asp Ser Pro
        225                230                235                240

His Val Ile Glu Asp Asn Asp Arg Lys Leu His Lys Phe Asp Val Lys
                       245                250                255

Thr Gly Asp Ser Ile Arg Lys Gly Leu Thr Pro Arg Trp Asn Asp Leu
                       260                265                270

Asp Val Asn Gln His Val Ser Asn Val Lys Tyr Ile Gly Trp Ile Leu
                       275                280                285

Glu Ser Met Pro Ile Glu Val Leu Glu Thr Gln Glu Leu Cys Ser Leu
                       290                295                300

Thr Val Glu Tyr Arg Arg Glu Cys Gly Met Asp Ser Val Leu Glu Ser
        305                310                315                320

Val Thr Ala Met Asp Pro Ser Glu Asp Glu Gly Arg Ser Gln Tyr Lys
                       325                330                335

His Leu Leu Arg Leu Glu Asp Gly Thr Asp Ile Val Lys Gly Arg Thr
                       340                345                350

Glu Trp Arg Pro Lys Asn Ala Gly Thr Asn Gly Ala Ile Ser Thr Ala
                       355                360                365

Lys Pro Ser Asn Gly Asn Ser Val Ser
                       370                375

<210> SEQ ID NO 51
<211> LENGTH: 339
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 51

```
Asn Ala Ser Ala His Pro Lys Ala Asn Gly Ser Ala Val Asn Leu Lys
1               5                   10                  15

Ser Gly Ser Leu Asn Thr Gln Glu Asp Thr Ser Ser Ser Pro Pro Pro
            20                  25                  30

Arg Ala Phe Leu Asn Gln Leu Pro Asp Trp Ser Met Leu Val Asp Ser
        35                  40                  45

Val Gly Leu Lys Ser Val Val Leu Asp Gly Leu Val Ser Arg Gln Ile
50                  55                  60

Phe Ser Ile Arg Ser Tyr Glu Ile Gly Ala Asp Arg Thr Ala Ser Ile
65                  70                  75                  80

Glu Thr Leu Met Asn His Leu Gln Glu Thr Ser Ile Asn His Cys Lys
                85                  90                  95

Ser Leu Gly Leu Leu Asn Asp Gly Phe Gly Arg Thr Pro Gly Met Cys
            100                 105                 110

Lys Asn Asp Leu Ile Trp Val Leu Thr Lys Met Gln Ile Met Val Asn
            115                 120                 125

Arg Tyr Pro Thr Trp Gly Asp Thr Val Glu Ile Asn Thr Trp Phe Ser
130                 135                 140

His Ser Gly Lys Ile Gly Met Ala Ser Asp Trp Leu Ile Thr Asp Cys
145                 150                 155                 160

Asn Thr Gly Glu Ile Leu Ile Arg Ala Thr Ser Val Trp Ala Met Met
                165                 170                 175

Asn Gln Lys Thr Arg Arg Phe Ser Arg Leu Pro Tyr Glu Val Arg Gln
            180                 185                 190

Glu Leu Thr Pro His Tyr Val Asp Ser Pro His Val Ile Glu Asp Asn
            195                 200                 205

Asp Arg Lys Leu His Lys Phe Asp Val Lys Thr Gly Asp Ser Ile Arg
210                 215                 220

Lys Gly Leu Thr Pro Arg Trp Asn Asp Leu Asp Val Asn Gln His Val
225                 230                 235                 240

Ser Asn Val Lys Tyr Ile Gly Trp Ile Leu Glu Ser Met Pro Ile Glu
                245                 250                 255

Val Leu Glu Thr Gln Glu Leu Cys Ser Leu Thr Val Glu Tyr Arg Arg
            260                 265                 270

Glu Cys Gly Met Asp Ser Val Leu Glu Ser Val Thr Ala Met Asp Pro
            275                 280                 285

Ser Glu Asp Glu Gly Arg Ser Gln Tyr Lys His Leu Leu Arg Leu Glu
            290                 295                 300

Asp Gly Thr Asp Ile Val Lys Gly Arg Thr Glu Trp Arg Pro Lys Asn
305                 310                 315                 320

Ala Gly Thr Asn Gly Ala Ile Ser Thr Ala Lys Pro Ser Asn Gly Asn
                325                 330                 335

Ser Val Ser
```

<210> SEQ ID NO 52
<211> LENGTH: 1203
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 52

-continued

| | |
|---|---|
| atggccaccg cctccacctt ctccgccttc aacgcccgct gcggcgacct gcgccgctcc | 60 |
| gccggctccg cccccgccg ccccgcccgc cccctgcccg tgcgcgccgc catcaacgcc | 120 |
| tccgcccacc ccaaggccaa cggctccgcc gtgaacctga agtccggctc cctgaacacc | 180 |
| caggaggaca cctcctcctc cccccccccc cgcgccttcc tgaaccagct gcccgactgg | 240 |
| tccatgctgg tggactccgt gggcctgaag tccgtggtgc tggacggcct ggtgtcccgc | 300 |
| cagatcttct ccatccgctc ctacgagatc ggcgccgacc gcaccgcctc catcgagacc | 360 |
| ctgatgaacc acctgcagga gacctccatc aaccactgca agtccctggg cctgctgaac | 420 |
| gacggcttcg gccgcacccc cggcatgtgc aagaacgacc tgatctgggt gctgaccaag | 480 |
| atgcagatca tggtgaaccg ctaccccacc tggggcgaca ccgtggagat caacacctgg | 540 |
| ttctccccact ccggcaagat cggcatggcc tccgactggc tgatcaccga ctgcaacacc | 600 |
| ggcgagatcc tgatccgcgc cacctccgtg tgggccatga tgaaccagaa gacccgccgc | 660 |
| ttctcccgcc tgccctacga ggtgcgccag gagctgaccc cccactacgt ggactccccc | 720 |
| cacgtgatcg aggacaacga ccgcaagctg cacaagttcg acgtgaagac cggcgactcc | 780 |
| atccgcaagg gcctgacccc ccgctggaac gacctggacg tgaaccagca cgtgtccaac | 840 |
| gtgaagtaca tcggctggat cctggagtcc atgcccatcg aggtgctgga cccaggag | 900 |
| ctgtgctccc tgaccgtgga gtaccgccgc gagtgcggca tggactccgt gctggagtcc | 960 |
| gtgaccgcca tggaccccttc cgaggacgag ggccgctccc agtacaagca cctgctgcgc | 1020 |
| ctggaggacg gcaccgacat cgtgaagggc cgcaccgagt ggcgccccaa gaacgccggc | 1080 |
| accaacggcg ccatctccac cgccaagccc tccaacggca actccgtgtc catggactac | 1140 |
| aaggaccacg acggcgacta caaggaccac gacatcgact acaaggacga cgacgacaag | 1200 |
| tga | 1203 |

<210> SEQ ID NO 53
<211> LENGTH: 415
<212> TYPE: PRT
<213> ORGANISM: Cuphea hookeriana

<400> SEQUENCE: 53

```
Met Val Ala Ala Ala Ser Ser Ala Phe Phe Pro Val Pro Ala Pro
1               5                   10                  15

Gly Ala Ser Pro Lys Pro Gly Lys Phe Gly Asn Trp Pro Ser Ser Leu
            20                  25                  30

Ser Pro Ser Phe Lys Pro Lys Ser Ile Pro Asn Gly Gly Phe Gln Val
        35                  40                  45

Lys Ala Asn Asp Ser Ala His Pro Lys Ala Asn Gly Ser Ala Val Ser
    50                  55                  60

Leu Lys Ser Gly Ser Leu Asn Thr Gln Glu Asp Thr Ser Ser Ser Pro
65                  70                  75                  80

Pro Pro Arg Thr Phe Leu His Gln Leu Pro Asp Trp Ser Arg Leu Leu
                85                  90                  95

Thr Ala Ile Thr Thr Val Phe Val Lys Ser Lys Arg Pro Asp Met His
            100                 105                 110

Asp Arg Lys Ser Lys Arg Pro Asp Met Leu Val Asp Ser Phe Gly Leu
        115                 120                 125

Glu Ser Thr Val Gln Asp Gly Leu Val Phe Arg Gln Ser Phe Ser Ile
    130                 135                 140

Arg Ser Tyr Glu Ile Gly Thr Asp Arg Thr Ala Ser Ile Glu Thr Leu
145                 150                 155                 160
```

Met Asn His Leu Gln Glu Thr Ser Leu Asn His Cys Lys Ser Thr Gly
                165                 170                 175

Ile Leu Leu Asp Gly Phe Gly Arg Thr Leu Glu Met Cys Lys Arg Asp
            180                 185                 190

Leu Ile Trp Val Val Ile Lys Met Gln Ile Lys Val Asn Arg Tyr Pro
        195                 200                 205

Ala Trp Gly Asp Thr Val Glu Ile Asn Thr Arg Phe Ser Arg Leu Gly
    210                 215                 220

Lys Ile Gly Met Gly Arg Asp Trp Leu Ile Ser Asp Cys Asn Thr Gly
225                 230                 235                 240

Glu Ile Leu Val Arg Ala Thr Ser Ala Tyr Ala Met Met Asn Gln Lys
                245                 250                 255

Thr Arg Arg Leu Ser Lys Leu Pro Tyr Glu Val His Gln Glu Ile Val
            260                 265                 270

Pro Leu Phe Val Asp Ser Pro Val Ile Glu Asp Ser Asp Leu Lys Val
        275                 280                 285

His Lys Phe Lys Val Lys Thr Gly Asp Ser Ile Gln Lys Gly Leu Thr
    290                 295                 300

Pro Gly Trp Asn Asp Leu Asp Val Asn Gln His Val Ser Asn Val Lys
305                 310                 315                 320

Tyr Ile Gly Trp Ile Leu Glu Ser Met Pro Thr Glu Val Leu Glu Thr
                325                 330                 335

Gln Glu Leu Cys Ser Leu Ala Leu Glu Tyr Arg Arg Glu Cys Gly Arg
            340                 345                 350

Asp Ser Val Leu Glu Ser Val Thr Ala Met Asp Pro Ser Lys Val Gly
        355                 360                 365

Val Arg Ser Gln Tyr Gln His Leu Leu Arg Leu Glu Asp Gly Thr Ala
    370                 375                 380

Ile Val Asn Gly Ala Thr Glu Trp Arg Pro Lys Asn Ala Gly Ala Asn
385                 390                 395                 400

Gly Ala Ile Ser Thr Gly Lys Thr Ser Asn Gly Asn Ser Val Ser
                405                 410                 415

<210> SEQ ID NO 54
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Pro Ala Arg Pro Leu
            20                  25                  30

Pro Val Arg Ala Ala Ile Asn Asp Ser Ala His Pro Lys Ala Asn Gly
        35                  40                  45

Ser Ala Val Ser Leu Lys Ser Gly Ser Leu Asn Thr Gln Glu Asp Thr
    50                  55                  60

Ser Ser Pro Pro Pro Arg Thr Phe Leu His Gln Leu Pro Asp Trp
65                  70                  75                  80

Ser Arg Leu Val Asp Ser Phe Gly Leu Glu Thr Val Gln Asp Gly
                85                  90                  95

Leu Val Phe Arg Gln Ser Phe Ser Ile Arg Ser Tyr Glu Ile Gly Thr 100                 105                 110
Asp Arg Thr Ala Ser Ile Glu Thr Leu Met Asn His Leu Gln Glu Thr
            115                 120                 125

Ser Leu Asn His Cys Lys Ser Thr Gly Ile Leu Leu Asp Gly Phe Gly
        130                 135                 140

Arg Thr Leu Glu Met Cys Lys Arg Asp Leu Ile Trp Val Val Ile Lys
145                 150                 155                 160

Met Gln Ile Lys Val Asn Arg Tyr Pro Ala Trp Gly Asp Thr Val Glu
                165                 170                 175

Ile Asn Thr Arg Phe Ser Arg Leu Gly Lys Ile Gly Met Gly Arg Asp
                180                 185                 190

Trp Leu Ile Ser Asp Cys Asn Thr Gly Glu Ile Leu Val Arg Ala Thr
            195                 200                 205

Ser Ala Tyr Ala Met Met Asn Gln Lys Thr Arg Arg Leu Ser Lys Leu
        210                 215                 220

Pro Tyr Glu Val His Gln Glu Ile Val Pro Leu Phe Val Asp Ser Pro
225                 230                 235                 240

Val Ile Glu Asp Ser Asp Leu Lys Val His Lys Phe Lys Val Lys Thr
                245                 250                 255

Gly Asp Ser Ile Gln Lys Gly Leu Thr Pro Gly Trp Asn Asp Leu Asp
                260                 265                 270

Val Asn Gln His Val Ser Asn Val Lys Tyr Ile Gly Trp Ile Leu Glu
            275                 280                 285

Ser Met Pro Thr Glu Val Leu Glu Thr Gln Glu Leu Cys Ser Leu Ala
        290                 295                 300

Leu Glu Tyr Arg Arg Glu Cys Gly Arg Asp Ser Val Leu Glu Ser Val
305                 310                 315                 320

Thr Ala Met Asp Pro Ser Lys Val Gly Val Arg Ser Gln Tyr Gln His
                325                 330                 335

Leu Leu Arg Leu Glu Asp Gly Thr Ala Ile Val Asn Gly Ala Thr Glu
                340                 345                 350

Trp Arg Pro Lys Asn Ala Gly Ala Asn Gly Ala Ile Ser Thr Gly Lys
            355                 360                 365

Thr Ser Asn Gly Asn Ser Val Ser
        370                 375

<210> SEQ ID NO 55
<211> LENGTH: 338
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 55

Asn Asp Ser Ala His Pro Lys Ala Asn Gly Ser Ala Val Ser Leu Lys
1               5                   10                  15

Ser Gly Ser Leu Asn Thr Gln Glu Asp Thr Ser Ser Pro Pro
            20                  25                  30

Arg Thr Phe Leu His Gln Leu Pro Asp Trp Ser Arg Leu Val Asp Ser
                35                  40                  45

Phe Gly Leu Glu Ser Thr Val Gln Asp Gly Leu Val Phe Arg Gln Ser
        50                  55                  60

Phe Ser Ile Arg Ser Tyr Glu Ile Gly Thr Asp Arg Thr Ala Ser Ile
65                  70                  75                  80

Glu Thr Leu Met Asn His Leu Gln Glu Thr Ser Leu Asn His Cys Lys
            85                  90                  95

Ser Thr Gly Ile Leu Leu Asp Gly Phe Gly Arg Thr Leu Glu Met Cys
        100                 105                 110

Lys Arg Asp Leu Ile Trp Val Ile Lys Met Gln Ile Lys Val Asn
        115                 120                 125

Arg Tyr Pro Ala Trp Gly Asp Thr Val Glu Ile Asn Thr Arg Phe Ser
        130                 135                 140

Arg Leu Gly Lys Ile Gly Met Gly Arg Asp Trp Leu Ile Ser Asp Cys
145                 150                 155                 160

Asn Thr Gly Glu Ile Leu Val Arg Ala Thr Ser Ala Tyr Ala Met Met
                165                 170                 175

Asn Gln Lys Thr Arg Arg Leu Ser Lys Leu Pro Tyr Glu Val His Gln
            180                 185                 190

Glu Ile Val Pro Leu Phe Val Asp Ser Pro Val Ile Glu Asp Ser Asp
        195                 200                 205

Leu Lys Val His Lys Phe Lys Val Lys Thr Gly Asp Ser Ile Gln Lys
        210                 215                 220

Gly Leu Thr Pro Gly Trp Asn Asp Leu Asp Val Asn Gln His Val Ser
225                 230                 235                 240

Asn Val Lys Tyr Ile Gly Trp Ile Leu Glu Ser Met Pro Thr Glu Val
                245                 250                 255

Leu Glu Thr Gln Glu Leu Cys Ser Leu Ala Leu Glu Tyr Arg Arg Glu
            260                 265                 270

Cys Gly Arg Asp Ser Val Leu Glu Ser Val Thr Ala Met Asp Pro Ser
        275                 280                 285

Lys Val Gly Val Arg Ser Gln Tyr Gln His Leu Leu Arg Leu Glu Asp
        290                 295                 300

Gly Thr Ala Ile Val Asn Gly Ala Thr Glu Trp Arg Pro Lys Asn Ala
305                 310                 315                 320

Gly Ala Asn Gly Ala Ile Ser Thr Gly Lys Thr Ser Asn Gly Asn Ser
                325                 330                 335

Val Ser

<210> SEQ ID NO 56
<211> LENGTH: 1200
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
atggccaccg cctccacctt ctccgccttc aacgcccgct gcggcgacct gcgccgctcc      60
gccggctccg gcccccgccg cccgcccgc cccctgcccg tgcgcgccgc catcaacgac     120
tccgcccacc ccaaggccaa cggctccgcc gtgagcctga agtccggcag cctgaacacc     180
caggaggaca cctcctccag ccccccccc cgcaccttcc tgcaccagct gcccgactgg     240
agccgcctgg tggacagctt cggcctggag tccaccgtgc aggacggcct ggtgttccgc     300
cagtccttct ccatccgctc ctacgagatc ggcaccgacc gcaccgccag catcgagacc     360
ctgatgaacc acctgcagga gacctccctg aaccactgca gagcaccgg catcctgctg     420 gacggcttcg gccgcaccct ggagatgtgc aagcgcgacc tgatctgggt ggtgatcaag     480
atgcagatca aggtgaaccg ctaccccgcc tggggcgaca ccgtggagat caacacccgc     540

| | |
|---|---|
| ttcagccgcc tgggcaagat cggcatgggc cgcgactggc tgatctccga ctgcaacacc | 600 |
| ggcgagatcc tggtgcgcgc caccagcgcc tacgccatga tgaaccagaa gacccgccgc | 660 |
| ctgtccaagc tgccctacga ggtgcaccag agatcgtgc ccctgttcgt ggacagcccc | 720 |
| gtgatcgagg actccgacct gaaggtgcac aagttcaagg tgaagaccgg cgacagcatc | 780 |
| cagaagggcc tgaccccgg ctggaacgac ctggacgtga accagcacgt gtccaacgtg | 840 |
| aagtacatcg gctggatcct ggagagcatg cccaccgagg tgctggagac ccaggagctg | 900 |
| tgctccctgg ccctggagta ccgccgcgag tgcggccgcg actccgtgct ggagagcgtg | 960 |
| accgccatgg accccagcaa ggtgggcgtg cgctcccagt accagcacct gctgcgcctg | 1020 |
| gaggacggca ccgccatcgt gaacggcgcc accgagtggc gccccaagaa cgccggcgcc | 1080 |
| aacggcgcca tctccaccgg caagaccagc aacggcaact ccgtgtccat ggactacaag | 1140 |
| gaccacgacg gcgactacaa ggaccacgac atcgactaca aggacgacga cgacaagtga | 1200 |

<210> SEQ ID NO 57
<211> LENGTH: 6046
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

| | |
|---|---|
| caccggcgcg ctgcttcgcg tgccgggtgc agcaatcaga tccaagtctg acgacttgcg | 60 |
| cgcacgcgcc ggatccttca attccaaagt gtcgtccgcg tgcgcttctt cgccttcgtc | 120 |
| ctcttgaaca tccagcgacg caagcgcagg gcgctgggcg gctggcgtcc cgaaccggcc | 180 |
| tcggcgcacg cggctgaaat tgccgatgtc ggcaatgtag tgccgctccg cccacctctc | 240 |
| aattaagttt ttcagcgcgt ggttgggaat gatctgcgct catggggcga agaaggggt | 300 |
| tcagaggtgc tttattgtta ctcgactggg cgtaccagca ttcgtgcatg actgattata | 360 |
| catacaaaag tacagctcgc ttcaatgccc tgcgattcct actcccgagc gagcactcct | 420 |
| ctcaccgtcg ggttgcttcc cacgaccacg ccggtaagag ggtctgtggc ctcgcgcccc | 480 |
| tcgcgagcgc atctttccag ccacgtctgt atgattttgc gctcatacgt ctggcccgtc | 540 |
| gaccccaaaa tgacgggatc ctgcataata tcgcccgaaa tgggatccag gcattcgtca | 600 |
| ggaggcgtca gccccgcggg agatgccggt cccgccgcat tggaaaggtg tagaggggt | 660 |
| gaatccccca tttcatgaaa tgggtacccc gctcccgtct ggtcctcacg ttcgtgtacg | 720 |
| gcctggatcc cggaaagggc ggatgcacgt ggtgttgccc cgccattggc gcccacgttt | 780 |
| caaagtcccc ggccagaaat gcacaggacc ggcccggctc gcacaggcca tgacgaatgc | 840 |
| ccagatttcg acagcaaaac aatctggaat aatcgcaacc attcgcgttt tgaacgaaac | 900 |
| gaaaagacgc tgtttagcac gtttccgata tcgtgggggc cgaagcatga ttggggggag | 960 |
| gaaagcgtgg cccaaggta gcccattctg tgccacacgc cgacgaggac caatccccgg | 1020 |
| catcagcctt catcgacggc tgcgccgcac atataaagcc ggacgccttc ccgacacgtt | 1080 |
| caaacagttt tatttcctcc acttcctgaa tcaaacaaat cttcaaggaa gatcctgctc | 1140 |
| ttgagcaact cgtatgttcg cgttctactt cctgacggcc tgcatctccc tgaagggcgt | 1200 |
| gttcggcgtc tccccctcct acaacggcct gggcctgacg ccccagatgg gctgggacaa | 1260 |
| ctggaacacg ttcgcctgcg acgtctccga gcagctgctg ctggacacgg ccgaccgcat | 1320 |
| ctccgacctg ggcctgaagg acatgggcta caagtacatc atcctggacg actgctggtc | 1380 |

```
ctccggccgc gactccgacg gcttcctggt cgccgacgag cagaagttcc ccaacggcat    1440
gggccacgtc gccgaccacc tgcacaacaa ctccttcctg ttcggcatgt actcctccgc    1500
gggcgagtac acgtgcgccg gctacccggg ctccctgggc cgcgaggagg aggacgccca    1560
gttcttcgcg aacaaccgcg tggactacct gaagtacgac aactgctaca caagggcca    1620
gttcggcacg cccgagatct cctaccaccg ctacaaggcc atgtccgacg ccctgaacaa    1680
gacgggccgc cccatcttct actccctgtg caactgggc caggacctga ccttctactg    1740
gggctccggc atcgcgaact cctggcgcat gtccggcgac gtcacggcgg agttcacgcg    1800
cccgactcc cgctgcccct gcgacggcga cgagtacgac tgcaagtacg ccggcttcca    1860
ctgctccatc atgaacatcc tgaacaaggc cgcccccatg ggccagaacg cgggcgtcgg    1920
cggctggaac gacctggaca acctggaggt cggcgtcggc aacctgacgg acgacgagga    1980
gaaggcgcac ttctccatgt gggccatggt gaagtccccc ctgatcatcg gcgcgaacgt    2040
gaacaacctg aaggcctcct cctactccat ctactcccag gcgtccgtca tcgccatcaa    2100
ccaggactcc aacggcatcc ccgccacgcg cgtctggcgc tactacgtgt ccgacacgga    2160
cgagtacggc cagggcgaga tccagatgtg gtccggcccc ctggacaacg cgaccaggt    2220
cgtggcgctg ctgaacggcg gctccgtgtc ccgccccatg aacacgaccc tggaggagat    2280
cttcttcgac tccaacctgg gctccaagaa gctgacctcc acctgggaca tctacgacct    2340
gtgggcgaac cgcgtcgaca actccacggc gtccgccatc ctgggccgca caagaccgc    2400
caccggcatc ctgtacaacg ccaccgagca gtcctacaag gacggcctgt ccaagaacga    2460
cacccgcctg ttcggccaga agatcggctc cctgtccccc aacgcgatcc tgaacacgac    2520
cgtccccgcc cacggcatcg cgttctaccg cctgcgcccc tcctcctgat acaacttatt    2580
acgtattctg accggcgctg atgtggcgcg gacgccgtcg tactctttca gactttactc    2640
ttgaggaatt gaacctttct cgcttgctgg catgtaaaca ttggcgcaat taattgtgtg    2700
atgaagaaag ggtggcacaa gatggatcgc gaatgtacga gatcgacaac gatggtgatt    2760
gttatgaggg gccaaacctg gctcaatctt gtcgcatgtc cggcgcaatg tgatccagcg    2820
gcgtgactct cgcaacctgg tagtgtgtgc gcaccgggtc gctttgatta aaactgatcg    2880
cattgccatc ccgtcaactc acaagcctac tctagctccc attgcgcact cgggcgcccg    2940
gctcgatcaa tgttctgagc ggagggcgaa gcgtcaggaa atcgtctcgg cagctggaag    3000
cgcatggaat gcggagcgga gatcgaatca ggatcccgcg tctcgaacag agcgcgcaga    3060
ggaacgctga aggtctcgcc tctgtcgcac ctcagcgcgg catacaccac aataaccacc    3120
tgacgaatgc gcttggttct tcgtccatta gcgaagcgtc cggttcacac acgtgccacg    3180
ttggcgaggt ggcaggtgac aatgatcggt ggagctgatg gtcgaaacgt tcacagccta    3240
gggatatcgt gaaaactcgc tcgaccgccc gcgtcccgca ggcagcgatg acgtgtgcgt    3300
gacctgggtg tttcgtcgaa aggccagcaa ccccaaatcg caggcgatcc ggagattggg    3360
atctgatccg agcttggacc agatccccca cgatgcggca cggaactgc atcgactcgg    3420
cgcggaaccc agctttcgta aatgccagat tggtgtccga taccttgatt tgccatcagc    3480
gaaacaagac ttcagcagcg agcgtatttg gcgggcgtgc taccagggtt gcatacattg    3540
cccatttctg tctggaccgc tttaccggcg cagagggtga gttgatgggg ttggcaggca    3600
tcgaaacgcg cgtgcatggt gtgtgtgtct gttttcggct gcacaatttc aatagtcgga    3660
tgggcgacgg tagaattggg tgttgcgctc gcgtgcatgc ctcgcccgt cgggtgtcat    3720
gaccgggact ggaatccccc ctcgcgaccc tcctgctaac gctcccgact ctcccgcccg    3780
```

```
cgcgcaggat agactctagt tcaaccaatc gacaactagt atggccaccg catccacttt      3840
ctcggcgttc aatgcccgct gcggcgacct gcgtcgctcg gcgggctccg ggccccggcg      3900
cccagcgagg cccctccccg tgcgcgggcg cgcctcccag ctgcgcaagc ccgccctgga      3960
cccccctgcgc gccgtgatct ccgccgacca gggctccatc tccccgtga actcctgcac      4020
ccccgccgac cgcctgcgcg ccggccgcct gatggaggac ggctactcct acaaggagaa      4080
gttcatcgtg cgctcctacg aggtgggcat caacaagacc gccaccgtgg agaccatcgc      4140
caacctgctg caggaggtgg cctgcaacca cgtgcagaag tgcggcttct ccaccgacgg      4200
cttcgccacc accctgacca tgcgcaagct gcacctgatc tgggtgaccg cccgcatgca      4260
catcgagatc tacaagtacc ccgcctggtc cgacgtggtg gagatcgaga cctggtgcca      4320
gtccgagggc cgcatcggca cccgccgcga ctggatcctg cgcgactccg ccaccaacga      4380
ggtgatcggc cgcgccacct ccaagtgggt gatgatgaac caggacaccc gccgcctgca      4440
gcgcgtgacc gacgaggtgc gcgacgagta cctggtgttc tgcccccgcg agccccgcct      4500
ggccttcccc gaggagaaca actcctccct gaagaagatc cccaagctgg aggacccgc       4560
ccagtactcc atgctggagc tgaagccccg ccgcgccgac ctggacatga accagcacgt      4620
gaacaacgtg acctacatcg gctgggtgct ggagtccatc ccccaggaga tcatcgacac      4680
ccacgagctg caggtgatca ccctggacta ccgccgcgag tgccagcagg acgacatcgt      4740
ggactccctg accacctccg agatccccga cgaccccatc tccaagttca ccggcaccaa      4800
cggctccgcc atgtcctcca tccagggcca aacgagtcc cagttcctgc acatgctgcg      4860
cctgtccgag aacggccagg agatcaaccg cggccgcacc cagtggcgca agaagtcctc      4920
ccgcatggac tacaaggacc acgacggcga ctacaaggac cacgacatcg actacaagga      4980
cgacgacgac aagtgaatcg atggagcgac gagtgtgcgt gcggggctgg cgggagtggg      5040
acgccctcct cgctcctctc tgttctgaac ggaacaatcg gccacccgc gctacgcgcc       5100
acgcatcgag caacgaagaa accccccga tgataggttg cggtggctgc cgggatatag       5160
atccggccgc acatcaaagg gcccctccgc cagagaagaa gctcctttcc cagcagactc      5220
cttctgctgc caaaacactt ctctgtccac agcaacacca aaggatgaac agatcaactt      5280
gcgtctccgc gtagcttcct cggctagcgt gcttgcaaca ggtccctgca ctattatctt      5340
cctgcttttcc tctgaattat gcggcaggcg agcgctcgct ctggcgagcg ctccttcgcg      5400
ccgccctcgc tgatcgagtg tacagtcaat gaatggtgag ctccgcgcct gcgcgaggac      5460
gcagaacaac gctgccgccg tgtcttttgc acgcgcgact ccggcgcttc gctggtggca      5520
ccccccataaa gaaaccctca attctgtttg tggaagacac ggtgtacccc cacccaccca      5580
cctgcacctc tattattggt attattgacg cgggagtggg cgttgtaccc tacaacgtag      5640
cttctctagt tttcagctgg ctcccaccat tgtaaattca tgctagaata gtgcgtggtt      5700
atgtgagagg tatagtgtgt ctgagcagac ggggcgggat gcatgtcgtg gtggtgatct      5760
ttggctcaag gcgtcgtcga cgtgacgtgc ccgatcatga gagcaatacc gcgctcaaag      5820
ccgacgcata gcctttactc cgcaatccaa acgactgtcg ctcgtatttt ttggatatct      5880
atttaaaga gcgagcacag cgccgggcat gggcctgaaa ggcctcgcgg ccgtgctcgt      5940
ggtgggggcc gcgagcgcgt ggggcatcgc ggcagtgcac caggcgcaga cggaggaacg      6000
catggtgcgt gcgcaatata agatacatgt attgttgtcc tgcagg                   6046
```

<210> SEQ ID NO 58

```
<211> LENGTH: 1176
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
atggccaccg catccacttt ctcggcgttc aatgcccgct gcggcgacct gcgtcgctcg      60
gcgggctccg ggccccggcg cccagcgagg cccctccccg tgcgcgggcg cgcctcccag     120
ctgcgcaagc ccgccctgga ccccctgcgc gccgtgatct ccgccgacca gggctccatc     180
tcccccgtga actcctgcac ccccgccgac cgcctgcgcg ccggccgcct gatggaggac     240
ggctactcct acaaggagaa gttcatcgtg cgctcctacg aggtgggcat caacaagacc     300
gccaccgtgg agaccatcgc caacctgctg caggaggtgg cctgcaacca cgtgcagaag     360
tgcggcttct ccaccgccgg cttcgccacc accctgacca tgcgcaagct gcacctgatc     420
tgggtgaccg cccgcatgca catcgagatc tacaagtacc cgcctggtc cgacgtggtg      480
gagatcgaga cctggtgcca gtccgagggc cgcatcggca cccgccgcga ctggatcctg     540
cgcgactccg ccaccaacga ggtgatcggc cgcgccacct ccaagtgggt gatgatgaac     600
caggacaccc cgccgctgca gcgcgtgacc gacgaggtgc gcgacgagta cctggtgttc     660
tgcccccgcg agcccgcct ggccttcccc gaggagaaca actcctcct gaagaagatc       720
cccaagctgg aggaccccgc ccagtactcc atgctggagc tgaagccccg ccgcgccgac     780
ctggacatga accagcacgt gaacaacgtg acctacatcg gctgggtgct ggagtccatc     840
ccccaggaga tcatcgacac ccacgagctg caggtgatca ccctggacta ccgccgcgag     900
tgccagcagg acgacatcgt ggactccctg accacctccg agatccccga cgaccccatc     960
tccaagttca ccggcaccaa cggctccgcc atgtcctcca tccagggcca acgagtcc      1020
cagttcctgc acatgctgcg cctgtccgag aacggccagg agatcaaccg cggccgcacc    1080
cagtggcgca agaagtcctc ccgcatggac tacaaggacc acgacggcga ctacaaggac    1140
cacgacatcg actacaagga cgacgacgac aagtga                              1176

<210> SEQ ID NO 59
<211> LENGTH: 1176
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
atggccaccg catccacttt ctcggcgttc aatgcccgct gcggcgacct gcgtcgctcg      60
gcgggctccg ggccccggcg cccagcgagg cccctccccg tgcgcgggcg cgcctcccag     120
ctgcgcaagc ccgccctgga ccccctgcgc gccgtgatct ccgccgacca gggctccatc     180
tcccccgtga actcctgcac ccccgccgac cgcctgcgcg ccggccgcct gatggaggac     240
ggctactcct acaaggagaa gttcatcgtg cgctcctacg aggtgggcat caacaagacc     300
gccaccgtgg agaccatcgc caacctgctg caggaggtgg cctgcaacca cgtgcagaag     360
tgcggcttct ccaccgacgg cttcgccacc accctgacca tgcgcaagct gcacctgatc     420
tgggtgaccg cccgcatgca catcgagatc tacaagtacc cgcctggtc cgacgtggtg      480
gagatcgaga cctggtgcca gtccgagggc cgcatcggca cccgccgcga ctggatcctg     540
cgcgactccg ccaccaacga ggtgatcggc cgcgccacct ccaagtgggt gatgatgaac     600
```

```
caggacaccc gccgcctgca gcgcgtgacc gccgaggtgc gcgacgagta cctggtgttc    660 tgccccgcg  agccccgcct ggccttcccc gaggagaaca actcctccct gaagaagatc    720
cccaagctgg aggaccccgc ccagtactcc atgctggagc tgaagcccg  ccgcgccgac    780 ctggacatga accagcacgt gaacaacgtg acctacatcg gctgggtgct ggagtccatc    840
ccccaggaga tcatcgacac ccacgagctg caggtgatca ccctggacta ccgccgcgag    900
tgccagcagg acgacatcgt ggactccctg accacctccg agatcccga  cgaccccatc    960 tccaagttca ccggcaccaa cggctccgcc atgtcctcca tccagggcca acgagtcc    1020 cagttcctgc acatgctgcg cctgtccgag aacggccagg agatcaaccg cggccgcacc   1080
cagtggcgca agaagtcctc ccgcatggac tacaaggacc acgacggcga ctacaaggac   1140
cacgacatcg actacaagga cgacgacgac aagtga                             1176
```

<210> SEQ ID NO 60
<211> LENGTH: 1176
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60

```
atggccaccg catccacttt ctcggcgttc aatcccgct  gcggcgacct gcgtcgctcg     60
gcgggctccg ggccccggcg cccagcgagg cccctcccg  tgcgcgggcg cgcctcccag    120
ctgcgcaagc ccgccctgga ccccctgcgc gccgtgatct ccgccgacca gggctccatc    180
tcccccgtga actcctgcac ccccgccgac cgcctgcgcg ccggccgcct gatggaggac    240
ggctactcct acaaggagaa gttcatcgtg cgctcctacg aggtgggcat caacaagacc    300
gccaccgtgg agaccatcgc caacctgctg caggaggtgg cctgcaacca cgtgcagaag    360
tgcggcttct ccaccgccgg cttcgccacc accctgacca tgcgcaagct gcacctgatc    420
tgggtgaccg cccgcatgca catcgagatc tacaagtacc ccgcctggtc cgacgtggtg    480
gagatcgaga cctggtgcca gtccgagggc cgcatcggca cccgccgcga ctggatcctg    540
cgcgactccg ccaccaacga ggtgatcggc cgcgccacct ccaagtgggt gatgatgaac    600
caggacaccc gccgcctgca gcgcgtgacc gccgaggtgc gcgacgagta cctggtgttc    660 tgccccgcg  agccccgcct ggccttcccc gaggagaaca actcctccct gaagaagatc    720
cccaagctgg aggaccccgc ccagtactcc atgctggagc tgaagcccg  ccgcgccgac    780 ctggacatga accagcacgt gaacaacgtg acctacatcg gctgggtgct ggagtccatc    840
ccccaggaga tcatcgacac ccacgagctg caggtgatca ccctggacta ccgccgcgag    900
tgccagcagg acgacatcgt ggactccctg accacctccg agatcccga  cgaccccatc    960 tccaagttca ccggcaccaa cggctccgcc atgtcctcca tccagggcca acgagtcc    1020 cagttcctgc acatgctgcg cctgtccgag aacggccagg agatcaaccg cggccgcacc   1080
cagtggcgca agaagtcctc ccgcatggac tacaaggacc acgacggcga ctacaaggac   1140
cacgacatcg actacaagga cgacgacgac aagtga                             1176
```

<210> SEQ ID NO 61
<211> LENGTH: 368
<212> TYPE: PRT
<213> ORGANISM: Brassica napus

<400> SEQUENCE: 61

```
Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala Ser Gln Leu Arg Lys Pro Ala Leu Asp Pro
        35                  40                  45

Leu Arg Ala Val Ile Ser Ala Asp Gln Gly Ser Ile Ser Pro Val Asn
    50                  55                  60

Ser Cys Thr Pro Ala Asp Arg Leu Arg Ala Gly Arg Leu Met Glu Asp
65                  70                  75                  80

Gly Tyr Ser Tyr Lys Glu Lys Phe Ile Val Arg Ser Tyr Glu Val Gly
                85                  90                  95

Ile Asn Lys Thr Ala Thr Val Glu Thr Ile Ala Asn Leu Leu Gln Glu
                100                 105                 110

Val Ala Cys Asn His Val Gln Lys Cys Gly Phe Ser Thr Asp Gly Phe
            115                 120                 125

Ala Thr Thr Leu Thr Met Arg Lys Leu His Leu Ile Trp Val Thr Ala
130                 135                 140

Arg Met His Ile Glu Ile Tyr Lys Tyr Pro Ala Trp Ser Asp Val Val
145                 150                 155                 160

Glu Ile Glu Thr Trp Cys Gln Ser Glu Gly Arg Ile Gly Thr Arg Arg
                165                 170                 175

Asp Trp Ile Leu Arg Asp Ser Ala Thr Asn Glu Val Ile Gly Arg Ala
                180                 185                 190

Thr Ser Lys Trp Val Met Met Asn Gln Asp Thr Arg Arg Leu Gln Arg
        195                 200                 205

Val Thr Asp Glu Val Arg Asp Glu Tyr Leu Val Phe Cys Pro Arg Glu
    210                 215                 220

Pro Arg Leu Ala Phe Pro Glu Glu Asn Asn Ser Ser Leu Lys Lys Ile
225                 230                 235                 240

Pro Lys Leu Glu Asp Pro Ala Gln Tyr Ser Met Leu Glu Leu Lys Pro
                245                 250                 255

Arg Arg Ala Asp Leu Asp Met Asn Gln His Val Asn Asn Val Thr Tyr
                260                 265                 270

Ile Gly Trp Val Leu Glu Ser Ile Pro Gln Glu Ile Ile Asp Thr His
            275                 280                 285

Glu Leu Gln Val Ile Thr Leu Asp Tyr Arg Arg Glu Cys Gln Gln Asp
290                 295                 300

Asp Ile Val Asp Ser Leu Thr Thr Ser Glu Ile Pro Asp Asp Pro Ile
305                 310                 315                 320

Ser Lys Phe Thr Gly Thr Asn Gly Ser Ala Met Ser Ser Ile Gln Gly
                325                 330                 335

His Asn Glu Ser Gln Phe Leu His Met Leu Arg Leu Ser Glu Asn Gly
                340                 345                 350

Gln Glu Ile Asn Arg Gly Arg Thr Gln Trp Arg Lys Lys Ser Ser Arg
                355                 360                 365

<210> SEQ ID NO 62
<211> LENGTH: 4
<212> TYPE: PRT
<213> ORGANISM: Unknown
<220> FEATURE:
<223> OTHER INFORMATION: Description of Unknown:
      hydrophobic domain motif
```

```
<400> SEQUENCE: 62

Leu Pro Asp Trp
1
```